United States Patent
Olenyuk et al.

(10) Patent No.: US 9,416,145 B2
(45) Date of Patent: Aug. 16, 2016

(54) COMPOSITIONS AND METHODS FOR INHIBITING ACTIVITY OF HYPOXIA-INDUCIBLE TRANSCRIPTION FACTOR COMPLEX AND ITS USE FOR TREATMENT OF TUMORS

(71) Applicant: University of Southern California, Los Angeles, CA (US)

(72) Inventors: Bogdan Z. Olenyuk, Sierra Madre, CA (US); Ramin Dubey, Alhambra, CA (US); Michael D. Levin, San Diego, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 0 days.

(21) Appl. No.: 14/424,996

(22) PCT Filed: Mar. 15, 2013

(86) PCT No.: PCT/US2013/032523
§ 371 (c)(1),
(2) Date: Feb. 27, 2015

(87) PCT Pub. No.: WO2014/035484
PCT Pub. Date: Mar. 6, 2014

(65) Prior Publication Data
US 2015/0246933 A1    Sep. 3, 2015

Related U.S. Application Data

(60) Provisional application No. 61/694,717, filed on Aug. 29, 2012.

(51) Int. Cl.
*C07D 513/08* (2006.01)
*C07D 513/18* (2006.01)

(52) U.S. Cl.
CPC ................... *C07D 513/08* (2013.01)

(58) Field of Classification Search
CPC ...................... C07D 513/08; C07D 513/18
See application file for complete search history.

(56) References Cited

U.S. PATENT DOCUMENTS

| 5,728,830 A | 3/1998 | Kanda et al. |
| 2000/9026442 | 10/2009 | Bible et al. |
| 2009/0281109 A1 | 11/2009 | Cook et al. |

FOREIGN PATENT DOCUMENTS

| EP | 0670314 A1 | 9/1995 |
| WO | 95/08542 A1 | 3/1995 |

OTHER PUBLICATIONS

Dubey et al. (Journal of the American Chemical Society (2013), 135(11), 4537-4549).*
Williams. Epidithia-2,5-piperazinediones: Total Synthesis of the Hyalodendrins. Massachusetts Institute of Technology, Jun. 1979, pp. 1-206. entire document.
Coleman et al. Antifungal Activity of Microbial Secondary Metabolites. PLoS ONE 6(9): 1-9, 2011. entire document.
International Preliminary Report on Patentability dated Mar. 3, 2015 issued in corresponding PCT application PCT/US2013/032523.
Katherine M. Block et al., "Direct Inhibition of Hypoxia-Inducible Transcription Factor Complex with Designed Dimeric Epidithiodiketopiperazine", Journal of the American Chemical Society, vol. 131, No. 50, Dec. 23, 2009, pp. 18078-18088.
Supplementary European Search Report dated Feb. 10, 2016 issued on counterpart European Application No. 13832341.
English translation of First Office Action dated Mar. 2, 2016 issued in counterpart Japanese Patent Application No. 2015-529791.

* cited by examiner

*Primary Examiner* — Bruck Kifle
(74) *Attorney, Agent, or Firm* — DLA Piper LLP (US)

(57) ABSTRACT

Disclosed are epidithiodiketopiperazine compounds, pharmaceutical compositions based thereon and methods of treating, reducing or inhibiting transcription and translation of hypoxia-inducible genes.

12 Claims, 24 Drawing Sheets

Chaetocin

Chetomin

Synthesis of bicyclic thioacetals and single-ring ETPs.

a: p-Anisaldehyde, BF$_3$-Et$_2$O, DCM, RT, 16h, 92% b: mCPBA, ME$_2$S, HClO$_4$, c: BOMCl, nBuLi, THF, -78 °C, d: BCl$_3$, CH$_2$Cl$_2$, e: AcCl, pyridine, CH$_2$Cl$_2$, f. nBuLI, THF, -78 °C, BnCl.

Synthesis of bridged ETPs a: 7, nBuLi, THF, -78°C, b: BCl₃, CH₂Cl₂, c: mCPBA, Me₂S, HClO₄, d: nBuLi, THF, -78°C

COMPOSITIONS AND METHODS FOR INHIBITING ACTIVITY OF HYPOXIA-INDUCIBLE TRANSCRIPTION FACTOR COMPLEX AND ITS USE FOR TREATMENT OF TUMORS

CROSS-REFERENCE TO RELATED APPLICATIONS

This application is a national phase of International Application Number PCT/US2013/032523, filed on Mar. 15, 2013, which claims the benefit of U.S. Provisional Application No. 61/694,717, filed Aug. 29, 2012, the entire contents of all of which are hereby incorporated herein by reference.

STATEMENT REGARDING FEDERALLY SPONSORED RESEARCH AND DEVELOPMENT

This invention was made with government support under Contract No, CHE-1161644 awarded by the National Science Foundation. The government has certain rights in the invention.

FIELD OF THE INVENTION

This invention relates to epidithiodiketopiperazine compounds, pharmaceutical compositions based thereon and methods of treating, reducing or inhibiting transcription and translation of hypoxia-inducible genes.

BACKGROUND OF THE INVENTION

The high rate of cancer morbidity and mortality remains a major concern among the population in Western societies. In addition to having an impact on the cancer patients and members of their immediate families, cancer inflicts a large burden on society. The cost of cancer treatment and patient care is typically high and contributes to increased cost of health insurance and results, in turn, in a higher percentage of uninsured people and, consequently, in an increased economic burden when uninsured people become sick or injured. Cancer also causes a significant negative impact on businesses due to prolonged absences of cancer patients from work.

Although methods of cancer treatment have greatly improved over the years, many challenges, most notably relapse among cancer patients and difficulties in treating patients in advanced stages of cancer as well as with metastatic diseases or with systemic cancers such as leukemia or lymphoma, remain. For example, improved diagnostic methods combined with better surgical techniques allow oncologists to remove tumor with greater confidence, while at the same time minimizing the removal of normal tissue. As such, the recovery time for patients can be decreased and psychological impact is reduced. However, surgery is only one of the few useful tools for treating patients with localized, non-metastatic tumors or the tumors which are minimally spread.

Chemotherapy is another treatment of choice for certain types of cancers. However, chemotherapeutic methods are generally not specific for tumor cells as compared to normal cells. As a result, chemotherapy is generally associated with serious side effects and can be particularly devastating to the patient's immune system and to rapidly dividing tissues, such as tissues in liver, kidneys, gut, and epithelium.

Cancer progression is dependent on angiogenesis, or the sprouting of new blood vessels that penetrate every solid tumor. The rapid tissue proliferation which defines cancer results in a number of adaptive cellular responses, primary among which are the distinct but related processes of angiogenesis and increased glycolysis. Angiogenesis is primarily driven by several mitogenic factors such as vascular endothelial growth factor (VEGF) and its receptors play a key role. While neovascularization is essential in embryonic development, it is highly undesirable in cancers because these nascent vessels infuse tumor tissue and provide them with increased oxygenation and nutrient content for more rapid growth. Angiogenesis is particularly pernicious because it poses a double threat: not only it accelerates tumor growth, but also provides a gateway to metastasis via the newly formed vasculature. As it is metastatic growth which exerts the greatest impact on overall patient survival, angiogenesis represents a critical chemotherapeutic target. Moreover, vascular targets should not engender resistance to therapy because they are not subject to the multiple mutations which occur in malignant cells. One of the primary advantages of targeting the blood supply (vasculature) is that, unlike cells in the cancerous tissues, the cells that comprise blood vessels are genetically stable and, therefore, should have diminished resistance to therapy.

As tumor cells continue to proliferate, they are forced farther away from the blood supply carrying needed oxygen and nutrients for metabolic processes and therefore cannot attain adequate oxygen perfusion. The ensuing hypoxia[1] results in a switch to an anaerobic metabolism which selects for cells with upregulated glycolysis.[2] Enhanced glycolytic function then leads to increased generation of lactic acid which lowers intracellular pH and can facilitate the degradation of the extracellular matrix and basement membrane, thereby promoting angiogenesis.[3] Glycolysis confers a significant advantage in overcoming growth restraints during tumorigenesis[4,5] and most primary metastatic tumors demonstrate significant upregulation of glycolytic enzymes like hexokinases 1 and 2 and glucose transporters GLUT1 and GLUT3.[6]

Hypoxia is one of the most important hallmarks of solid tumors that plays a vital role in cell proliferation, signaling and growth.[7] A typical neoplasm is usually devoid of blood vessels in its early stage. The rapidly proliferating cells contribute to development of hypoxia.[8] Despite the fact that cell proliferation decreases in those parts of a tumor that are away from blood vessels,[9] they tend to select for more aggressive cellular phenotypes. Moreover, it has been reported that the hypoxic tissue away from the blood vessels give rise to cells that have lost sensitivity to p53-mediated apoptosis.[7]

Hypoxia also leads to upregulation of genes involved in drug resistance, such as P-glycoproteins[10,11] in addition to the fact that lack of adequate blood supply to hypoxic cells severely impairs the delivery of drug to these cells.[12,13] Most importantly, from a transcriptional standpoint, hypoxia results in an upregulation of genes involved in angiogenesis[14] and tumor invasion[15] resulting in more aggressive cancer phenotype.[16]

In cells and tissues, response to hypoxia is primarily mediated by the family of hypoxia-inducible transcription factors, among which hypoxia-inducible factor 1 (HIF1) plays a major role. It is a heterodimeric transcription factor which mediates regulation of many key genes upregulated in a hypoxic state (FIG. 1a).[17] During normoxic conditions, the a-subunit of HIF1 is regulated by hydroxylation at proline residues 402 and 564;[18] these modifications serve as a docking site for the von Hippel-Lindau (pVHL) protein[19] to bind HIF1 and tag it with ubiquitin for subsequent proteasomal degradation.[20] However, under hypoxic conditions, HIF1α accumulates, enters the nucleus and dimerizes with its beta subunit, aryl hydrocarbon receptor nuclear translocator (ARNT, or HIF1β),[21] It binds to the promoter region of hypoxia inducible genes possessing hypoxia-response elements (HREs),[22] including VEGF, c-Met, EPO, and GLUT-1.[23,24] Because low oxygen levels also preclude hydroxylation of another regulatory site at Asn803,[25-30] the coactivator CREB binding protein (CBP)/p300[31-33] is recruited via binding the C-terminal domain of HIF1α and promotes elevated expression levels of hypoxia-inducible genes (FIG. 1b).[34-36] In many tumor cells where oncogenic mutations in RAS, SRC and HER2/NEU/ERBB2 are found, high levels of HIF1α have been detected even under well-oxygenated condition.[37]

It has been shown that antisense construct of HIF1α eradicates in vivo a small transplanted thymic lymphoma and even increases the efficacy of immunotherapy against larger tumors.[38] Small molecule inhibitors of microtubules, such as 2-methoxyestradiol, vincristine and paclitaxel have been shown to reduce HIF1α levels in vitro and also reduce tumor growth and vascularization.[39] However, it is not clearly understood whether the effects shown in tumor growth reduction is due to microtubule inhibition or reduction of HIF1α levels.

HIF1 interacts primarily with the $CH_1$ domain of CBP/300 through a series of key cysteine residues and this interaction is driven by hydrophobic forces. It was shown that the natural product chetomin (FIG. 2, vide infra), a fungal metabolite of the *Chaetomium* sp., demonstrated potent and specific inhibition of the HIF/p300 complex. Because p300/CBP is absolutely required for HIF1-mediated transactivation, blocking the association of HIF1 and p300/CBP effectively downregulates transcription.

SUMMARY OF THE INVENTION

One embodiment of the present invention is directed to compounds according to Formula I, including salts, solvates and hydrates thereof:

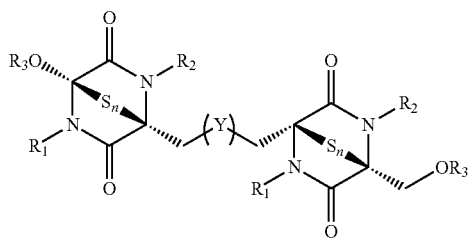

Formula I where n=1, 2, 3, 4;
$R_1$, and $R_2$ are independently selected from the group consisting of hydrogen, alkyl, substituted alkyl, and aryl;
$R_3$ is selected from the group consisting of H, and acyl
Y is selected from the group consisting of $(CH_2)_k$, $(—CH_2—CH_2—O—)_l$, $(—CH_2—CH_2—NH—)_m$, $(—CH_2—CH_2—S—)_n$, $(—CH=CH—)_o$, heterocycle,

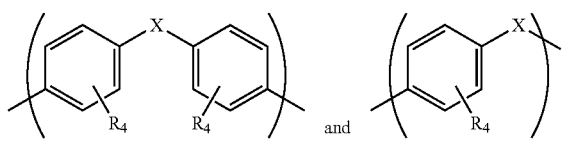

wherein X is selected from the group consisting of $(CH_2)_k$, $(—CH_2—CH_2—O—)_l$, $(—CH_2—CH_2—NH—)_m$, $(—CH_2—CH_2—S—)_n$, $(—CH=CH—)_o$, and heterocycle;

and wherein k, l, and m, n, o are each independently equal to 1, 2, or 3; and
$R_4$ is selected from the group consisting of H, alkyl, and halogen.

In the above embodiment, for $R_1$ and $R_2$, alkyl is preferably methyl or ethyl, substituted alkyl is preferably $—CH_2OH$, and aryl is preferably phenyl or benzyl for $R_3$, acyl is preferably $COCH_3$.

Another embodiment of the present invention is directed to a compound according to Formula II, including salts, solvates and hydrates thereof:

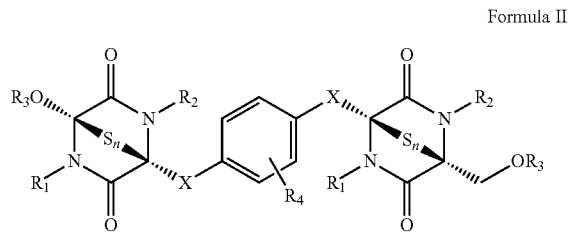

Formula II wherein n=1, 2, 3, 4;
$R_1$, $R_2$ are independently selected from the group consisting of H, alkyl, substituted alkyl, and aryl;
$R_3$ is selected from the group consisting of H, acyl;
X is independently selected from the group consisting of $(CH_2)_k$, $(—CH_2—CH_2—O—)_l$, $(—CH_2—CH_2—NH—)_m$, $(—CH_2—CH_2—S—)_n$, $(—CH=CH—)_o$, and heterocycle, wherein k, l and in, n, o are each independently equal to 1, 2, or 3; and
$R_4$ is selected from the group consisting of H, alkyl, and halogen.

In the above embodiment, for $R_1$ and $R_2$, alkyl is preferably methyl or ethyl, substituted alkyl is preferably $—CH_2OH$, and aryl is preferably phenyl or benzyl; for $R_3$, acyl is preferably $COCH_3$.

Another embodiment of the present invention is directed to a compound according to Formula III, including salts, solvates and hydrates thereof.

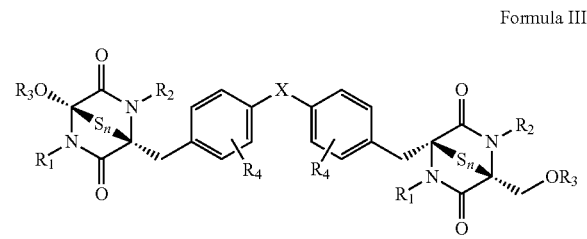

Formula III wherein n=1, 2, 3, 4;
$R_1$, and $R_2$ are independently selected from the group consisting of H, alkyl, substituted alkyl, aryl;
$R_3$=H, or acyl;
X is selected from the group consisting of $(CH_2)_k$, $(—CH_2—CH_2—O—)_l$, $(—CH_2—CH_2—NH—)_m$, $(—CH_2—CH_2—S—)_n$, $(CH=CH—)_o$, and heterocycle, wherein k, l and m, n, o are each independently equal to 1, 2, or 3; and
$R_4$=H, alkyl, or halogen.

In the above embodiment, for $R_1$ and $R_2$, alkyl is preferably methyl or ethyl, substituted alkyl is preferably —CH$_2$OH, and aryl is preferably phenyl or benzyl; for $R_3$, acyl is preferably COCH$_3$.

Another embodiment of the present invention is directed to a pharmaceutical composition comprising at least one compound according to either Formula I, Formula II or Formula III, or a salt, solvent or hydrate thereof, dissolved or dispersed in a carrier.

Another embodiment of the present invention is directed to the following compounds:

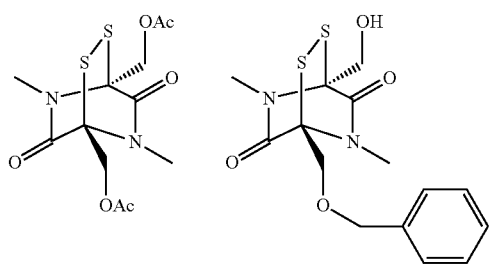

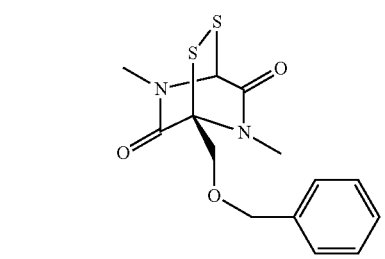

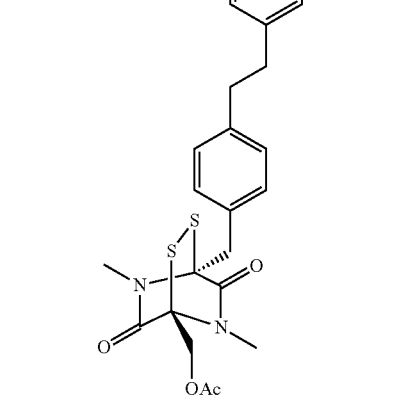

-continued

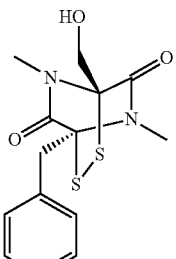

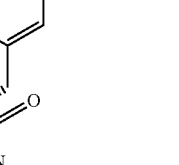

-continued

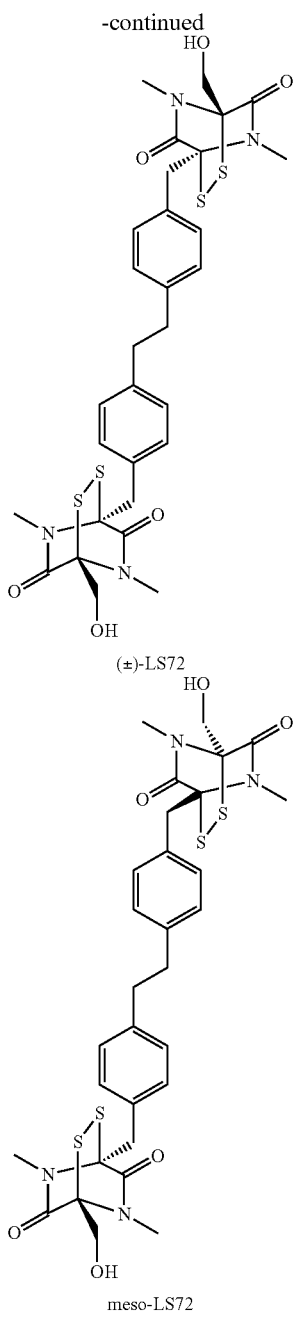

(±)-LS72 meso-LS72

Another embodiment of the present invention is directed to a method for interfering with hypoxia-induced transcriptional pathway. Generally, the method according to this embodiment comprises contacting a cell with at least one compound according to either Formula I, Formula II or Formula III, or a salt, solvent or hydrate thereof.

Another embodiment of the present invention is directed to a method for treating breast cancer comprising administering to a subject in need thereof an effective amount of at least one compound according to either Formula I, Formula II or Formula III, or a salt, solvent or hydrate thereof.

Another embodiment of the present invention is directed to a method for treating carcinoma comprising administering to a subject in need thereof an effective amount of at least one compound according to either Formula I, Formula II or Formula III, or a salt, solvent or hydrate thereof.

Other aspects and advantages of the present invention will become apparent from the following detailed description, the accompanying drawings, and the appended claims.

DETAILED DESCRIPTION

Definition

Figure 1:
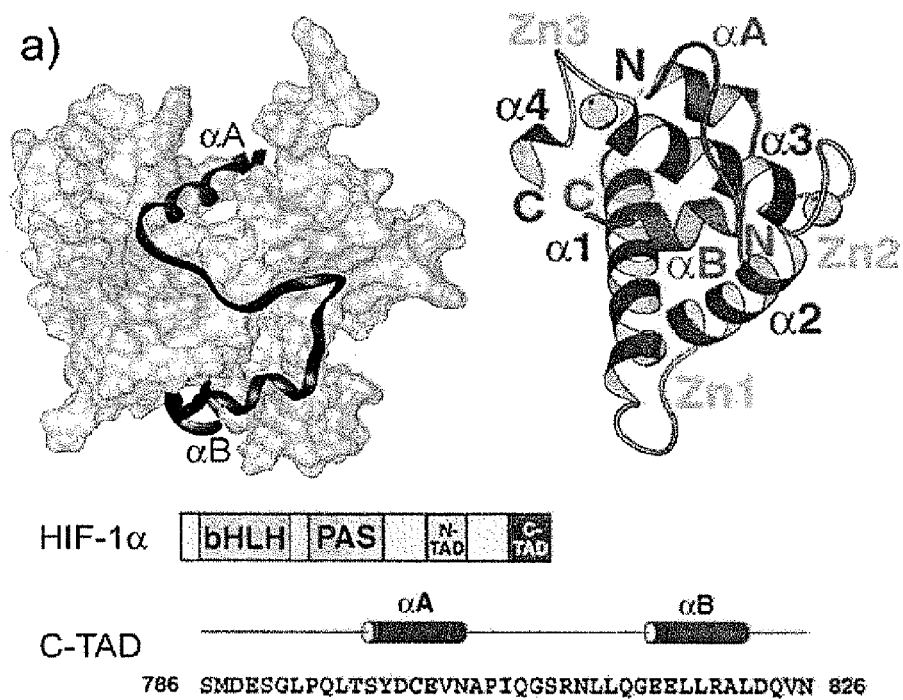
FIG. 1 (a) Structure of the HIF1α C-TAD/p300 $CH_1$ complex, domain map of hypoxia-inducible factor 1α (HIF1α) and sequence of the human HIF1α C-TAD. (b) Schematic illustration of the HIF1α transcriptional pathway.
Figure 1:
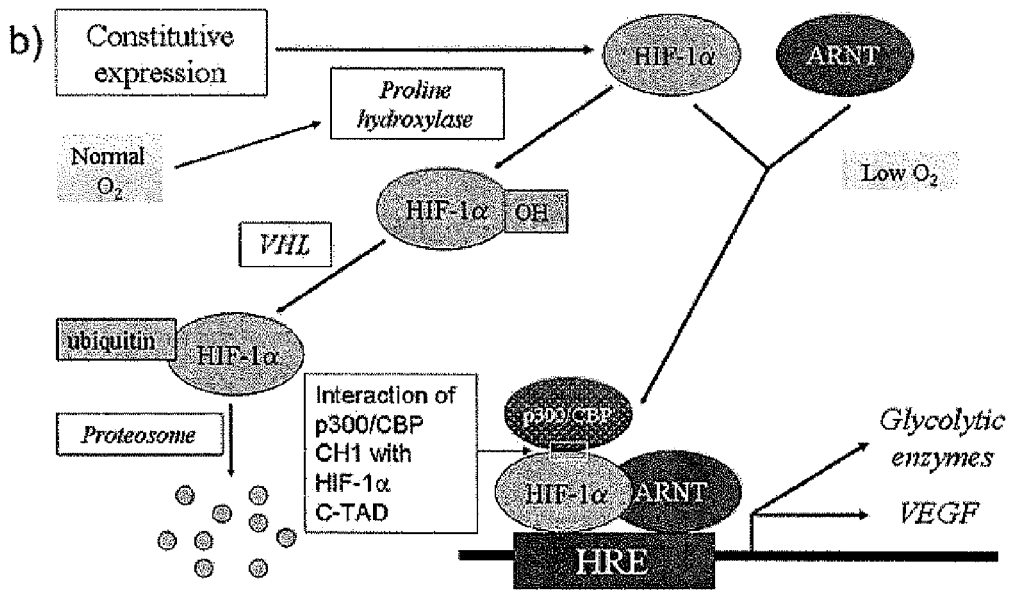

Unless otherwise indicated herein, all terms used herein have the meanings that the terms would have to those skilled in the art of the present invention. Practitioners are particularly directed to current textbooks for definitions and terms of the art. It is to be understood, however, that this invention is not limited to the particular methodology, protocols, and reagents described, as these may vary.

The term "alkyl" refers to a $C_1$-$C_{10}$ straight or branched chain alkyl, for example, methyl, ethyl, n-propyl, i-propyl, n-butyl, i-butyl, sec-butyl, tert-butyl, n-pentyl, i-pentyl, neopentyl, tert-pentyl, and the like.

Substituents for a "substituted alkyl" are hydroxy, alkoxy (e.g., methoxy and ethoxy), mercapto, alkylthio (e.g., methylthio), cycloalkyl (e.g., cyclopropyl, cyclobutyl, cyclopentyl, and cyclohexyl), halogen (e.g., fluoro, chloro, bromo, and iodo), carboxy, alkoxycarbonyl (e.g., methoxycarbonyl and ethoxycarbonyl), nitro, cyano, haloalkyl (e.g., trifluoromethyl), alcohol, substituted or unsubstituted amino (e.g., methylamino, dimethylamino, and carbamoylamino), guanidine, phenyl, benzyloxy, and the like. These substituents are able to bind them at one or more of any possible positions.

The term "aryl" refers to a monocyclic or condensed ring aromatic hydrocarbons. Examples of the aryl are phenyl, naphthyl, and the like.

The term "heterocycle" refers to an aromatic heterocyclic group which contains one or more hetero atoms selected from the group consisting of nitrogen, oxygen and sulfur atoms in the ring and may be fused with a carbocyclic ring or other heterocyclic ring at any possible position.

The term "acyl" refers to an alkylcarbonyl, cycloalkylcarbonyl, arylcarbonyl, heterocyclylcarbonyl, or heteroarylcarbonyl substituent, any of which can be further substituted, e.g., by one or more substituents.

The term "halogen", alone or in combination, signifies fluorine, chlorine, bromine or iodine and preferably fluorine, chlorine or bromine.

One embodiment of the present invention is directed to compound according to Formula I, including salts, solvates and hydrates thereof,

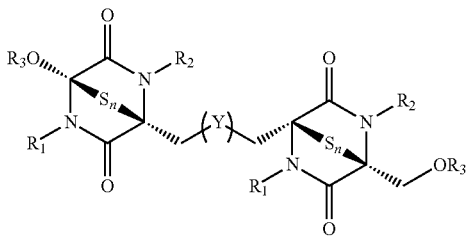

Formula I where n=1, 2, 3, 4;
the distance between the centers of each diketopiperazine ring is between 4-32 Angstroms;
the preferred distance between the centers of each diketopiperazine ring is between 10-22 Angstroms;
$R_1$, and $R_2$ are independently selected from the group consisting of hydrogen, alkyl, substituted alkyl, and aryl;
$R_3$ is selected from the group consisting of H, and acyl;
Y is selected from the group consisting of $(CH_2)_k$, $(-CH_2-CH_2-O-)_l$, $(-CH_2-CH_2-NH-)_m$, $(-CH_2-CH_2-S-)_n$, $(-CH=CH-)_o$, heterocycle,

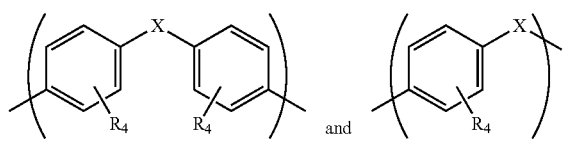

wherein X is selected from the group consisting of $(CH_2)_k$, $(-CH_2-CH_2-O-)_l$, $(-CH_2-CH_2-NH-)_m$, $(-CH_2-CH_2-S-)_n$, $(-CH=CH-)_o$, and heterocycle, and wherein k, l, m, n, o are each independently equal to 1, 2, or 3; and
$R_4$ is independently selected from the group consisting of H, alkyl, and halogen.

In the above embodiment, for $R_1$ and $R_2$, alkyl is preferably methyl or ethyl, substituted alkyl is preferably $-CH_2OH$, and aryl is preferably phenyl or benzyl; for $R_3$, acyl is preferably $COCH_3$.

Another embodiment of the present invention is directed to a compound according to Formula II, including salts, solvates and hydrates thereof:

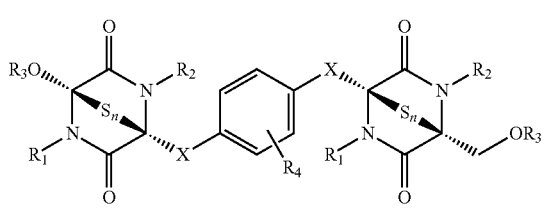

Formula II wherein n=1, 2, 3;
$R_1$, $R_2$ are independently selected from the group consisting of H, alkyl, substituted alkyl, and aryl;
$R_3$ is selected from the group consisting of H, and acyl;
X is independently selected from the group consisting of $(CH_2)_k$, $(-CH_2-CH_2-O-)_l$, $(-CH_2-CH_2-NH-)_m$, $(-CH_2-CH_2-S-)_n$, $(-CH=CH-)_o$, and heterocycle, wherein k, l, m, n, o are each independently equal to 1, 2, or 3; and
$R_4$ is independently selected from the group consisting of H, alkyl, and halogen.

In the above embodiment, for $R_1$ and $R_2$, alkyl is preferably methyl or ethyl, substituted alkyl is preferably $-CH_2OH$, and aryl is preferably phenyl or benzyl; for $R_3$, acyl is preferably $COCH_3$.

Another embodiment of the present invention is directed to a compound according to Formula III, including salts, solvates and hydrates thereof:

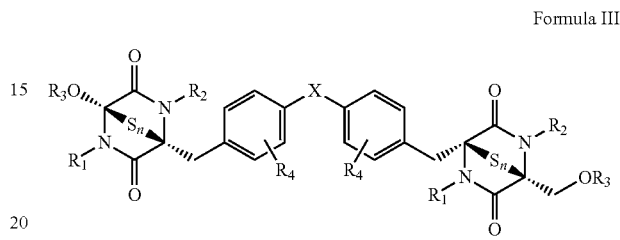

Formula III wherein n=1, 2, 3;
$R_1$, and $R_2$ are independently selected from the group consisting of H, alkyl, substituted alkyl, aryl;
$R_3$=H, or acyl;
X=$(CH_2)_k$, $(-CH_2-CH_2-O-)_l$, $(-CH_2-CH_2-NH-)_m$, $(-CH_2-CH_2-S-)_n$, $(-CH=CH-)_o$, heterocycle, wherein k, l, m, n, o are each independently equal to 1, 2, or 3; and
$R_4$ is independently selected from H, alkyl, and halogen.

In the above embodiment, for $R_1$ and $R_2$, alkyl is preferably methyl or ethyl, substituted alkyl is preferably $-CH_2OH$, and aryl is preferably phenyl or benzyl; for $R_3$, acyl is preferably $COCH_3$.

In Formulas the preferred heterocyles are Indoles, substituted benzenes (i.e. fluorophenyls etc.). Also in Formulas I-III, the $R_4$ is indicated as a variable attachment to the aromatic ring and indicates that $R_4$ may be mono-, di-, tri- or tetra-substituted on the aromatic ring and $R_4$ may be independently selected at each substitution site.

Another embodiment of the present invention is directed to a pharmaceutical composition comprising at least one compound according to either Formula I, Formula II or Formula III, or a salt, solvent or hydrate thereof, dissolved or dispersed in a carrier.

Another embodiment of the present invention is directed to a method for interfering with hypoxia-induced transcriptional pathway. Generally, the method according to this embodiment comprises contacting a cell with at least one compound according to either Formula I, Formula II or Formula III, or a salt, solvent or hydrate thereof.

Another embodiment of the present invention is directed to a method for treating breast cancer comprising administering to a subject in need thereof an effective amount of at least one compound according to either Formula I, Formula II or Formula III, or a salt, solvent or hydrate thereof.

Another embodiment of the present invention is directed to a method for treating carcinoma comprising administering to a subject in need thereof an effective amount of at least one compound according to either Formula I, Formula II or Formula III, or a salt, solvent or hydrate thereof.

Synthetic Epidithiodiketopiperazines as Inhibitors of Hypoxia-Inducible Transcription The presence of two a-helical regions in the contact between HIF1α c-terminal activation domain (C-TAD) and p300/CBP cysteine-histidine rich region 1 (CH$_1$) (FIG. 1a)

opens a possibility for designing of synthetic transcriptional antagonists that could predictably modulate this interaction. However, peptides composed of less than 15 amino acid residues do not generally form α-helical structures at physiological conditions once excised from the protein environment. Notably, the only attempt of disruption of C-TAD/CH$_1$ interaction with the a-helix was an approach reported by Kung et al.[40] In this study, C-TAD was expressed as a fusion protein with Gal4 which stabilized the domain. The resulting protein suppressed transcription of hypoxia-inducible genes and had an inhibitory effect on the growth of modified human tumor cells in nude mice xenograft models. However, difficulties with systemic delivery and complications arising from the use of retroviruses in cells and tissues hamper their widespread adaptation.

Because interaction of HIF1α C-TAD with transcriptional co-activator p300/CBP is a point of significant amplification of biological response, its disruption with designed protein ligands could be an effective means of suppressing aerobic glycolysis and angiogenesis in cancers.[41-43] Although the contact surface of the HIF1α C-TAD with p300/CBP is extensive (3393 Å$^2$), the inhibition of this protein-protein interaction by direct interactions is difficult. Instead, the induction of a structural change to one of the binding partners (p300/CBP) may be sufficient to disrupt the complex.[44] The opposite strategy has already been demonstrated, in which function of the protein p53 has been restored by a small molecule.[45].

A method for interfering with hypoxia-induced transcriptional pathway is provided by the present invention. Generally, the method involves contacting a cell with any of the compounds of Formulas I-III, Examples of small molecules representing structures above as well as methods for designing ETPs for therapeutic applications are discussed below.

EXAMPLES

Figure 2:
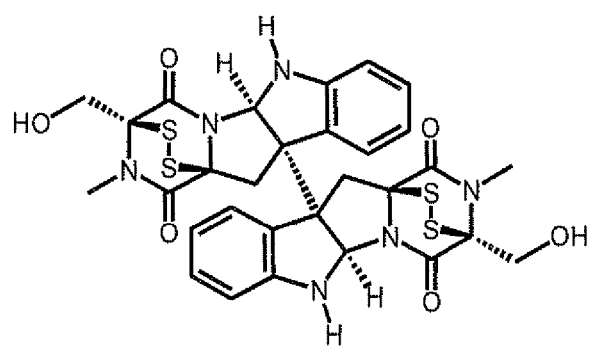
FIG. 2 Chaetocin CTC, isolated from *Chaetomium globosum* and chetomin CTM, from *Chaetomium cocliodes*.
Figure 2:
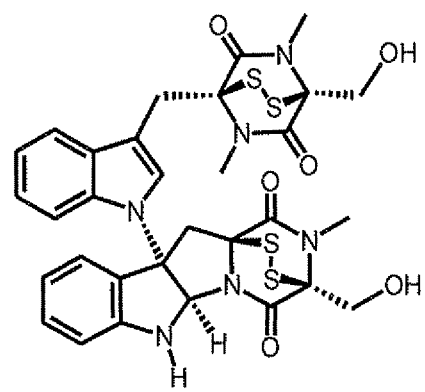

Design and Synthesis of Dimeric Epidithiodiketopiperazines Targeting Hypoxia-Inducible Transcription Factor Complex Structural Basis in the Design of Synthetic Dimeric Epidithiodiketopiperazines Although inhibition of nuclear protein-protein interactions with small molecules in the past has proven to be difficult,[46] recent screens for high-affinity protein ligands have resulted in several remarkable accomplishments.[44,47-53] Two small molecules, chaetocin (CTC),[54] and chetomin (CTM),[55] (FIG. 2), have been shown to inhibit the interaction between HIF1□ C-TAD and p300/CBP and to attenuate hypoxia-inducible transcription, although the exact mechanism of its action remains unclear.[44] Despite the initial encouraging reports, further design of inhibitors of HIF1 pathway is needed, because both compounds induced coagulative necrosis, anemia and leukocytosis in experimental animals.

Chaetocin and chetomin are two epidithiodiketopiperazine[56] (ETP) metabolites from the filamentous fungi of the Chaetomium species that have been previously characterized as having antimicrobial activity.[57,58] Total synthesis of these natural products has been very challenging and for chetomin has not been reported to date, presumably due to the lack of methods for enantioselective sulfenylation of the diketopiperazine rings and the instability of the disulfide bridge toward bases and reducing agents. Under physiological conditions, the bridged disulfide moiety can exist either in disulfide or dithiol forms and is thought to be essential for biological activity of this class of natural products. This hypothesis is supported by our preliminary results and by the recent work of Bernardo and Waring who have shown that only the natural (oxidized) form of epidithiodiketopiperazine is then reduced actively concentrated in live cells in a glutathione-dependent manner.[59] Intracellular levels of the ETP can be up to 1500-fold greater than the applied concentration, and ETP in the cells exists almost exclusively in the reduced form.[59]

We hypothesized that two properly positioned redox-active ETP rings in chaetocin and chetomin may play an important role in high affinity bidentate binding of these compounds to cysteine-histidine rich, $Zn^{2+}$-dependent protein domains. The rigidity of the structures of CTC and CTM makes it easier to predict their biologically active conformations. Despite the marked difference in structure of the central scaffold, the two molecules assume low energy conformations with very similar orientations of the ETP rings.

Figure 3:
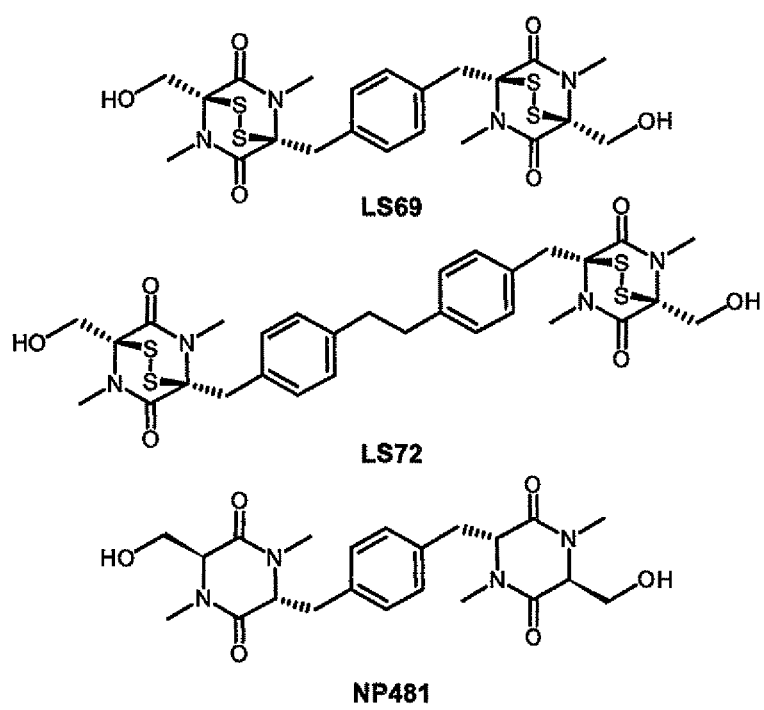
FIG. 3 Structures of synthetic epidithiodiketopiperazines LS69, LS72 and control diketopiperazine NP481.

The synthetic dimeric epidithiodiketopiperazines were designed by connecting the two ETP rings via a semi-rigid central scaffold. Such small molecules may be capable of disrupting the global fold and, as a result, the recruitment of p300/CBP by the HIF1alpha. To confirm this, we designed ETPs LS69 and LS72 where the positioning of the ETP rings is similar to chetomin and examined their effect on transcription of HIF-inducible genes (FIG. 3). A molecule structurally similar to LS69 that is lacking the disulfide bridges, NP481, was also designed and used as a control compound (FIG. 3).

Synthesis of Dimeric Epidithiodiketopiperazines

In our synthetic plan, we formed the disulfide bridge in synthetic intermediates at the latest possible stage. We introduce the protected disulfide at an early stage, with the hope that the stability of the protected disulfide group would improve and consequently facilitate the synthesis.[60] The disulfide bridge could then be regenerated at a later stage.

Figure 4:
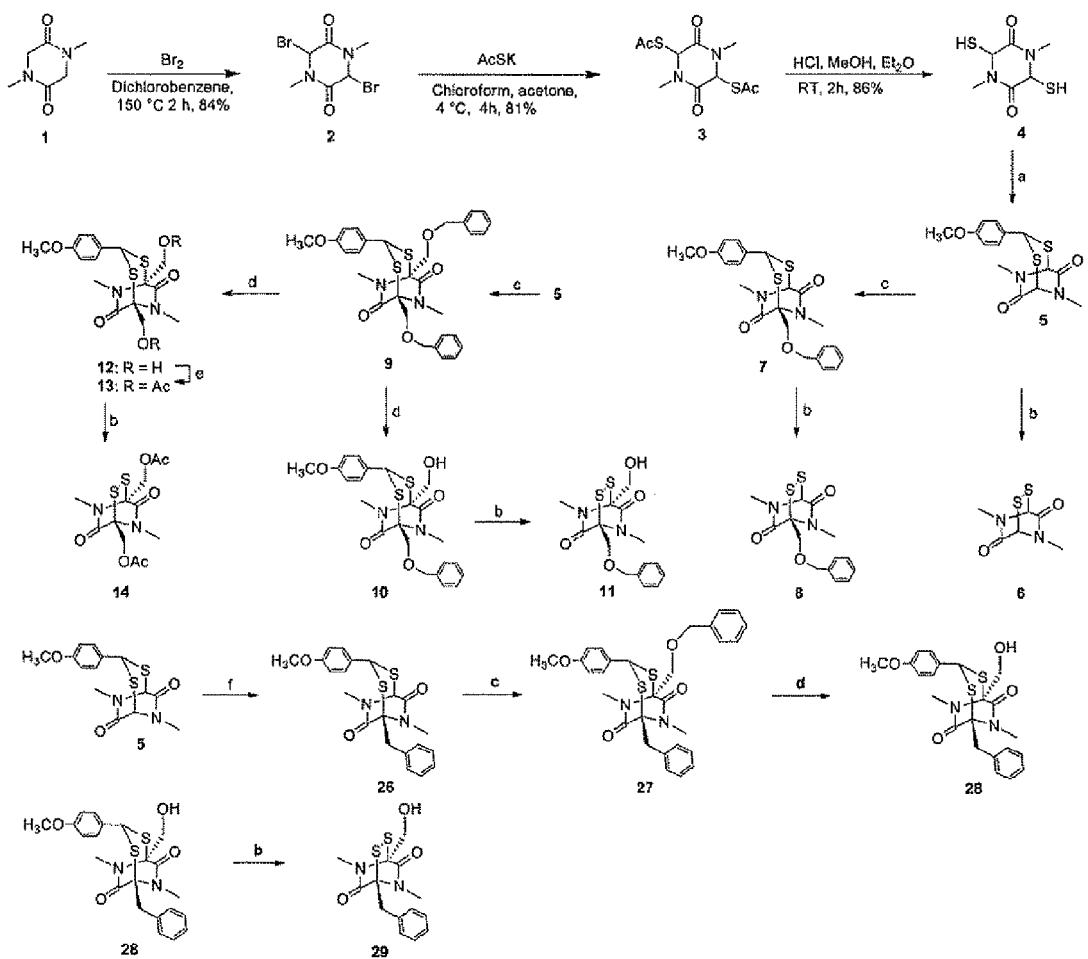
FIG. 4 shows the synthesis of bicyclic thioacetals and single-ring ETPs under the following conditions: a: p-Anisaldehyde, $BF_3$, $ET_2O$, DCM, RT, 16 hr, 92%; b: mCPBA, $Me_2S$, $HClO_4$; c: BOMCl, nBuLi, THF, −78° C., d: $BCL_3$, $CH_2Cl_2$; e: AcCl, pyridine, $CH_2Cl_2$; f: nBuLi, THF, −78° C., BnCl.

Our synthetic plan involved three key transformations (FIGS. 4 and 5): i) protection of the disulfide bridge as a bicyclic thioacetal, functionalization of the C-3 and C-6 positions of the thioacetal ring via carbanion chemistry, and regeneration of the disulfide bridge. Bromination of the commercially available 1,4-dimethyl-2,5-piperazinedione 1 followed by reaction of 2 with potassium thioacetate and subsequent removal of the acetyl group in 3 under acidic conditions provided a mixture of cis- and trans-dithiols 4 in good overall yield (FIG. 4). The thioacetal 5 was obtained via a reaction of dithiols with p-anisaldehyde and boron trifluoride etherate in high yield. The formation of thioacetal is known to proceed from both cis- and trans-isomers of dithiol.[60] Regioselective deprotonation of 5 with a strong base at the bridgehead positions[61] and subsequent reaction with benzyloxymethyl chloride (BOM chloride) afforded monosubstituted thioacetal 7 in good yield. Likewise, reaction of 5 with 2 equivalents of a strong base, followed by addition of two equivalents of BOM chloride provided compound 9. Regioselective removal of a single benzyl group in 9 could be carried out with one equivalent of boron trichloride, resulting in the formation of alcohol 10. Both benzyl groups could be removed by treating 9 with two equivalents of boron trichloride, resulting in a formation of a diol 12, which was acetylated to give diacetate 13. Regeneration of the disulfide bridge in thioacetals 7, 10 and 13 resulted in the formation of the single-ring ETP compounds 8, 11 (LS75) and 14, respectively. All products were purified by preparative reverse-phase HPLC and their identity and purity was confirmed by NMR and mass spectrometry.

Figure 5:
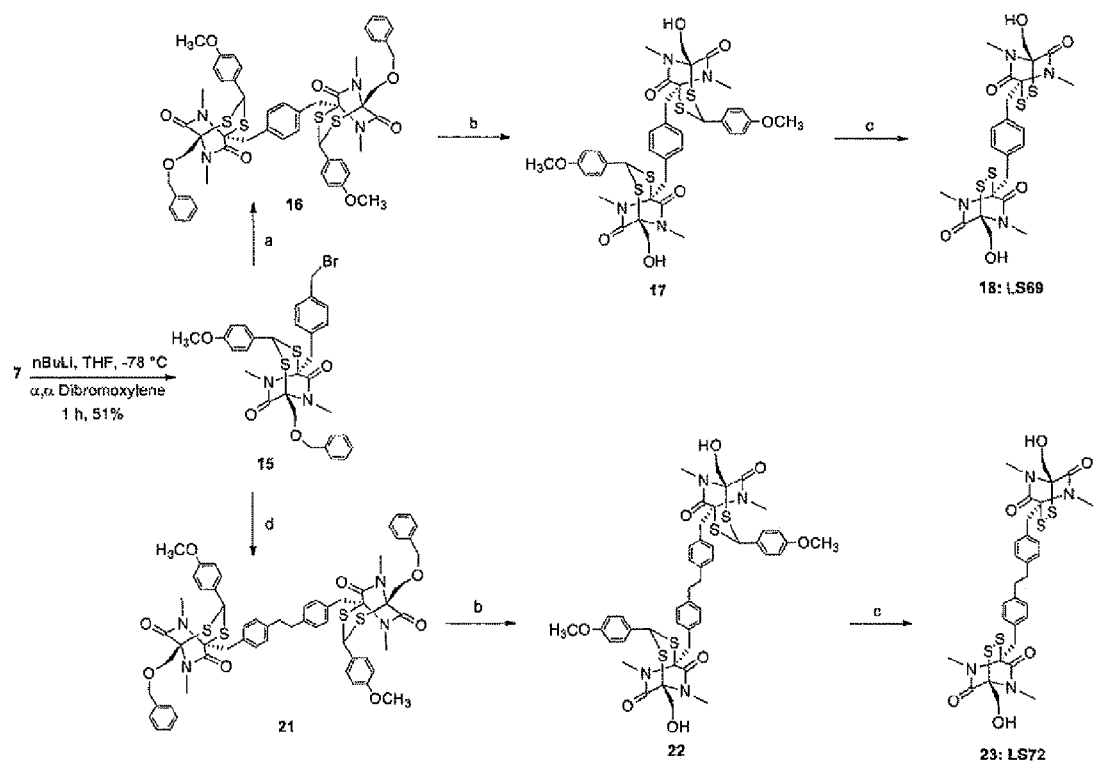
FIG. 5 shows the synthesis of bridged ETPs under the following conditions: a: 7, nBuLi, THF, −78° C.; b: $BCl_3$, $CH_2Cl_2$; c: mCPBA; $Me_2S$, $HClO_4$; d: nBuLi, THF, −78° C.

Preparation of the bridged thioacetal dimers is outlined in FIG. 5. Deprotonation of the bridgehead position in thioacetal 7 with strong base, followed by reaction with excess of α,α-dibromo-p-xylene produced intermediate 15 which was converted into thioacetal dimers 16 and 21 by reaction with second equivalent of the carbanion generated from 7. Removal of the benzyl protecting group was accomplished by treating 16 or 21 with boron trichloride. The conversion of the protected thioacetals into bridged ETP was carried out as follows: oxidation with m-chloroperbenzoic acid resulted in the formation of monosulfoxides which were converted in situ to the ETP by treatment with 70% perchloric acid in THF. The products 19 (LS69) and 24 (LS72) were purified by preparative TLC or by reverse phase HPLC using 5-95% gradient of acetonitrile and water with 0.05% trifluoroacetic acid (TFA), To facilitate characterization, the alcohols 19 and 24 were also acetylated to produce diacetyl derivatives 20 and 26.

To compare the biological effects of the ETPs and demonstrate importance of the disulfide bridge, a xylylene-bridged bis(1,4-piperazine-2,5-dione, DKP) NP481 was also synthesized. This compound is structurally similar to ETP LS69, but it is lacking the disulfide bridge. The activities of the synthetic ETPs could be directly compared with the activity of the DKP compound in cell culture.

Results

LS69 and LS72 Bind $CH_1$ Domain of p300

Prior to undertaking more rigorous biophysical and biological characterization of dimeric ETPs LS69 and LS72, it was important to first characterize its thermodynamic binding properties toward the target, p300 $CH_1$ domain. We conducted SPR experiments in the presence of DTT to mimic the reducing environment that would be found in the intracellular milieu. From the SPR sensorgrams it is clear that both LS69 and LS72 bind directly to the GST-tagged $CH_1$ domain of human p300 (aa residues 323-423) with high affinity.

For LS69, we determined the rate of association ($k_a$) to be $6.97 \times 10^3 \pm 0.157$ $M^{-1}s^{-1}$ and rate of dissociation $k_d$ obtained for LS69 in the wash step following the association step was $1.33 \times 10^{-2} \pm 1.72 \times 10^{-4}$ $s^{-1}$. Therefore the binding constant measured by SPR analysis for LS69 binding to $CH_1$ domain of p300 was "off rate"/"on rate" which gives a value of $K_D = 1.09$ µM.

For LS72, the rate of association $k_a$ obtained by SPR analysis was $4.25 \times 10^3 \pm 85.8$ while in the following wash step the rate of dissociation $k_d$ obtained was 1.54 f $0.14 \times 10^{-2}$ $s^{-1}$. Thus the binding constant obtained for LS72 is $K_D = 3.62$ µM. Based on these data, both LS69 and LS72 reversibly bind to p300-CH1-GST and exhibit a rapid on-rate and a slow off-rate with gradual dissociation from the protein immobilized on the chip surface. Control DKP NP481 did not bind at any concentration tested up to $5.0 \times 10^{\prime 5}$ M (data not shown).

Designed ETPs Downregulate Hypoxia-inducible Promoter Activity

We first examined the effect of designed ETPs on activation of the HIF1 inducible promoters. We used MDA-MB-231 breast cancer cell line that contains chromosomally integrated vector constructs with five copies of hypoxia-responsive element (HRE) derived from the 5'-untranslated region (UTR) of the human VEGF gene.[62] They showed excellent transcriptional activation at low oxygen tension relevant to tumor hypoxia.[63] These cell lines were used in our luciferase reporter assays. In the course of the experiment, cells were incubated with ETPs LS69, LS72, LS75 and DKP compound NP481. In parallel, untreated cells with only vehicle (DMSO) added, were used as controls. Hypoxia conditions were induced by incubating cells with 300 uM desferrioxamine mesylate for 18 h. Cells were harvested, lysed and the levels of luciferase were determined by a luminometer.

Figure 8:
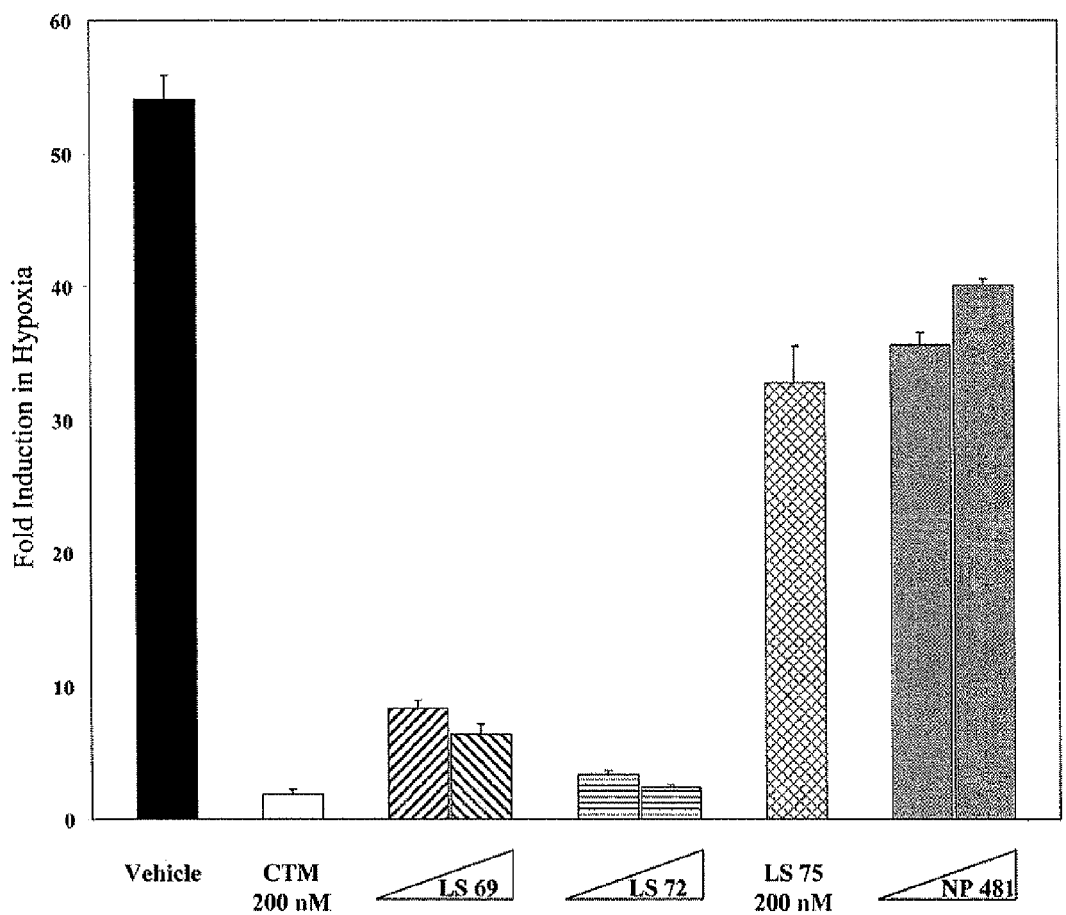
FIG. 8 Analysis of hypoxia-inducible promoter activity with luciferase assays in MDA-MB-231 cell line stably transfected with hRE-hCMV-Luc plasmid. The concentrations of compounds LS69, LS72 and NP481 were 200 nM and 600 nM, respectively.

Results of our measurement are illustrated in FIG. 8 with bar graphs illustrating ratio of induced to uninduced luciferase levels. Without compounds, the levels of expression of the reporter gene increase about 56-fold by placing cells in hypoxia conditions. Treatment of cells with chetomin CTM and synthetic ETP compounds LS69 and LS72 led to significant reduction in hypoxia-inducible promoter activity (FIG. 8). The observed effects were dose-dependent. In contrast, treatment with single-ring ETP LS75 resulted only in a small reduction in promoter activity. Likewise, treatment with the DKP compound NP481 resulted in a minimal reduction of promoter activity and did not show dose dependence.

Inhibition of Hypoxia-Inducible Transcription In Vitro

We used real-time quantitative RT-PCR assays to determine the relative levels of VEGF mRNA in hypoxic cells treated with ETP compounds and control DKP compound. In parallel, cells treated with vehicle were used as controls. mRNA level of β-glucuronidase gene was used as a control in determining the relative levels of transcription.

Figure 9:
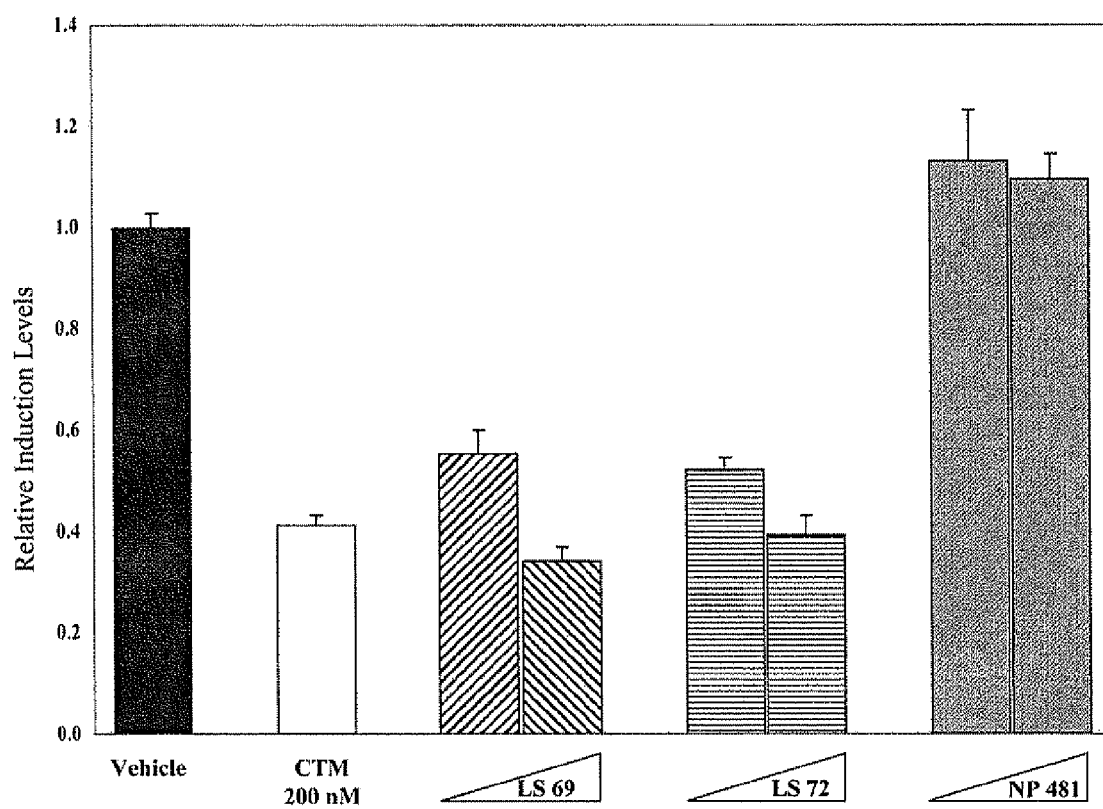
FIG. 9 Relative mRNA levels of the VEGF gene in MCF7 cells as measured by real-time quantitative RT-PCR. The concentrations of compounds LS69, LS72 and NP481 are 200 nM and 600 nM, respectively.

In cultured MCF7 cells under hypoxic conditions, synthetic ETP compounds LS69 and LS72 downregulated VEGF (FIG. 9) gene at levels that are comparable or in certain cases surpass the levels observed with chetomin. Thus, LS69 at 600 nM concentration inhibits VEGF expression by ~65%, which is near the VEGF mRNA levels in the uninduced (normoxic) cells. The observed effects were dose-dependent. The control compound NP481 has shown no inhibitory effect on levels of VEGF.

We also tested the effect of our compounds on the levels of expression of VEGF gene in a different cell line. HeLa cells were selected for this assay. Treatment with 200 nM concentrations of chetomin, LS69 or LS72 resulted in ~50% reduction of the levels of VEGF mRNA.

c-Met gene is another important downstream gene target of hypoxia-inducible transcription factor system. It has five repeats of HRE sequence in its promoter region and Comoglio et al have shown that HRE 4 and HRE 5 are mainly responsible for the hypoxia inducible transcription of c-Met gene. Mutation or deletion of HRE 4 and HRE 5 in the promoter sequence of c-Met gene significantly diminishes the hypoxia inducible induction of its transcription. The mRNA as well as the protein levels of c-Met are significantly upregulated under hypoxia in many cancer cell lines and most of these cancer cell lines are typically metastatic in nature.

Cytotoxicity of LS72 in MCF7 Breast Cancer Cell Line and A549 Lung Epithelial Adenocarcinoma Cell Line One potential issue that arises with the use of ETPs as transcriptional inhibitors is their cytotoxicity. Therefore, careful assessment of the cytotoxicity is crucial for every small molecule that acts as a transcriptional inhibitor in order to rule out non-specific, global effects on transcriptional machinery.

We performed cytotoxicity experiments in order to obtain the $EC_{50}$ values of LS72 in MCF7 breast cancer cell line and A549 lung adenocarcinoma cell line. The goal was to determine the window of viable concentrations and perform our transcription inhibition experiments at concentrations significantly below the $BC_{50}$ values in these cell lines.

Figure 10:
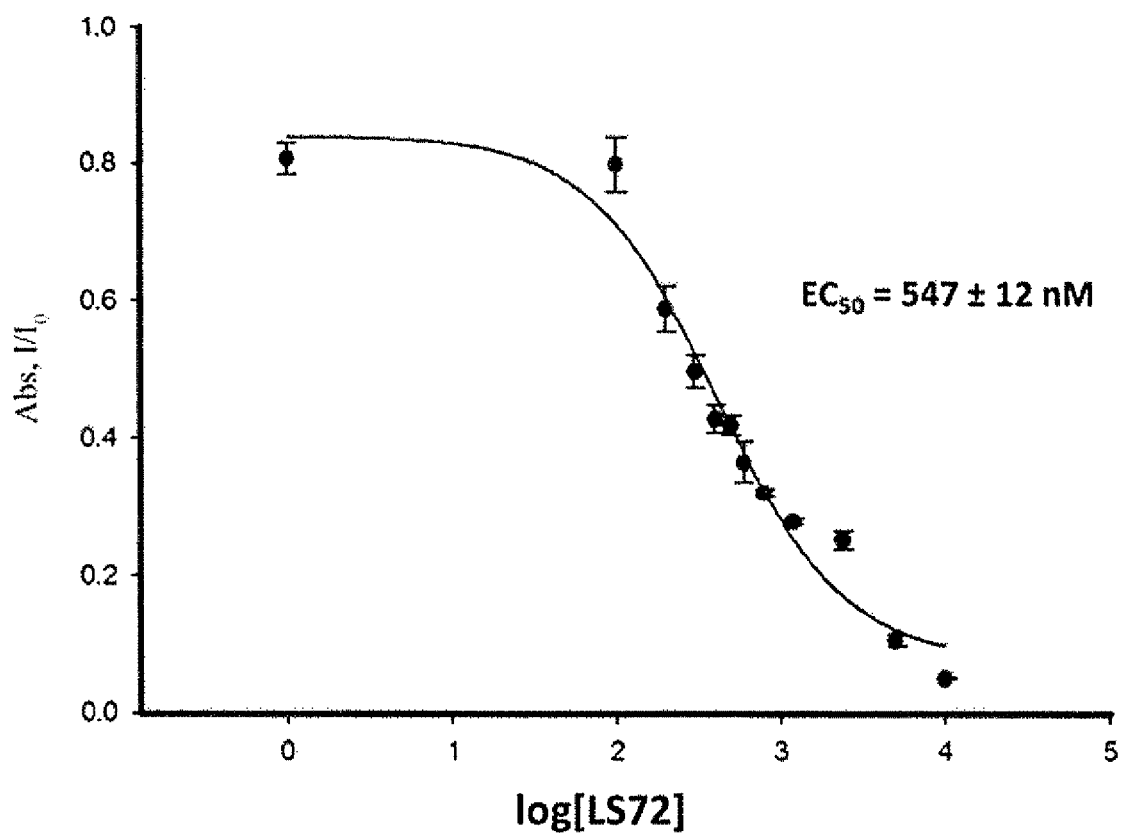
FIG. 10 MTT cytotoxicity assay for LS72 in MCF7 cells. Cells were maintained in RPMI-1640 media supplemented with 10% FBS. Cells were treated with different concentrations of LS72 for 24 hours and the amount of purple formazan formed was determined via spectrophotometry.

In our previous work[64] we reported the $EC_{50}$ value for chetomin in MCF7 cells to be 180 nM. We found the newly designed LS72 to be much less cytotoxic towards MCF7 cells as compared to chetomin. In the MTT cell cytotoxicity assay in MCF7 cells, the EC50 value obtained was 547 nM after 24 h treatment with LS72 (FIG. 10). Based on this EC50 value of LS72 in MCF7 cells we chose to measure its effect on HIF inducible transcription at a maximum concentration of 400 nM in MCF7 cells. This is important in order to minimize the nonspecific effects on mRNA levels due to reduction in cell viability.

Cell line A549 is lung epithelial adenocarcinoma of non-small cell type that is known to exhibit significant upregulation of key HIF1α inducible genes, such as c-Met, VEGF and Glut.' under hypoxic conditions. In our viability assays in this cell line ETPs showed less cytotoxicity as compared to MCF7 cell line. After 24 h treatment with both chetomin and LS72 in Kahn modified F-12 media, an $EC_{50}$ of >10 μM as observed. Therefore the treatment of the cells was extended to 48 h in order to better determine its cytotoxicity.

Figure 11:
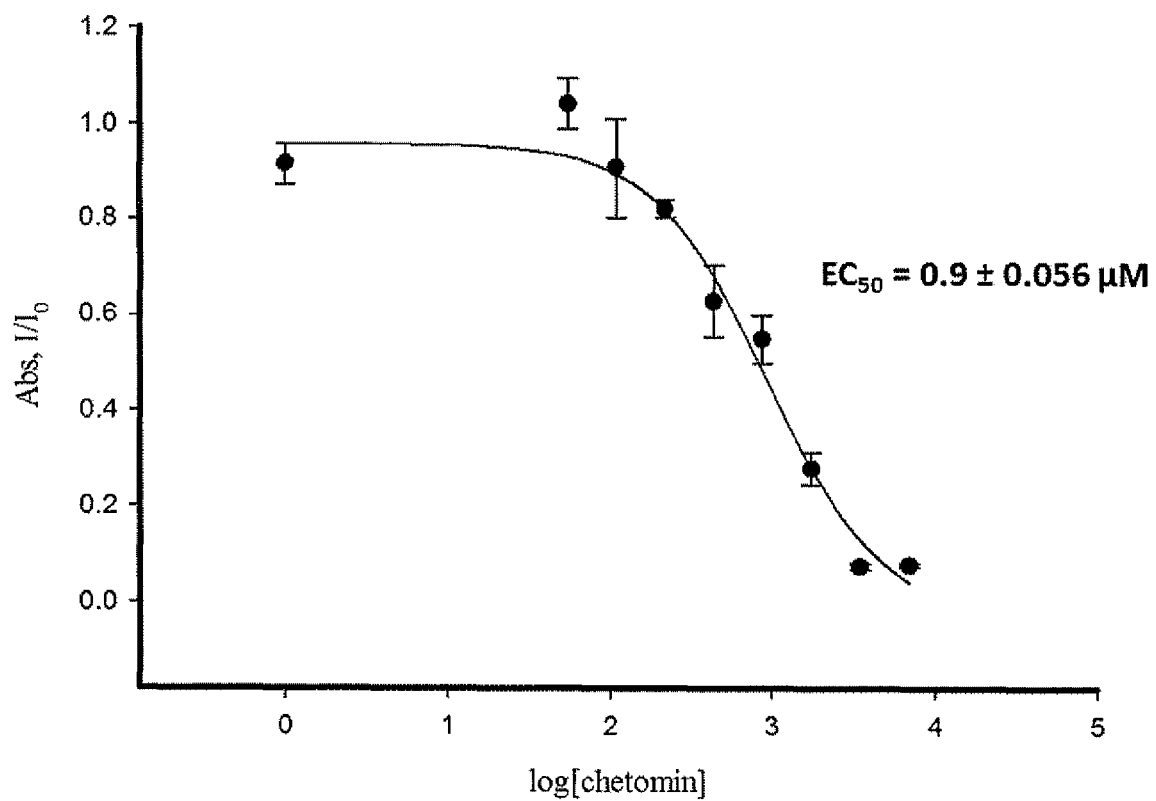
FIG. 11 MTT cytotoxicity assay data for chetomin in A549 cell line. The cells were treated with different concentrations of compound for 48 hours in serum free F-12K medium. The EC50 value obtained for chetomin was 0.9 μM in A549 cell line after treatment for 48 hours. For comparison, treatment of MCF7 cell line for 24 hours with chetomin gave EC50 of 0.2 μM, indicating significantly higher cytotoxicity of the compound in that cell line.
Figure 12:
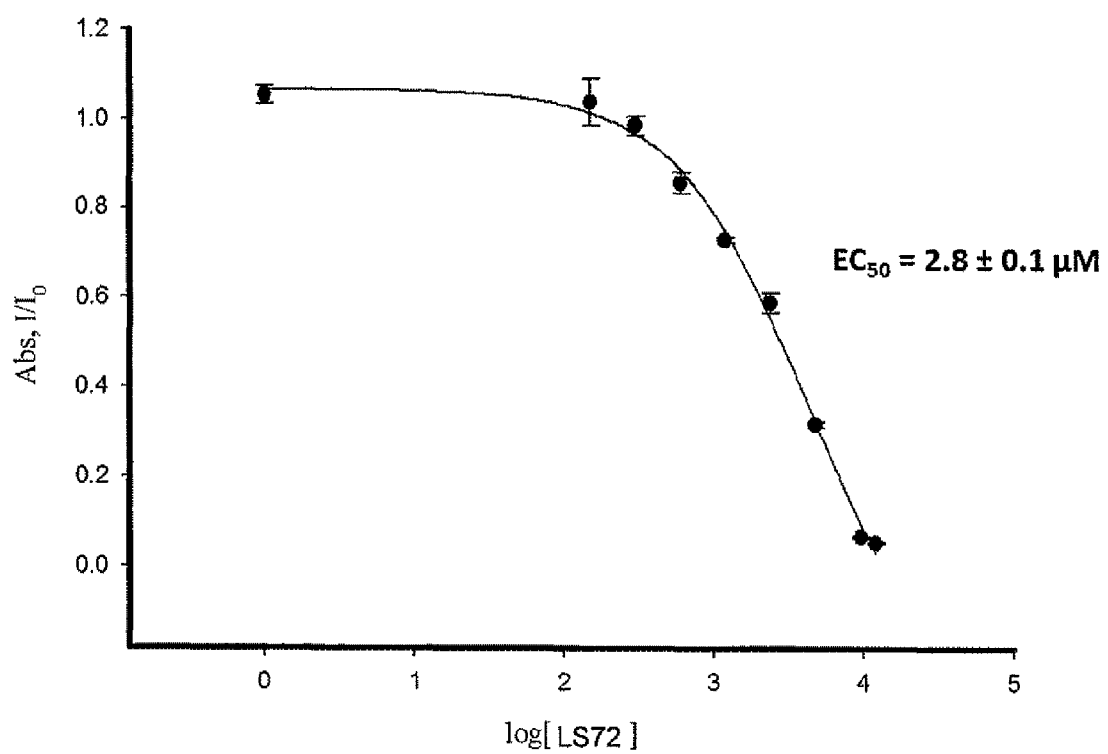
FIG. 12 MTT cytotoxicity assay data for LS72 in A549 cell line. The cells were treated with different concentrations of compound for 48 hours in serum free F-12K medium.

MTT cytotoxicity assay was carried out for chetomin and LS72 in A549 cell line for 48 h. The $EC_{50}$ for LS72 obtained from this assay after 48 h treatment was 2.8 μM (FIGS. 11-12). This value is about five times higher than the EC50 value obtained in MCF7 cell line after 24 h treatment. These data suggest that A549 cell line is much more robust toward treatment as compared to MCF7 cell line. In addition, LS72 is clearly much less toxic to cells as compared to chetomin. Since ETP motifs are common in both LS72 and chetomin, we could only speculate that higher toxicity of chetomin may be due to its cyclotryptophan motif, that is absent in LS72.

Modulation of HIF1α Inducible Transcription with LS72 in A549 Lung Adenocarcinoma Line Finding of a good in vitro model that consistently displays high transcriptional activation of hypoxia-inducible genes turned out to be a challenging task. After evaluating several cell lines we focused our attention on A549 cells, a non-small cell lung adenocarcinoma cell line. It has been reported that A549 cell line produces robust upregulation of key HIF-inducible genes under hypoxia conditions. Specifically, Comoglio et al.[15] reported that under hypoxia c-Met mRNA level is significantly upregulated in A549 cell line.

Figure 13:
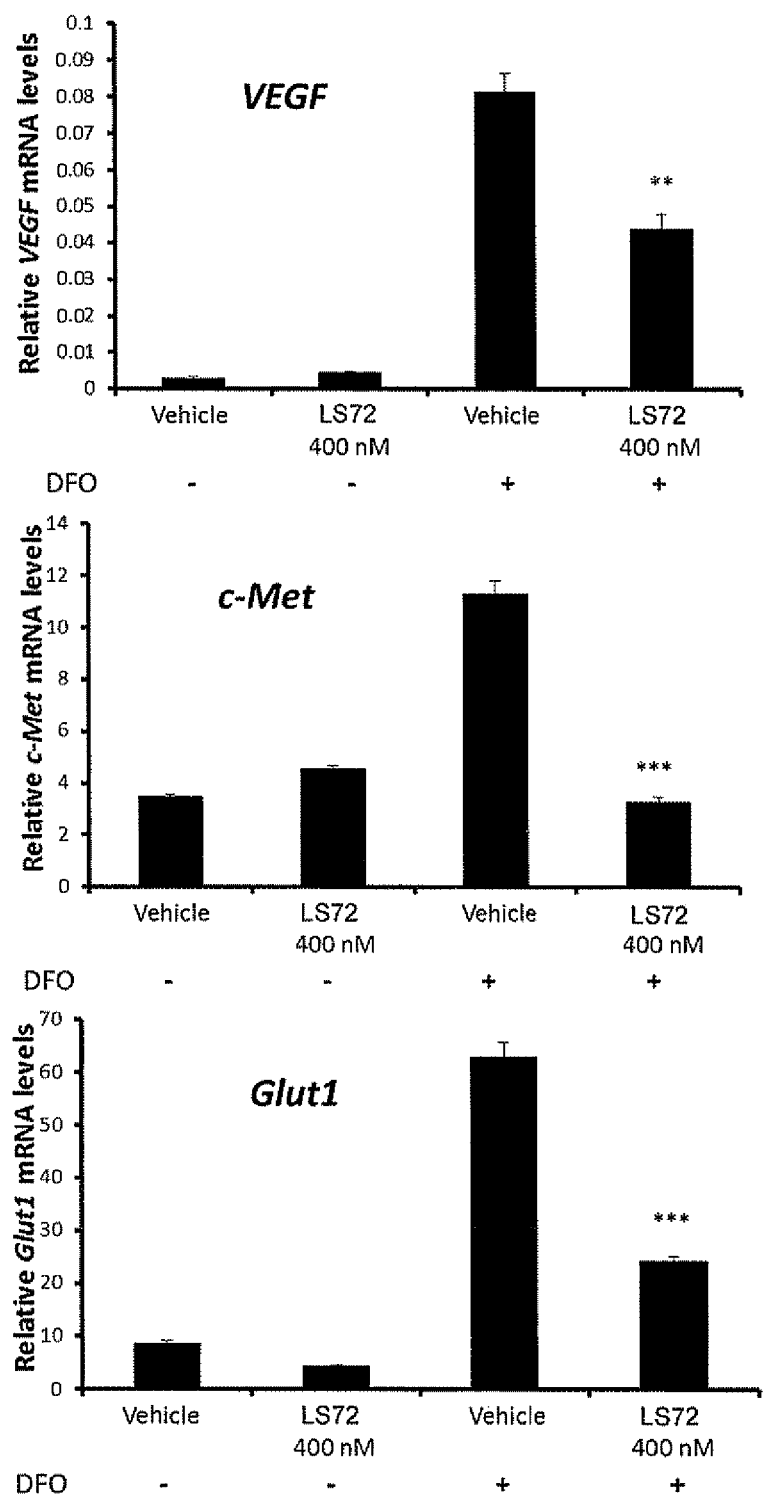
FIG. 13 mRNA levels of three HIF1α inducible genes: VEGF, c-Met and Glut1 in A549 cells after treatment with LS72. Data from qRT-PCR experiments showing mRNA levels of three HIF1α inducible genes, VEGF, c-Met and Glut1 in A549 after treatment of the cells in a medium with 0.2% serum with LS72 (400 nM). Hypoxia was induced 300 μM by DFO. Error bars are ±s.e.m for the experiments performed in quadruplicate. Error bars are ±s.e.m. of experiments performed in triplicate. *P<0.001,  P<0.01, t test.

After tests with various serum levels in the media and hypoxia induction methods, the conditions that worked remarkably and consistently well for the induction of HIF1α dependent genes were to keep A549 cells in 2% serum followed by treating cells with compound or control in the media with 0.2% serum for 48 h (FIG. 13). Under these conditions while hypoxia bag was the best option for induction of the LOX gene, the best hypoxic response leading to upregulation of many other HIF1α inducible genes was treatment with 300 μM DFO.

FIG. 13 shows the effect of LS72 treatment on the levels of three important genes VEGF, Glut1 and c-Met which are known to be upregulated in many solid tumors under hypoxic conditions.

Treatment with LS72 resulted in a significant reduction in the hypoxic response of VEGF, Glut1 and c-Met genes. VEGF levels were reduced by 50%, whereas Glut1 mRNA levels were reduced more than 60%. c-Met was also significantly downregulated, essentially reaching its normoxic levels (FIG. 13).

Figure 14A:
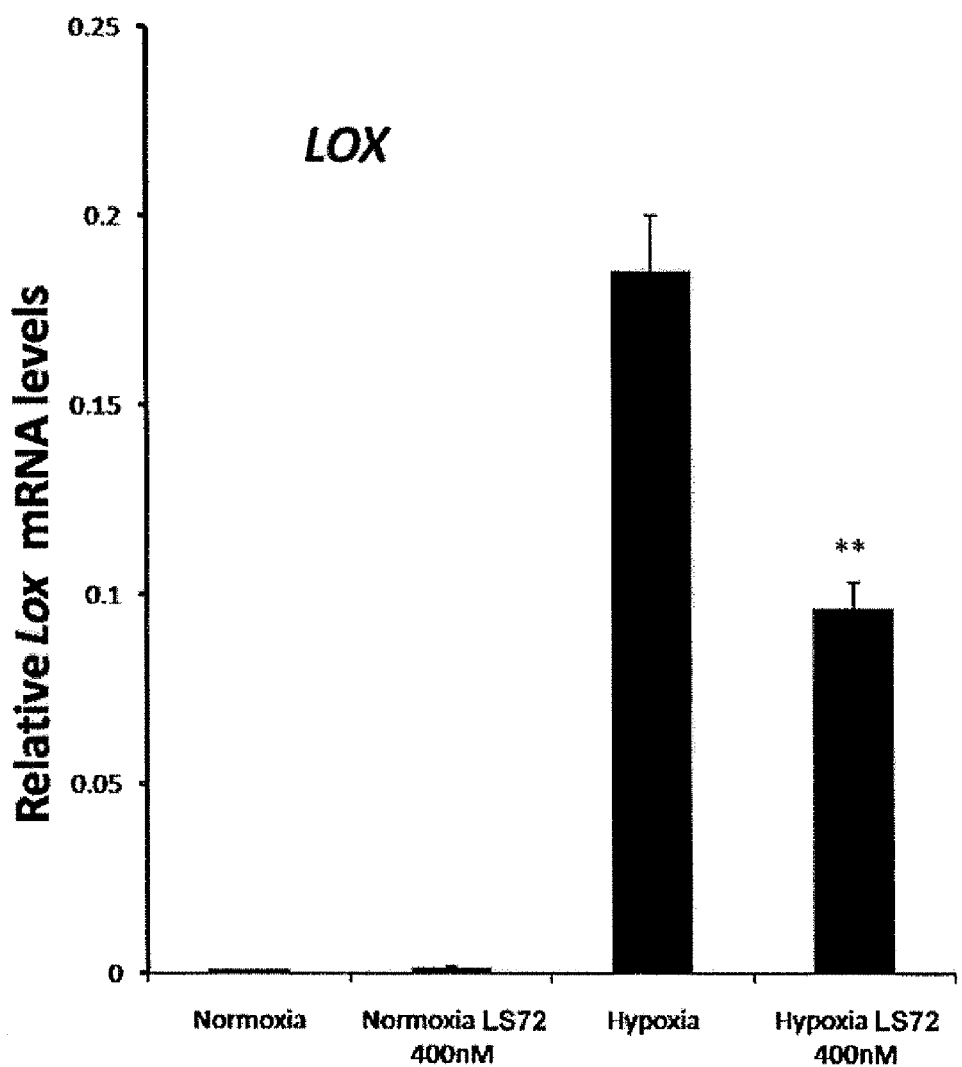
FIGS. 14 (A) qRT-PCR data for LOX and (B) CXCR4 genes in A549 cells treated with LS72. Hypoxia was induced by hypoxia bag. Cells were maintained in F-12K medium with 2% serum. After reaching 65% confluency the cells were grown in serum free media and treated with LS72 (400 nM). Hypoxia was induced with DFO (300 µM) for 48 h. Error bars are s.e.m. of experiments performed in triplicate. **P<0.01, t test.
Figure 14B:
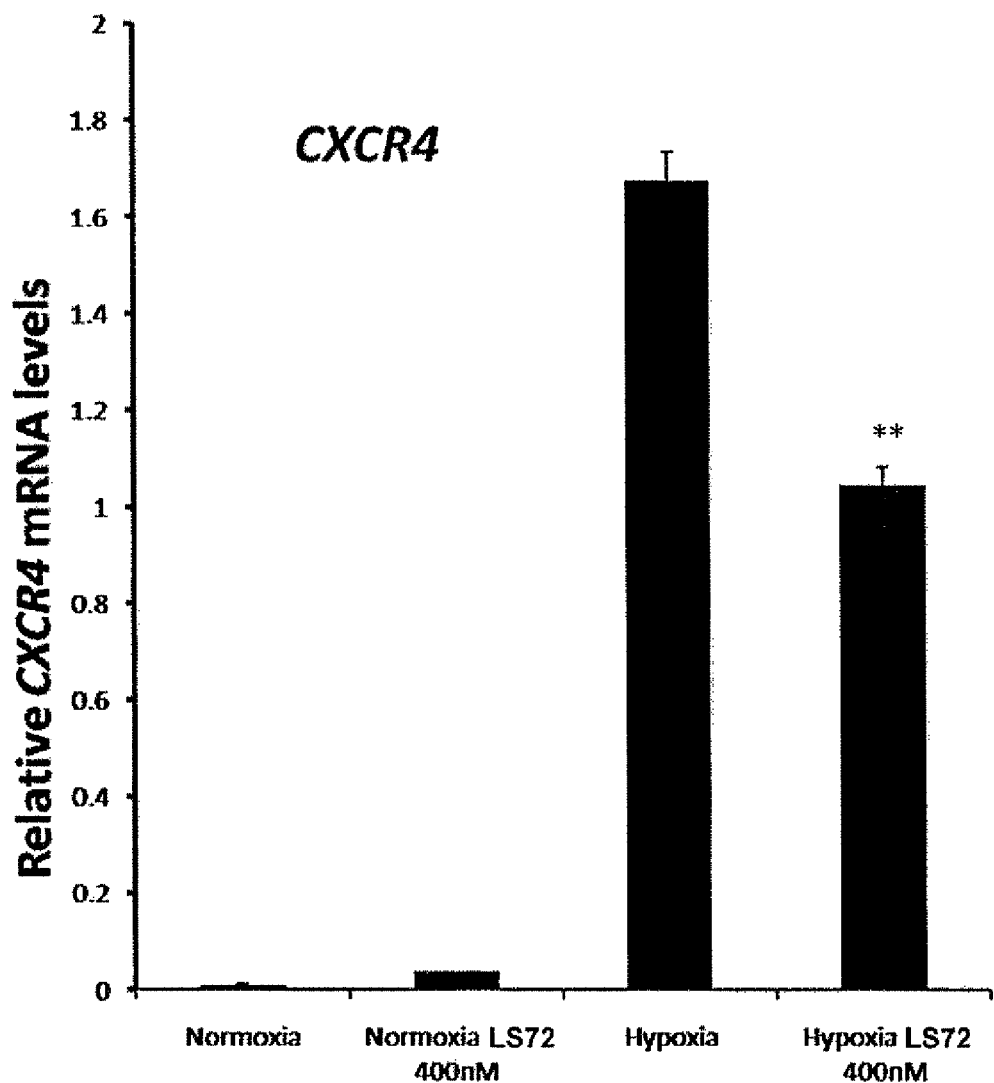

LOX (lysyl oxidase) is another gene that is upregulated under hypoxia and the protein is involved in regulating the extracellular matrix during invasive behavior and metastasis of cancer tissue[65]. LOX gene showed better induction with hypoxia bag after 48 h and showed significant downregulation in the transcriptional activity after treatment with LS72. CXCR4 is a gene that is essential for chemotaxis of stem cells and progenitor cells during healing of an injury that is also implicated in cancer stem cells migration[66]. SDF1-CXCR4 axis leads to chemotaxis of progenitor and stem cells to the cancer tissue or wound followed by their differentiation. In our model system of A549 cells CXCR4 is also upregulated more than 100-fold after chemical induction of hypoxia with DFO or hypoxia bag. Upon treatment with LS72 at 400 nM concentration, excellent inhibition of the transcriptional activity was observed for CXCR4 gene (FIG. 14).

Overall, A549 cell line under the conditions mentioned above became a very good model for studying HIF1α inducible gene expression. All the five genes mentioned above not only showed high up-regulation of HIF1α inducible transcription of many key genes involved in tumorigenesis but also under the given conditions showed very little change in the transcriptional activity under normoxia in the presence of LS72.

After obtaining great transcriptional induction for the five genes VEGF, c-Met, Glut1, LOX and CXCR4 which are upregulated by HIF1α transcriptional system and are downregulated upon treatment with 400 nM of LS72, the next logical step was to study the drug dose response. The modulation of HIF1α inducible transcription with LS72 was studied at three different concentrations of 100 nM, 400 nM and 1600 nM.

The hypoxia induction was done at a confluency of 85% cells in serum free F-12K medium with 300 μM DFO.

Figure 15:
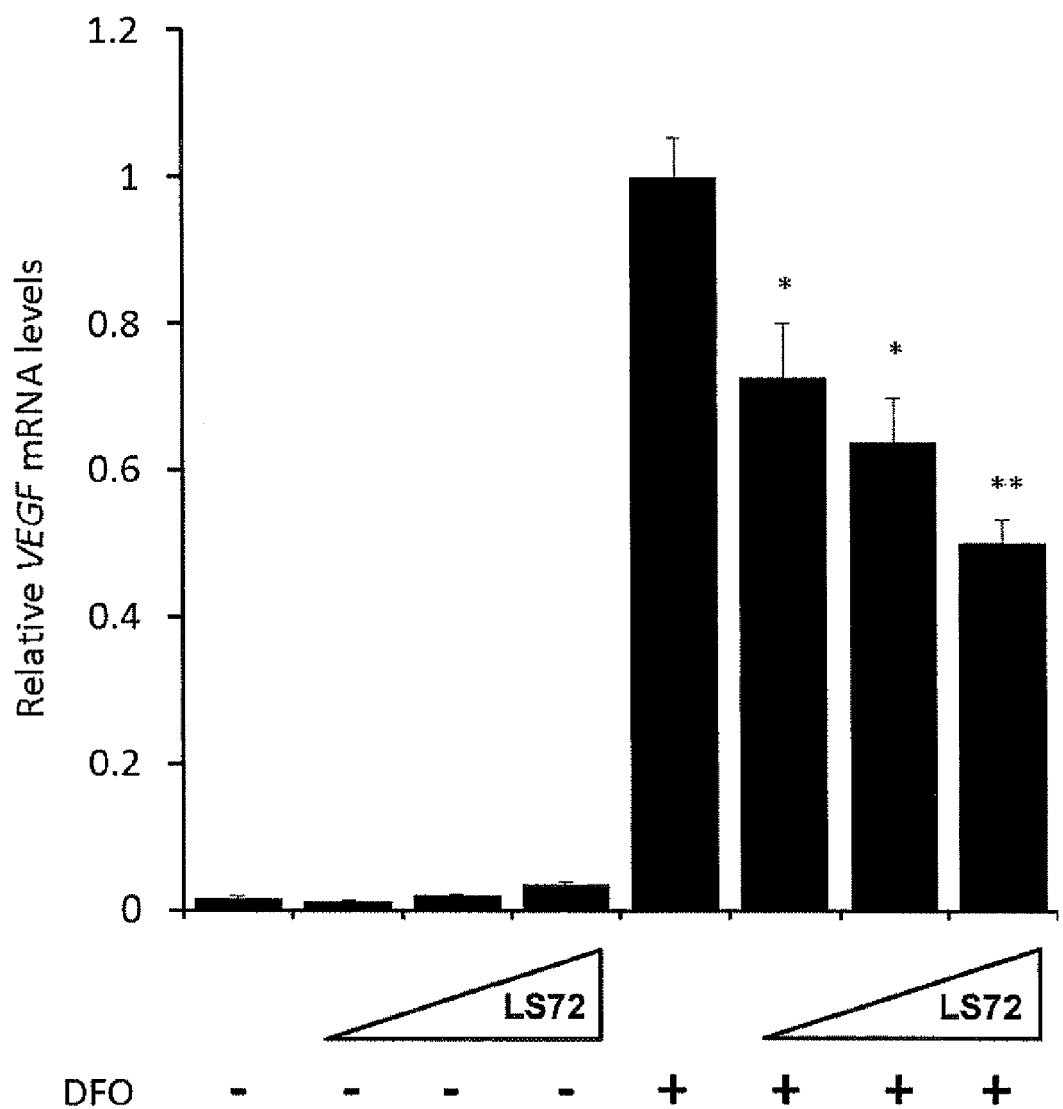
FIG. 15 mRNA levels for VEGF in A549 cell line, illustrating the dose response to LS72 treatment at three different concentrations. qRT-PCR assays were performed in order to determine the mRNA levels for VEGF in A549 cell line treated with LS72 at concentrations: 100 nM, 400 nM, 1600 nM. Hypoxia was induced by DFO (300 µM). Error bars are ±sem for the experiments performed in triplicate. Error bars are ±s.e.m. of experiments performed in triplicate. ** P<0.01, * P<0.05, t test.
Figure 16:
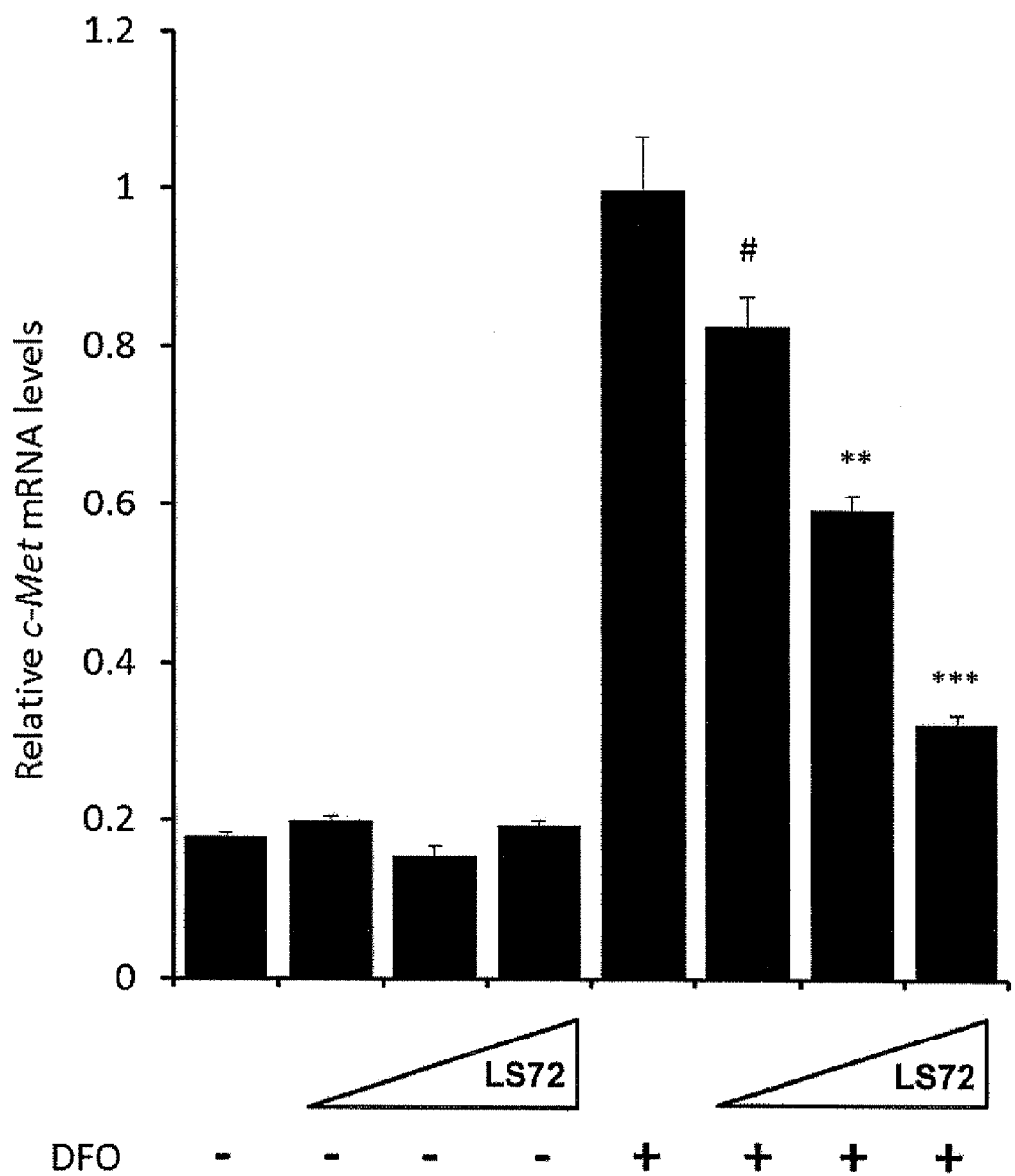
FIG. 16 mRNA levels for c-Met in A549 cell line showing dose response to LS72 at concentrations of 100 nM, 400 nM, 1600 nM. qRT-PCR was used to determine the mRNA levels of c-Met Hypoxia was induced with DFO (300 µM). Error bars are ±sem for the experiments performed in triplicate. Error bars are ±s.e.m. of experiments performed in triplicate. * P<0.001, P<0.01, # P<0.1, t test.

For each concentration of LS72 control samples were also present, where the cells were treated with LS72 but without induction of hypoxia. The controls showed that at the three different concentrations of LS72 in normoxia the VEGF transcription levels were not changed significantly, underlining the fact that in these conditions LS72 did not show increase or decrease in the transcriptional levels due to stress or some other pathway. Under hypoxia LS72 showed dose dependent decrease in the HIF1α inducible transcription of VEGF gene (FIG. 15).

c-Met gene under these conditions of hypoxic induction to highly confluent cells showed enhanced upregulation of its transcription. c-Met mRNA was up-regulated more than 5 folds in hypoxia. Dose-dependent decrease in transcriptional upregulation was observed for c-Met upon treatment with LS72 (FIG. 16).

Figure 17:
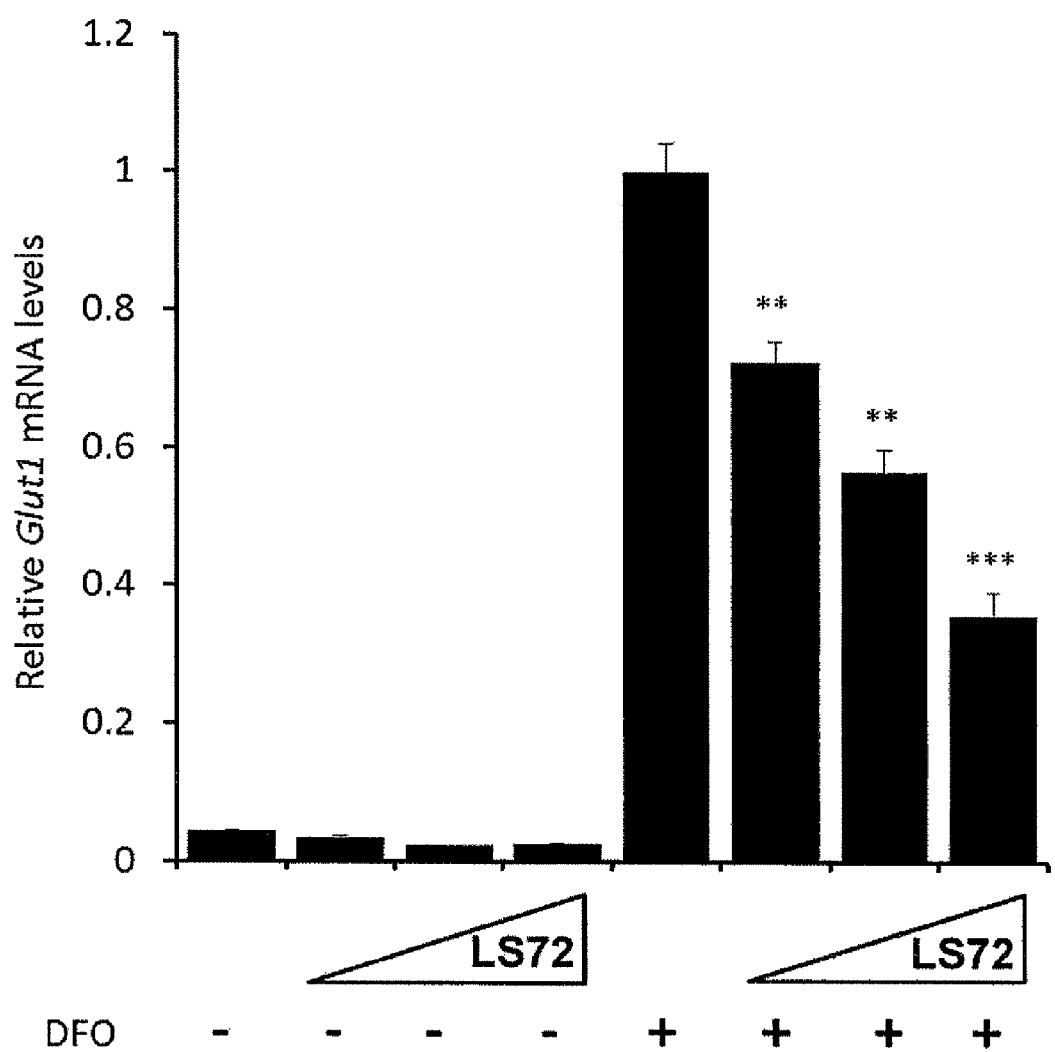
FIG. 17 qRT-PCR data for Glut1mRNA in 85% confluent A549 cells treated with LS72 at three different concentrations. qRT-PCR assays were performed in order to determine the mRNA levels for Glut1 in A549 cell line treated with LS72 at concentrations: 100 nM, 400 nM, 1600 nM. Hypoxia was induced with DFO (300 µM). Error bars are ±sem for the experiments performed in triplicate. Error bars are ±s.e.m. of experiments performed in triplicate. * P<0.001,  P<0.01, t test.

Glut1 which showed 10-fold induction in highly confluent cells. Glut1 also shows dose dependent decrease of hypoxic transcriptional up-regulation at 100 nM, 400 nM and 1600 nM of LS72 (FIG. 17).

Figure 18:
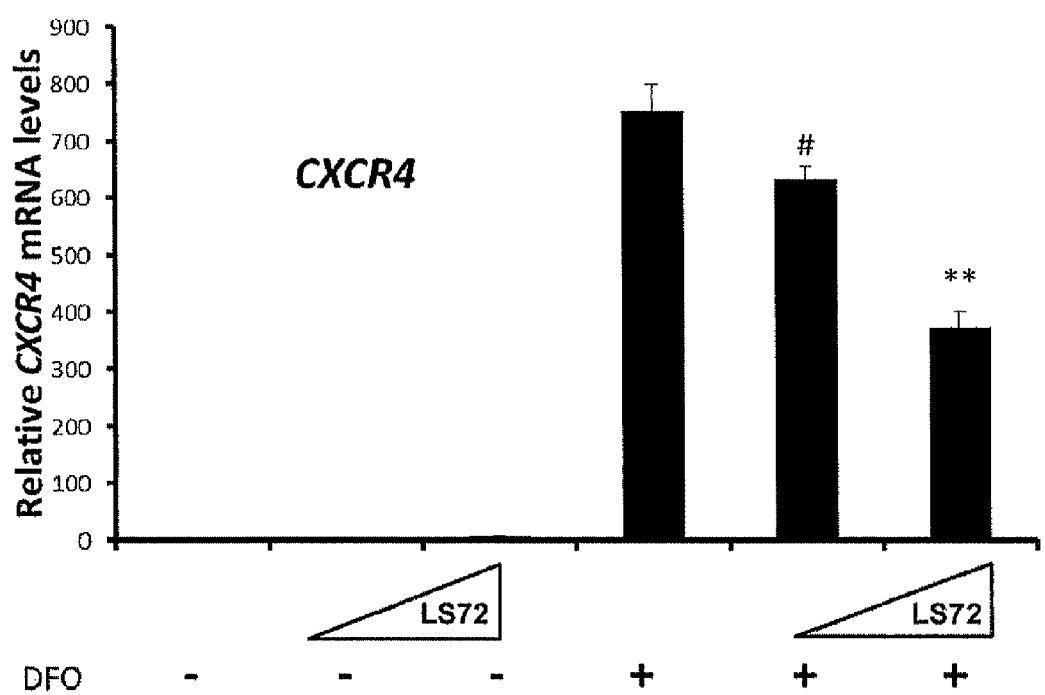
FIG. 18 qRT-PCR data for A549 cells where hypoxia was induced in 85% confluent cells. More than 650 fold induction of CXCR4 transcription was observed with DFO at 300 µM concentration. LS72 at two different concentrations of 400 nM and 1600 nM downregulated the CXCR4 mRNA levels in a dose dependent manner. Error bars are ±sem for the experiments performed in triplicate. Error bars are ±s.e.m. of experiments performed in triplicate. ** P<0.01, # P<0.1, t test.

CXCR4 is a G-protein coupled receptor that is upregulated under hypoxic conditions. We chose A549 cells and induced the hypoxia with DFO and found that in 85% confluent cells the levels of CXCR4 gene were transcriptionally overexpressed more than 650-fold. Upon treatment with LS72 at 400 nM and 1600 nM concentration a dose-dependent decrease in mRNA levels of CXCR4 could be observed FIG. 18). These finding not only show that CXCR4 is induced transcriptionally in A549 cells under hypoxic conditions but that it can be downregulated with small molecules targeting HIF1α pathway.

Downregulation of VEGF and c-Met Protein Levels with LS72

After obtaining significant downregulation of transcription for several key HIF-1 inducible genes including VEGF and c-Met, we studied the protein levels of VEGF and c-Met in order to see whether the downregulation observed in the mRNA levels is also translated into the downregulation of the corresponding protein levels. Western blots were done to measure the protein levels for VEGF and c-Met in MCF7 and MDA-MB-231 cell lines respectively treated with LS72. VEGF protein levels showed significant downregulation with chetomin (200 nM) and LS72 (400 nM) in MCF7 cells under HIF1α induction with 300 μM DFO (FIG. 19a). c-Met proteins levels also showed significant downregulation in the HIF1α induced protein levels upon treatment with chetomin (200 nM) and LS72 (400 nM) in MDA-MB-231 cells (FIG. 19b).

Gene Expression Profiling and Microarray Analysis

Since the target proteins p300 and CBP are pleiotropic multidomain coactivators, their $CH_1$ regions contain binding sites for multiple transcription factors. One potential concern of the use of ETPs for gene regulation is specificity, because inhibiting the interaction between CBP/p300 and transcription factors other than HIF1α may result in large numbers of affected genes. To rule out nonspecific genome-wide effects of ETPs, we conducted in vitro gene expression profiling experiments with LS72 using Affymetrix Human Gene ST 1.0 Arrays containing oligonucleotide sequences representing 28,869 transcripts.[67,68]

Figure 19:
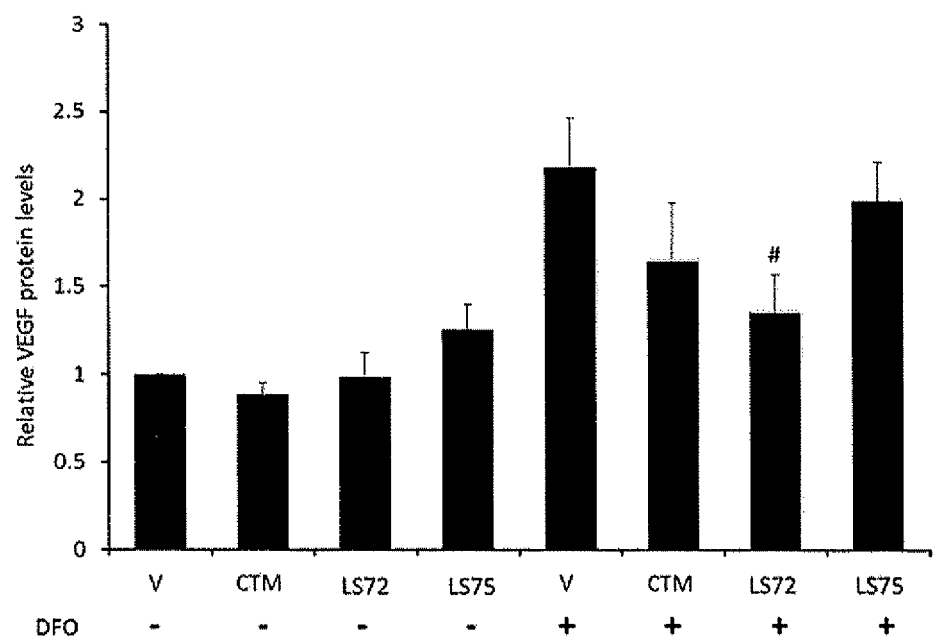
FIG. 19 VEGF and c-Met protein levels downregulated by LS72. a) MCF7 cells were treated with chetomin (200 nM), LS72 (400 nM) and LS75 (400 nM). HIF1α was induced with 300 µM DFO. Western blots were done in triplicate and bar graphs for the protein levels show significant downregulation of VEGF protein with LS72. b) MDA-MB-231 cells were treated with chetomin (200 nM), LS72 (400 nM) and LS75 (400 nM). HIF1α was induced with 150 µM CoCl2. Western blots were done in triplicate and bar graphs for the protein levels show that both chetomin and LS72 significantly downregulate c-Met protein levels.
Figure 19:
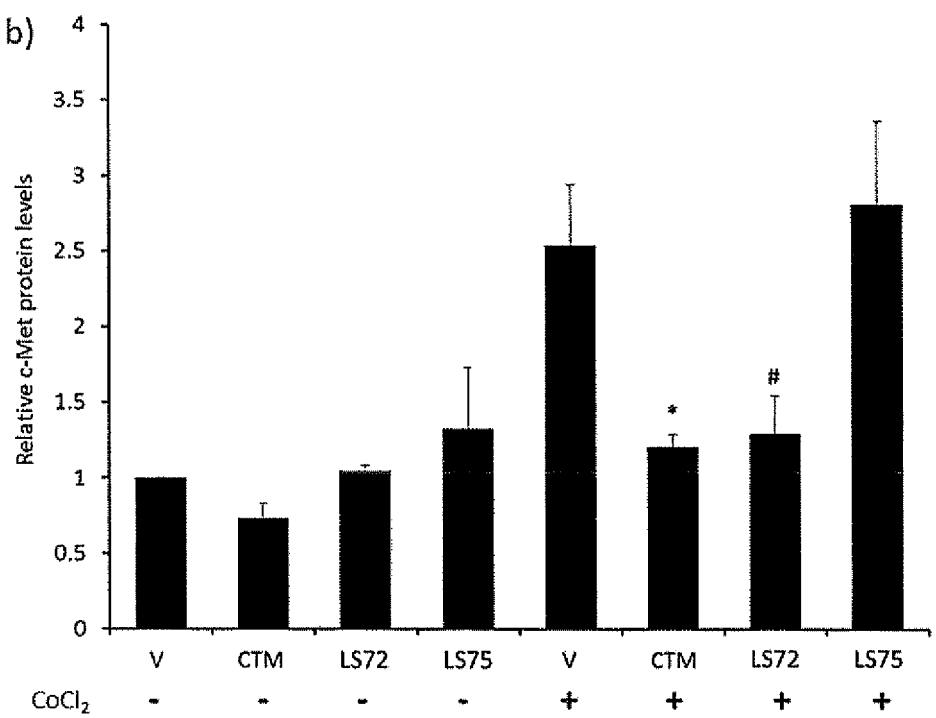
Figure 20:
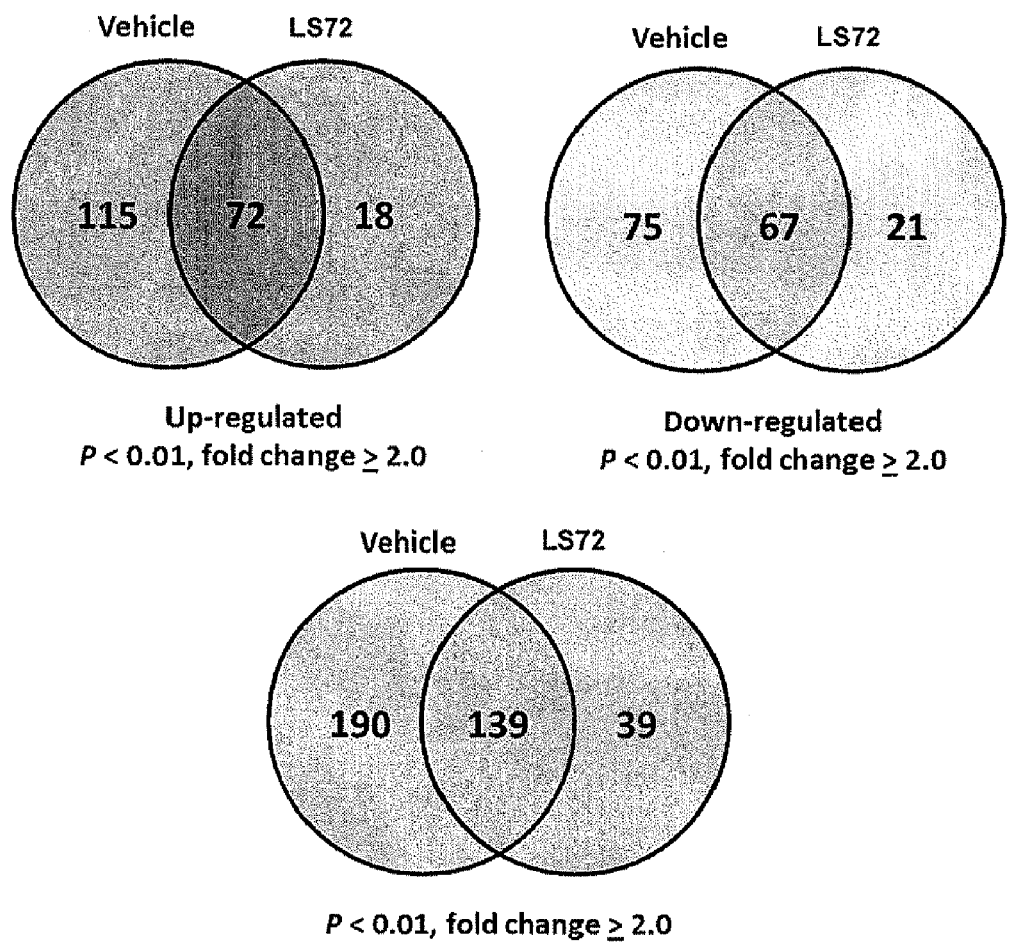
FIG. 20 Results from the analysis of microarray data. Green Venn diagram shows genes that are downregulated in vehicle (left green circle) i.e., genes that are downregulated in vehicle hypoxia as compared to vehicle normoxia and the right green circle shows the number of genes downregulated (>2.0 fold) in hypoxia treated with LS72 (400 nM) as compared to genes in normoxia treated with LS72. The red diagram shows the genes that are up-regulated in same conditions as explained for green Venn diagram. The blue diagram shows the overall effect of increase or decrease of genes (>2.0 fold) under the conditions mentioned above.

In order to interrogate cellular genome for global effects, MCF7 cells treated with LS72 at 400 nM were used. Treatment of cells with LS72 at a concentration of 400 nM affected the expression of only 178 genes at ≥2.0 fold levels (FIG. 20). By comparison, treatment with DFO alone changed levels of 329 genes ≥2.0 fold. Of these, 88 genes were downregulated ≥2.0 fold and 90-upregulated by ≥2.0 fold, respectively. In cells treated with LS72 under DFO-induced hypoxia conditions, we identified 190 genes were affected by this compound. Clustering analysis was performed to identify similarities in the expression profiles between different treatments (FIG. 19).

Figure 21:
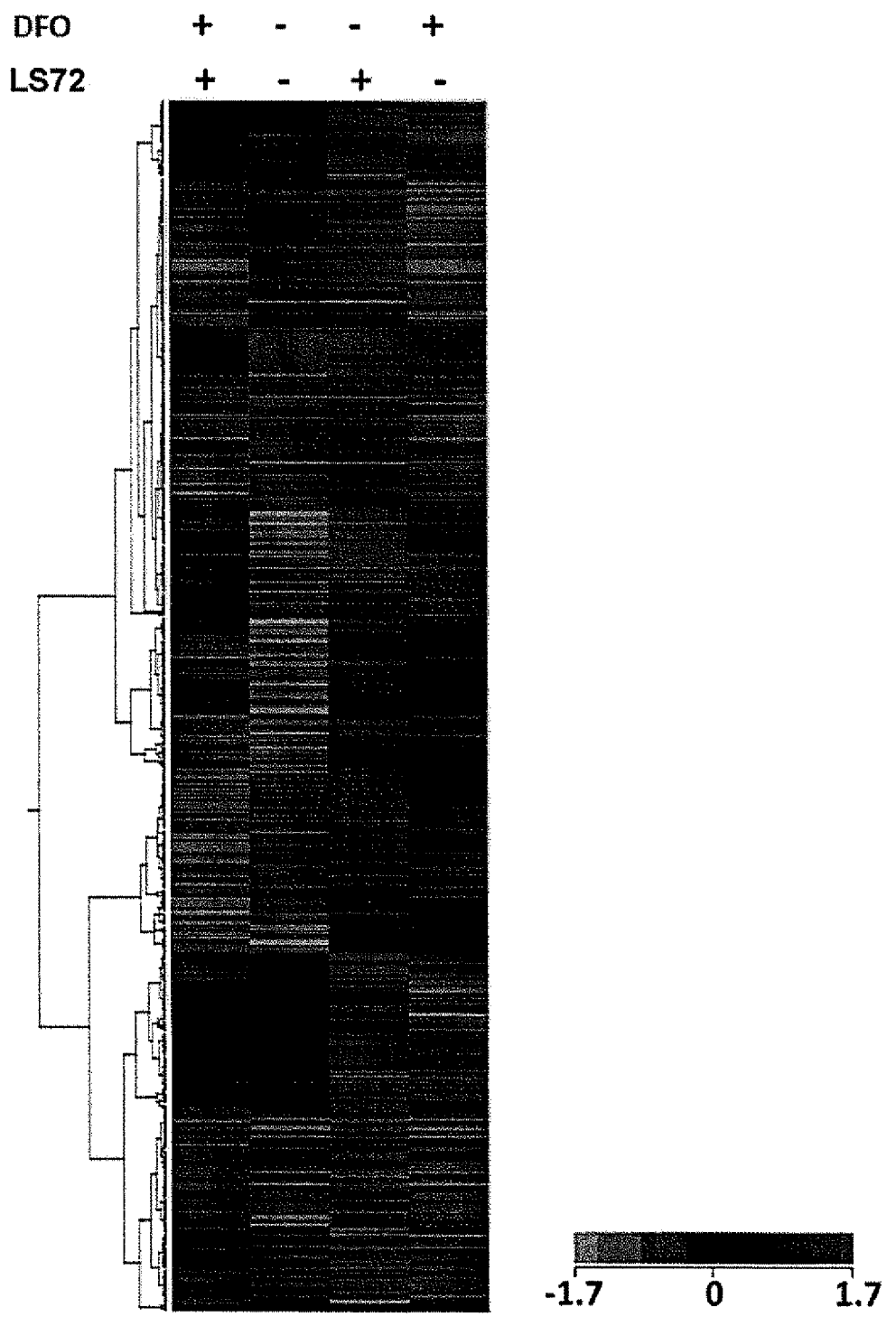
FIG. 21 Microarray analysis of MCF7 cells treated with LS72 at hypoxia induction using DFO (300 µM). Clustering analysis was done to see the similar trends in genes among different conditions. The analysis shows that the MCF7 cells under hypoxia and treated with LS72 (400 nM) shows similar trends as seen in vehicle which suggests that LS72 works towards nullifying the effect of hypoxia on global transcriptional levels.

FIG. 21 shows agglomerative clustering of genes under different conditions of hypoxia and treatment of LS72 (400 nM). The clustering shows that in many genes the effect of LS72 under hypoxia is to nullify the effect of hypoxia such that many genes transcriptional levels behave similar to that as seen in vehicle i.e. normoxia without LS72 treatment.

The expression profile of cells treated with LS72 under DFO-induced hypoxia is largely different from the profile under DFO alone. However, the profiles of the cells treated with LS72 under DFO-induced hypoxia and cells under normoxia conditions are showing regions of similarity. This suggests, that treatment with LS72 reduces the effect of DFO treatment on certain group of genes, as expected for transcriptional inhibitor that affects hypoxia-inducible genes. It is not entirely surprising that there is some overlap in genes affected by both LS72 and DFO given the complexity of cellular signaling pathways involved in the hypoxic response. The results also clearly demonstrate specificity of LS72 in its effect on hypoxia-induction in the context of the entire genome.

Table 1 lists important genes that are downregulated under hypoxia with 400 nM LS72 treatment in MCF7 cells. The data extracted from the lists of genes that show >2-fold change.

Interestingly, many genes that belong to solute carrier (SLC) family of proteins were down-regulated under hypoxia with LS72. They are listed in Table 2. This shows that under hypoxia solute carrier proteins are upregulated to facilitate higher uptake and secretion of molecules in the cells and LS72 has reversed this trend.

Figure 22:
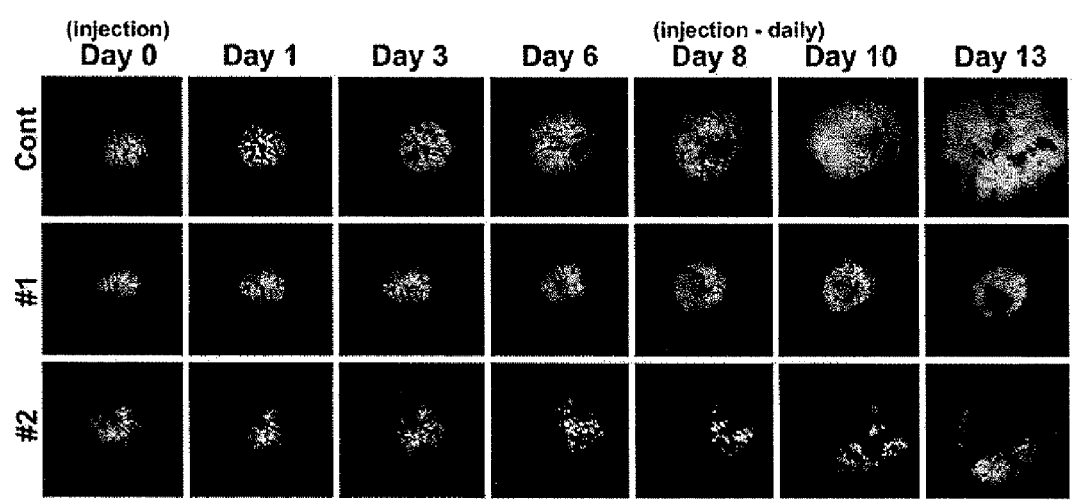
FIG. 22 Intravital microscopy images of murine subcutaneous tumor model of fluorescent N2O2 cells stably transfected with H2B-GFP construct. Mice with N2O2 H2B-GFP tumors were injected intravenously on day 0 with 1 mg/kg of LS72 compound followed by daily injections of 2 mg/kg after day 8 and imaged over 2 weeks. Fluorescence IVM images of tumors taken on days indicated post-treatment.

In vivo Study of the Efficacy of LS72 in Mouse Tumor Xenografts Model Using Intravital Microscopy Tumor spheroids from N2O2 (breast carcinoma) were prepared and implanted subcutaneously into the nude mice. Tumors were allowed to vascularize for 10-14 days after which mice were injected on Day 0 with 1 mg/kg of (±)-LS72 via tail vein. From Day 8 to Day 13 mice were daily injected with 2 mg/kg of (±)-LS72. Intravital microscopy (IVM) images, obtained on specified days are shown in FIG. 22.

Figure 23:
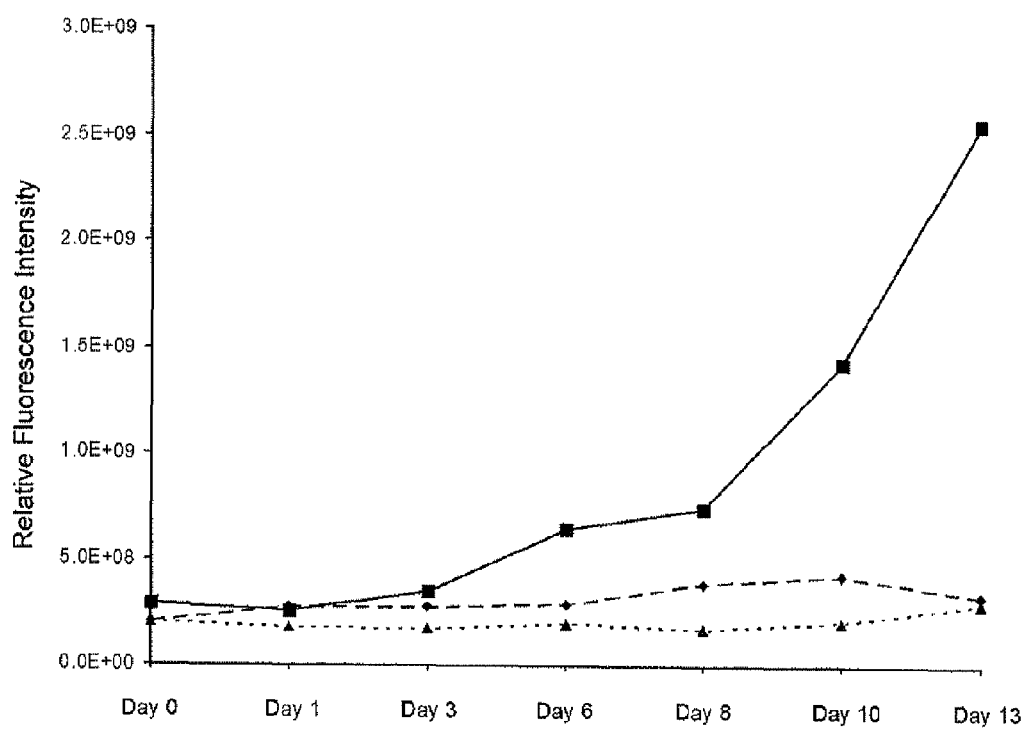
FIG. 23 Change in fluorescence intensity obtained from tumor images from IVM of mice treated with or without LS72. Graphs show the quantitative difference between the tumor volumes as shown in IVM images in FIG. 22. Vehicle mouse (-■-) and mice treated with LS72, #1 (-▲-) and #2 (-◆-).
Figure 24:
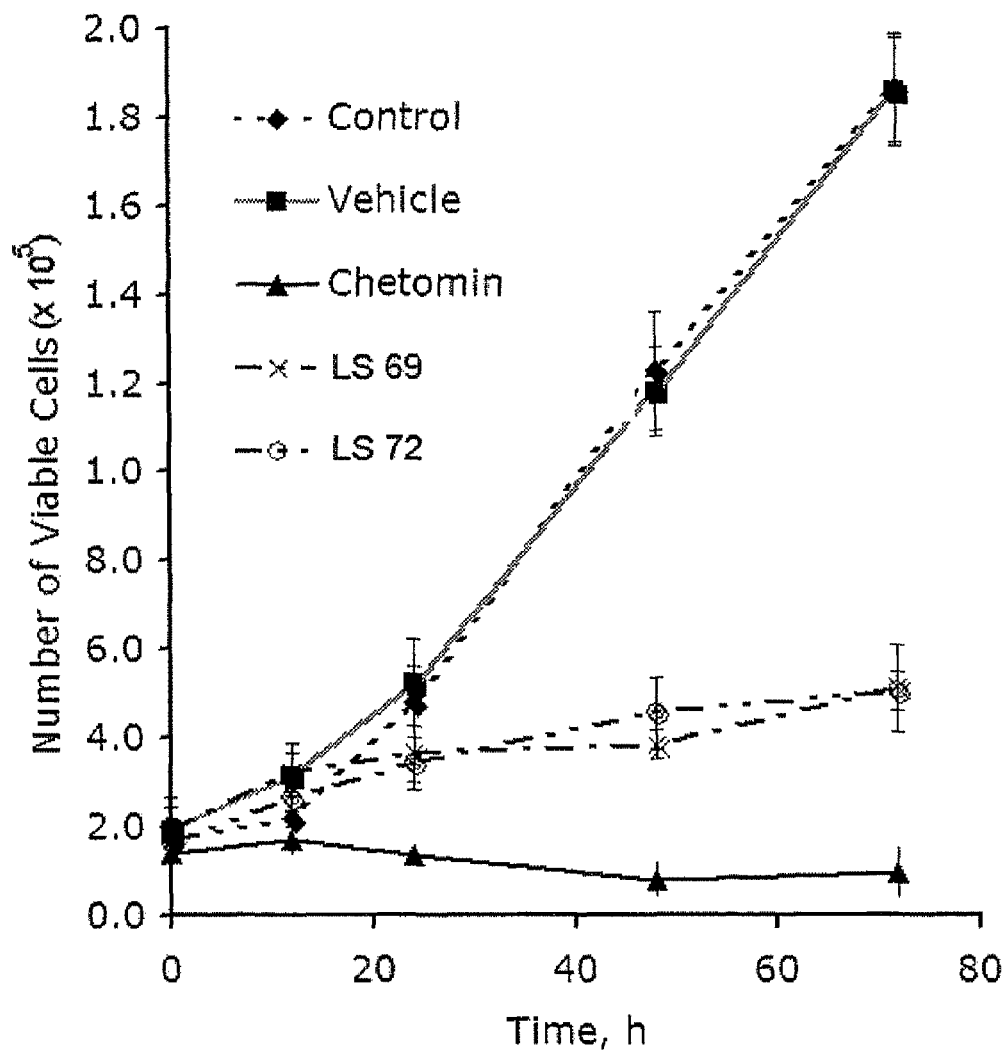
FIG. 24 Cell density and population doubling data for HeLa cells treated with chetomin CTM and ETPs LS69 and LS72. Control: cell culture medium only, vehicle: 0.1% DMSO in cell culture medium.

FIG. 23 is shows quantification of the tumor volume obtained from the IVM images. The data clearly shows that in mice #1 and #2, injected with (±)-LS72 the tumor vasculature and tumor growth are significantly suppressed. In the course of these experiments, (±)-LS72 showed very low toxicity to mice, as confirmed by observation of the behavior of the animals and monitoring of their body weights. This low toxicity of our designed bis-ETP is giving it a significant advantage in vivo over the natural bis-ETP chetomin, which is reported to be toxic and even lethal to animals, because mice treated with chetomin do not survive after five days of consecutive injection.

In our study, mice treated with (±)-LS72 survived the 14-day treatment and did not show any signs of acute toxicity. This study validates, efficacy of (±)-LS72 as an inhibitor of HIF-1 inducible gene expression in cancer cell lines in vitro and tumor growth in mouse xenograft model in vivo. (±)-LS72 is significantly less toxic than chetomin within the tested range of therapeutic concentrations sufficient to maintain the inhibition of tumor growth in vivo.

Additional experiments were carried out where tumors in mice were allowed to vascularize for 10-14 days after which mice were injected on Days 0, 8, 10, and 12 with 1 mg/kg of meso-LS72 via tail vein. Intravital microscopy (IVM) images on Days were obtained as described above. The data shows that mice injected with meso-LS72 the tumor vasculature and tumor growth are also significantly suppressed. In the course of these experiments, meso-LS72 also showed very low toxicity to mice, as confirmed by observation of the behavior of the animals and monitoring of their body weights. This establishes the in vivo efficacy of both (±)-LS72 and meso-LS72 in suppressing tumor growth in a mouse xenograft model.

Discussion

As disclosed herein, the compounds of the invention are capable in disrupting the hypoxia inducible transcription in vitro and in vivo with little deleterious effect on cell growth and replication rate. In hypoxic breast carcinoma cell lines MCF7 and MDA-MB-231 the designed dimeric 1,572 shows significant downregulation of HIF1α inducible transcription of VEGF and c-Met genes and their protein products. In lung adenocarcinoma cell line A549, five key genes VEGF c-Met, Glut1, LOX and CXCR4 have been significantly downregulated with LS72 in a dose-dependent manner. Our gene expression profiling experiments provided important insights into the global genomic effects of LS72 under hypoxia conditions. The number and type of genes affected by LS72 is consistent with our previous results suggesting that this compound is a highly specific transcriptional inhibitor with well-defined pharmacogenomic profile.

Materials and Methods

General Methods

All reagents and solvents were obtained from commercial sources and were used as received unless otherwise stated. All reactions involving moisture-sensitive reagents were conducted under a dry $N_2$ atmosphere with anhydrous solvent and flame dried glassware. Hygroscopic liquids were transferred via a syringe and were introduced into reaction vessels through rubber septa. Reaction product solutions were concentrated using a rotary evaporator at 30-150 mm Hg. Gravity chromatography was performed on silica gel (230-400 mesh) using reagent grade solvents. Analytical thin-layer chromatography was performed on glass-backed, pre-coated plates (0.25 ram, silica gel 60, F-254, EM Science). Nuclear Magnetic Resonance (NMR) spectra were collected on Varian Unity 300 MHz, or Bruker 250 MHz, 500 MHz or 600 MHz instruments in the indicated solvents. The peak positions are reported with chemical shifts (δ) in ppm referenced to tetramethylsilane (0 ppm), or the signals resulting from the incomplete deuteration of the solvent: CDCl$_3$ (7.26 ppm), or the center line of the multiplet of CD$_3$OD (3.31 ppm). 13C NMR spectra were referenced to signals of CDCl$_3$ (77.0 ppm) or CD$_3$OD (49.2 ppm). The coupling constants (J) are reported in Hertz (Hz). The following abbreviations are used: singlet (s), doublet (d), triplet (t), quartet (q), doublet of doublets (dd), doublet of triplets (dt), broad (br).

Synthesis and Characterization of Epidithiodiketopiperazines

Preparation of 1,4-dimethyl-2,5-piperazidnedione-3,6-dibromide (2)

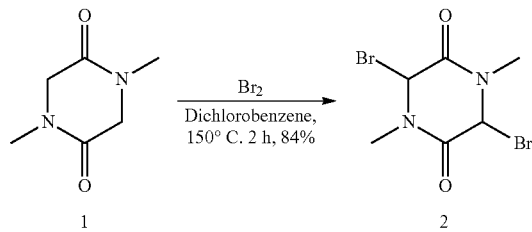

Bromine (1.03 mL, 3.2 g, 20 mmol, 2 eq.) dissolved in o-dichlorobenzene (10 mL) was added dropwise over a period of 1 h to a solution of sarcosine anhydride (1.42 g, 1 mmol, 1 eq., Avocado, Inc.) slurry in o-dichlorobenzene (30 mL). A yellow precipitate formed immediately. The reaction mixture was heated up to 150° C. and stirring was continued until the evolution of gas ceased. The mixture was then cooled to RT and hexanes (200 mL) was gradually added. Pale yellow crystals deposited and the mixture was allowed to stand overnight at 4° C. The crystals were filtered off and dried under vacuum. The crude product was recrystallized from chloroform-ether mixture to give 1.62 g of product. Yield 54%, m.p. 128° C. $^1$H-NMR (CDCl$_3$, TMS, ppm) δ: 6.00 (s, 2H), 3.07 (s, 6H).

Preparation of 1,4-dimethyl-2,5-piperazidnedione-3,6-dithioacetate (3)

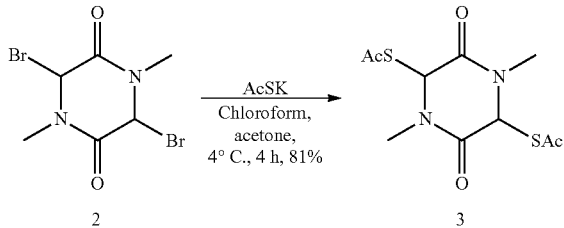

Potassium thioacetate (6.2 g, 54 mmol, 2.7 eq.) was added in portions over a period of about 1 h to a solution of Et$_3$N (3.1 mL, 22 mmol) and crude 2 (20 mmol), dissolved in chloroform (50 mL) and acetone (50 mL) mixture at 4° C. The reaction mixture was stirred an additional 3 h at 4° C. The sample recorded by NMR showed no starting material. The mixture was evaporated under reduced pressure, the residue was dissolved in dichloromethane and the organic phase was for times washed with water, dried under MgSO$_4$ and reduced in volume on rotary evaporator. The mixture of dark syrup with some crystalline material was dissolved in EtOAc and hexane was added until the solution became cloudy. Crystalline material formed, which was filtered, dried to give 3.3 g (54%) of product 3, m.p. 204° C. $^1$H-NMR (CDCl$_3$, TMS, ppm) δ: 2.95 (s, 6H), 2.49 (s, 6H).

Preparation of 1,4-dimethyl-2,5-piperazidnedione-3,6-dithiol (4)

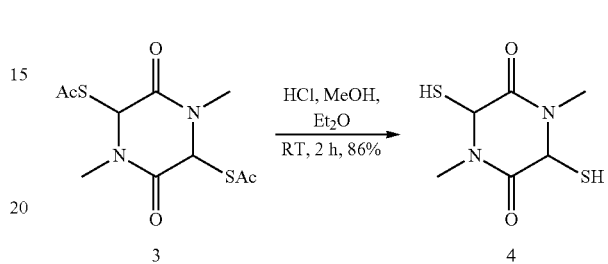

Thioacetate (3, 1.33 g) was suspended in anhydrous MeOH (40 mL) and 1M HCl in anhydrous ether (40 mL) was added. The reaction mixture was stirred and refluxed for 2 h. The slurry became yellowish, with solution clearing slowly. The disappearance of starting material was monitored by TLC and determined to be complete after 2 h. The solution was concentrated in vacuo and the residue was dissolved in chloroform and evaporated. The chloroform dissolution-evaporation procedure was repeated again to give 4, 0.8 g (85%). NMR spectrum was recorded on crude compound. M.p. 108° C. $^1$H-NMR (CDCl$_3$, TMS, ppm) δ: 5.00 (d, 2H, J=10.3 Hz), 3.09 (s, 6H), 3.06 (d, 2H. J=10.2 Hz).

Preparation of 3-(4-methoxy-phenyl)-6,8-dimethyl-2,4-dithia-6,8-diaza-bicyclo[3.2.2]nonane-7,9-dione (5)

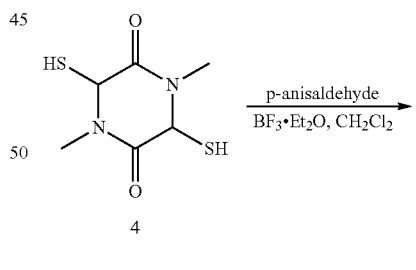

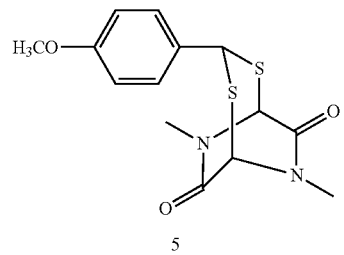

The crude 4 (1.11 g) and p-anisaldehyde (4.1 mL) was dissolved in dichloromethane (50 mL). To this stirred solution, boron trifluoride etherate (250 μL) was added. After stirring at room temperature for 16 hr the solution was poured into a saturated sodium bicarbonate solution. The aqueous layer was thoroughly extracted with dichloromethane and the organic phase was dried over $Na_2SO_4$. After evaporating the solvent, the residue was tested by TLC (dichloromethane-EtOAc, 7:3, $R_f$ 0.45) and crude NMR was recorded. The crude NMR shows the target compound and the excess of p-anisaldehyde. The crude mixture was dissolved in dichloromethane and the product was precipitated out with ethyl ether to give 590 mg of purified product. From the mother liquid a second part of product crystallized out, diving 260 mg of product. Total amount is 850 mg of 5 (50%), m.p. 269° C. $^1$H NMR ($CDCl_3$, TMS, ppm) δ: 7.38 (d, J=8.9 Hz, 2H), 6.87 (d, J=8.9 Hz, 2H), 5.15 (s, 1H), 5.03 (s, 1H), 4.87 (s, 1H), 3.80 (s, 1H), 3.20 (s, 3H), 3.07 (s, 3H)

Preparation of 1,4-dimethyl-2,5-piperazidnedione-3,6-disulfide (6)

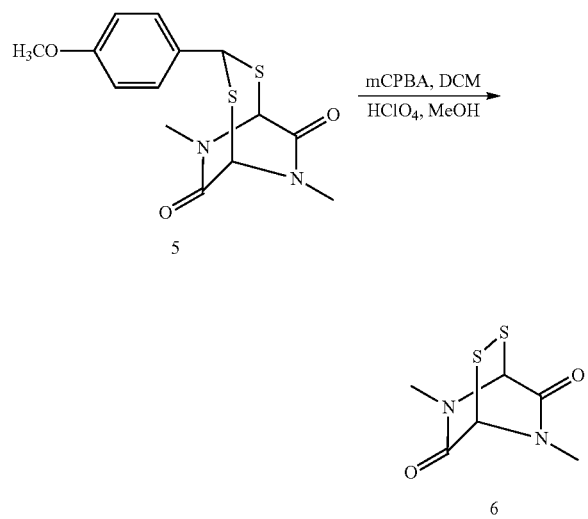

Thioacetal (5) (18 mg, 0.056 mmol, 1 eq.) was dissolved in anhydrous dichloromethane (15 mL) and the solution was cooled to 0° C. To the stirred solution m-chloroperbenzoic acid (15 mg, 0.067 mmol, 1.2 eq, max 77% pure) was added. After 10 min of stirring at 0° C., dimethyl sulfide (20 μL) was added. The solution was then treated with 25 μL of perchloric acid in methanol (1:5). The solution was allowed to stand at room temperature for 8 hr and then poured into saturated sodium bicarbonate solution. The aqueous layer was extracted with dichloromethane. The dichloromethane solution was washed with water, dried under $MgSO_4$ and concentrated under vacuum to gain 18 mg of crude product. The white precipitate was washed with $Et_2O$ to obtain 8 mg (71%) of purified product (6). $^1$H-NMR ($CDCl_3$, TMS, ppm) δ: 5.22 (s, 2H), 3.11 (s, 3H). ESI MS: Calcd. for $C_6H_8N_2O_2S_2$: 204.0. Found [M+H]$^+$: 204.8.

Preparation of 3-(4-methoxyphenyl)-6,8-dimethyl-2-[(phenylmetoxy)methyl]-2,4-dithia-6,8-diazabicyclo [3.2.2]nonane-7,9-dione, (7)

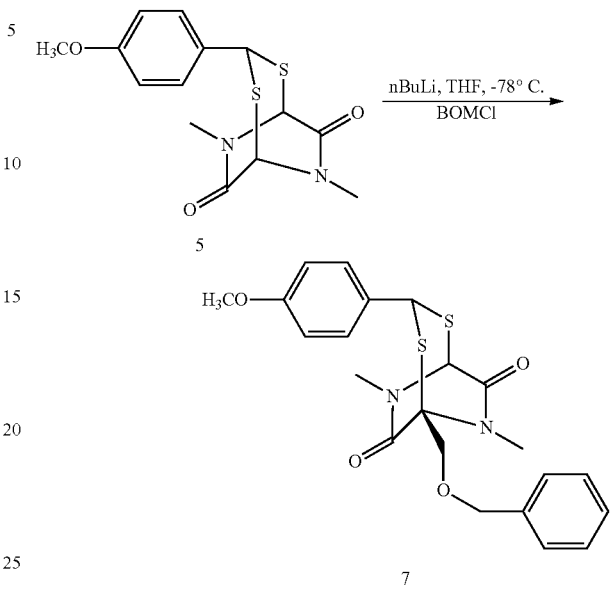

Crystalline 5 (388 mg, 1.2 mmol, 1 eq.) and benzyl chloromethyl ether (1.11 mL, 4.8 mmol, 4 eq., 749 mg, 1.25 g, 60% reagent only) was dissolved in anhydrous THF (40 mL). The solution was cooled to −78° C. and to the stirred mixture, 1.54 M n-butyllithium in hexane (1.16 mL (1.8 mmol, 1.5 eq.) was added dropwise over a period of 5 min. After the mixture was stirred for 10 min at −78° C. the resulting red, cloudy solution was allowed to warm to room temperature and was stirred for 30 min. The TLC shows one major product and a little (~20%) starting material. Saturated NaCl solution was then added into the reaction mixture and the red solution was extracted with dichloromethane. The dichloromethane solution was washed with water twice, dried under $MgSO_4$ and concentrated in vacuo. The syrup was separated on column (hexane-ethyl acetate, 7-3; Rf 0.43) to give 364 mg of 5, as an off-white powder (68%). $^1$H-NMR ($CDCl_3$, TMS, ppm) δ: 7.36 (m, 5H), 7.31 (d, J=8.7 Hz, 2H), 6.84 (d, J=8.7 Hz, 2H), 5.11 (s, 1H), 5.04 (s, 1H), 4.74 (d, J=11.2 Hz, 1H), 4.54 (d, J=11.2 Hz, 1H), 4.22 (d, J=10.5 Hz, 1H), 3.82 (d, J=10.5 Hz, 1H), 3.79 (s, 3H, 3.23 (s, 3H), 3.10 (s, 3H). FAB-MS: Calcd for $C_{22}H_{24}N_2O_4S_2$: 444.1. Found [M+H]$^+$: 445.1.

Preparation of 1,4-dimethyl-2-[(phenylmetoxy)methyl]-2,5-piperazidnedione-3,6-disulfide (8)

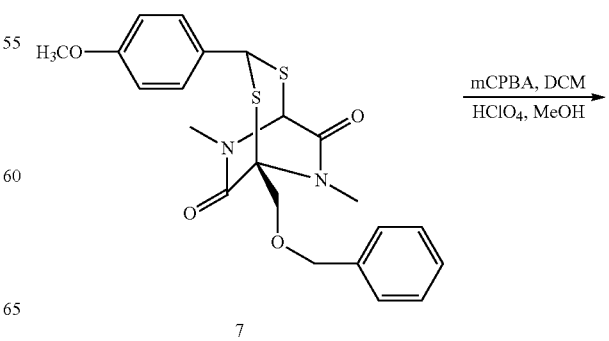

-continued

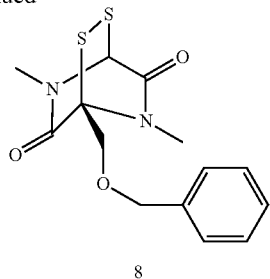

8

Purified 7 (9.2 mg, 0.021 mmol, 1 eq.) was dissolved in anhydrous dichloromethane (4 mL) and the solution was cooled to 0° C. To the stirred solution m-chloroperbenzoic acid (5.5 mg, 0.025 mmol, 1.2 eq., 77% pure) was added. After 10 min of stirring at 0° C., dimethyl sulfide (4.6 μL) was added. The solution was then treated with 9.2 μL of perchloric acid, in methanol (1:5). The solution was allowed to stand at room temperature for 2 hr and then 0° C. for 18 h. The reaction mixture was followed by HPLC. After 18 h there was no more change. The mixture was evaporated under vacuum and was separated by preparative HPLC to give 3.5 mg (49%) of pure compound 8. $^1$H-NMR (CDCl$_3$, TMS, ppm) δ 7.38 (m, 5H), 5.26 (s, 1H), 4.72 (d, J=1.8 Hz, 2H), 4.22 (d, J=1.8 Hz, 2H), 3.12 (s, 3H).

Preparation of 3-(4-methoxyphenyl)-6,8-dimethyl-2,4-di[(phenylmetoxy)methyl]-2,4-dithia-6,8-diazabicyclo[3.2.2]nonane-7,9-dione (9)

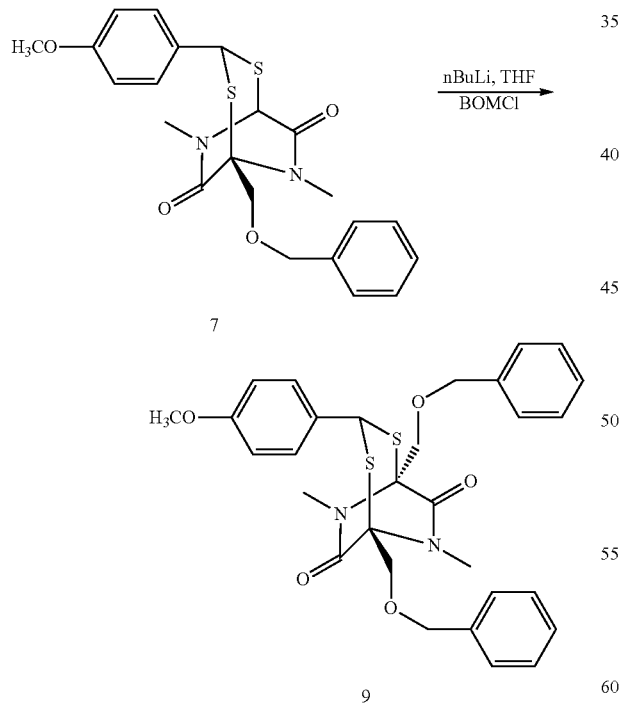

Thioacetal 5 (227 mg, 0.7 mmol, 1 eq.) and 1 mL of benzyl chloromethyl ether (546 mg, 3.5 mmol, 5 eq., 60% of reagent in the commercial source) was dissolved in anhydrous THF (35 mL) and the solution was cooled to −78° C. To the stirred solution 1.54 M n-butyllithium in hexane (1 mL, 1.54 mmol, 2.2 eq.) was added dropwise over a period of 10 min. After the mixture was stirred for 10 min at −78° C. the reaction was allowed to warm up to room temperature. It took about 30 min. The TLC shows one major product and no starting material. Saturated NaCl solution was added into the reaction mixture and the red solution was extracted with dichloromethane. The dichloromethane solution was washed with water twice, dried under MgSO$_4$ and concentrated under reduced pressure. The oily residue was separated via column chromatography on silica gel to give 185 mg of disubstituted product 9 (47%). $^1$H NMR (CDCl$_3$, TMS, ppm) δ: 7.38 (m, 10H), 7.31 (d, J=8.7 Hz, 2H), 6.86 (d, J=8.5 Hz, 2H), 5.00 (s, 4.76 (d, J=12.3 Hz, 1H), 4.74 (d, J=12.0 Hz, 1H), 4.71 (d, J=11.0 Hz, 1H), 4.61 (d, J=12.0 Hz, 1H), 4.57 (d, J=12.3 Hz, 1H), 4.49 (d, J=10.6 Hz, 1H), 4.30 (d, J=10.7 Hz, 1H), 3.83 (d, J=11.1 Hz, 1H), 3.80 (s, 3H), 3.29 (s, 3H), 3.20 (s, 3H). FAB-MS: Calcd for C$_{30}$H$_{32}$N$_2$O$_5$S$_2$: 564.1. Found [M+H]$^+$: 565.1.

Preparation of 3-(4-methoxyphenyl)-6,8-dimethyl-2-[(phenylmetoxy)methyl]-4 methylhydroxy-2,4-dithia-6,8-diazabicyclo[3.2.2]nonane-7,9-dione (10)

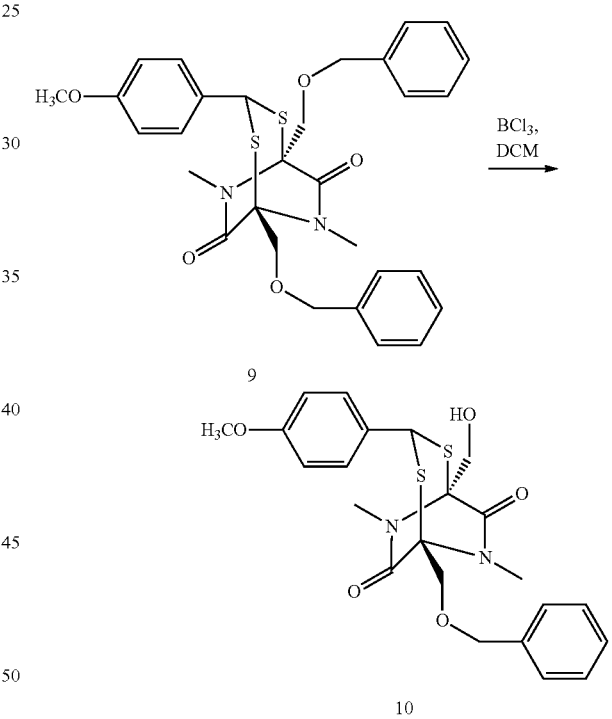

A solution of 280 mg of 9 (0.5 mmol, 1 eq.) in dichloromethane (30 mL) was cooled to 0° C. To this, 1M boron trichloride (625 μL, 0.625 mmol, 1.25 eq.) in dichloromethane was added dropwise, over a period of 30 seconds. The solution was allowed to stir at 0° C. for 10 min. and then poured into ice water. The water phase was extracted with dichloromethane. The dichloromethane solution was washed with water, dried under MgSO$_4$ and concentrated under vacuum to gain 350 mg of crude product. The glassy solid was purified via column chromatography on silica gel in a dichloromethane-EtOAc mixture (85-15), Rf 0.44, to give 175 mg of 10 (74%). NMR (CDCl$_3$, TMS, ppm) δ: 7.30 (m, 5H), 7.28 (d, J=8.7 Hz, 2H), 6.83 (d, J=8.7 Hz, 2H), 5.00 (s, 1H), 4.69

(d, J=12.3 Hz, 1H), 4.56, (d, J=12.3 Hz, 1H), 4.46 (d, J=10.7 Hz, 1H), 4.30 (dd, J=12.6 and 5.4 Hz, 1H), 3.99 (dd, J=12.6 and 9.9 Hz, 1H), 3.77 (s, 3H), 3.73 (d, J=10.6 Hz, 1H), 3.31 (s, 3H), 3.15 (5, 3H), 3.15 (m, 1H). FAB-MS: Calcd. for $C_{23}H_{26}N_2O_5S_2$: 474.1. Found [M+H]$^+$: 475.1.

Preparation of 1,4-dimethyl-2-methylhydroxy-5-[(phenylmetoxy)methyl]-2,5-piperazidnedione-3,6-disulfide (11)

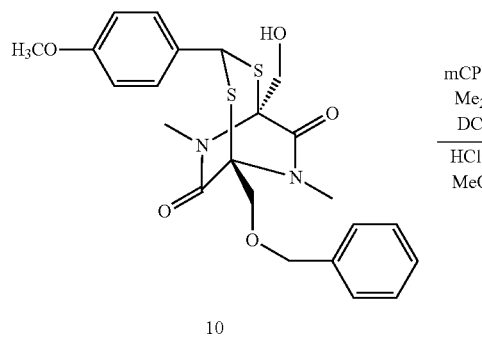

10

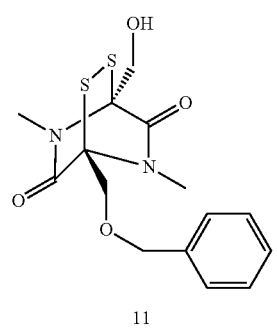

11

The purified 10 (20 mg, 0.035 mmol, 1 eq.) was dissolved in anhydrous dichloromethane (10 mL) and the solution was cooled to 0° C. To the stirred solution m-chloroperbenzoic acid (10 mg, 0.043 mmol, 1.2 eq, max. 77% pure) was added. After 10 min of stirring at 0° C., dimethyl sulfide (13 µL) was added. The solution was then treated with 16 µL of perchloric acid, in methanol (1:5). The solution was allowed to stand at room temperature for 8 h and then poured into saturated sodium bicarbonate solution. The aqueous layer was extracted with dichloromethane. The dichloromethane solution was washed with water, dried under MgSO$_4$ and concentrated under vacuum to give 18 mg of crude product. The white precipitate was washed with Et$_2$O to obtain 8 mg (71%©) of final pure product 11. $^1$H NMR (CDCl$_3$, TMS, ppm) δ: 7.38 (m, 5H), 4.76 (d, J=11.9 Hz, 1H), 4.71 (d, J=12.1 Hz, 1H), 4.36 (d, J=12.0 Hz, 1H), 4.28 (d, J=11.1 Hz, 1H), 4.24 (d, J=12.6 Hz, 1H), 4.23 (d, J=11.1 Hz, H), 3.18 (s, 3H), 3.16 (s, 3H).

Preparation of 3-(4-methoxyphenyl)-6,8-dimethyl-1,5-bis(hydoxymethyl)-2,4-dithia-6,8-diazabicyclo[3.2.2]nonane-7,9-dione (12)

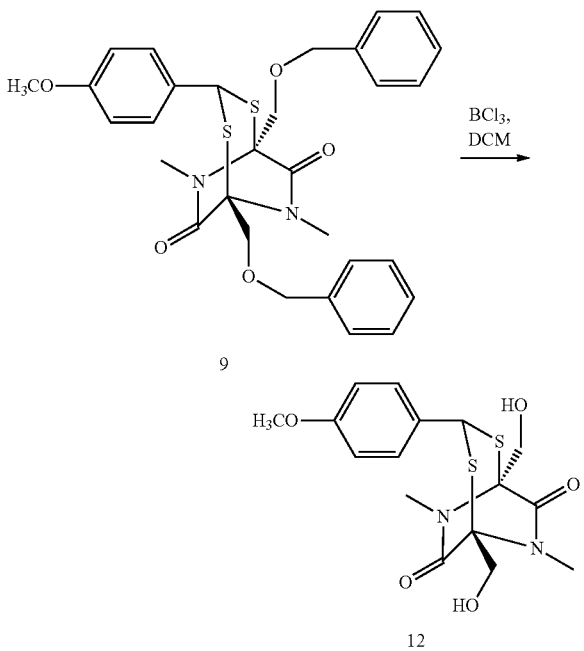

A solution of 40 mg of 9 (0.071 mmol, 1 eq.) in dichloromethane (10 mL) was cooled to 0° C. To the stirred solution 1M boron trichloride (180 µL, 0.18 mmol, 2.5 eq) in dichloromethane was added dropwise over a period of 30 seconds. The solution was allowed to be stirred at 0° C. for 10 min. and then poured into ice water. The water phase was extracted with dichloromethane. The dichloromethane solution was washed with water, dried under MgSO$_4$ and concentrated under vacuum to gain 35 mg crude product. The crystalline solid was tested on TLC and purified on column in a dichloromethane-acetone mixture (8:2), Rf 0.28, to give 25 mg of 12 (93%). $^1$H NMR (CDCl$_3$, TMS, ppm) δ: 7.31 (d, J=8.7 Hz, 2H), 6.85 (d, J=8.7 Hz, 2H), 5.01 (s, 1H), 4.64 (dd, J=9.3 and 4.8 Hz, 1H), 4.32, (dd, J=12.3 and 4.5 Hz, 1H), 4.01 (d, J=12.3 and 10.2 Hz, 1H), 3.82 (dd, J=9.3 and 4.2 Hz, 1H), 3.79 (s, 3H), 3.33 (s, 3H), 3.21 (s, 3H), 2.86 (dd, J=9.9 and 4.8 Hz, 1H), 2.56 (dd, J=9.9 and 5.1 Hz, 1H). FAB-MS: Calcd. for $C_{16}H_{20}N_2O_5S_2$: 384.0. Found [M+H]$^+$: 385.1.

Preparation of 3-(4-methoxyphenyl)-6,8-dimethyl-2,4-di[(acethyloxy)]methyl-2,4-dithia-6,8-diazabicyclo[3.2.2]nonane-7,9-dione (13)

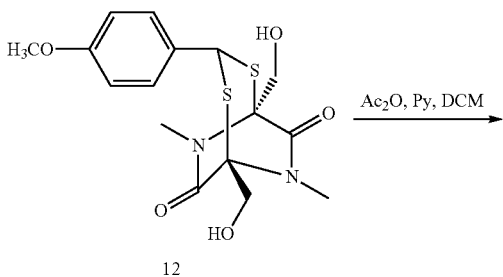

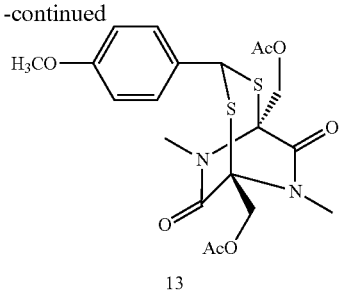

13

The diol 12 (3 mg) was dissolved in dichloromethane (500 A) and pyridine (100 μL) and Ac$_2$O (100 μL) was added. After 16 h no starting material and only a new product was detected by TLC. The solution was diluted with dichloromethane (20 mL), ice was added and the reaction was stirred for 2 h. The organic layer was washed with saturated NaHCO$_3$ solution. After evaporation under reduced pressure, the residue was purified by HPLC to give 3 mg of product 13 (82%). $^1$H NMR (CDCl$_8$, TMS, ppm) δ: 7.30 (d, J=9.0 Hz, 2H), 6.86 (d, J=8.8 Hz, 2H), 5.03 (s, 1H), 4.64 (dd, J=9.3 and 4.8 Hz, 1H), 4.32, (dd, J=12.3 and 4.5 Hz, 11), 4.01 (d, J=12.3 and 10.2 Hz, 1H), 3.82 (dd, J=9.3 and 4.2 Hz, 1H), 3.79 (s, 3H), 3.33 (s, 3H), 3.21 (s, 3H), 2.86 (dd, J=9.9 and 4.8 Hz, 1H), 2.56 (dd, J=9.9 and 5.1 Hz, 1H).

Preparation of 1,4-dimethyl-3,6-di(acethyloxy)methyl-2,5-piperazidenedione-3,6-disulfide (14)

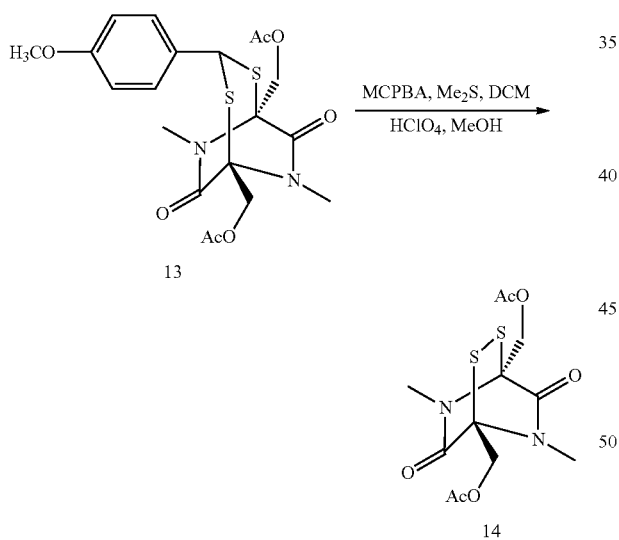

The purified 13 (30 mg, 0.055 mmol, 1 eq.) was dissolved in anhydrous dichloromethane (8 mL) and the solution was cooled to 0° C. To the stirred solution m-chloroperbenzoic acid (17 mg, 0.077 mmol, 1.4 eq, max. 77% purity) was added. After 10 min of stirring at 0° C., dimethyl sulfide (10 DO was added. The solution was then treated with 20 μL of perchloric acid, in methanol (1:5). The solution was allowed to stand at room temperature for 18 h and then poured into saturated sodium bicarbonate solution. The aqueous layer was extracted with dichloromethane. The dichloromethane solution was washed with water, dried under MgSO$_4$ and concentrated in vacuo. The solid residue was purified by HPLC to give 14, yield 7 mg (31%). $^1$H NMR (CDCl$_3$, TMS, ppm) δ: 4.97 (d, J=12.6 Hz, 2H), 4.76 (d, J=12.6 Hz, 2H), 3.13 (s, 6H), 2.16 (s, 6H). HRFAB-MS: Calcd. for C$_{12}$H$_{16}$N$_2$O$_6$S$_2$: 348.045. Found [M+H]$^+$: 349.053.

Preparation of 3-(4-methoxy-phenyl)-6,8-dimethyl-1-[(phenylmetoxy)methyl]-5[(4-bromomethylphenyl)methyl]-2,4-dithia-6,8-diaza-bicyclo[3.2.2]nonane-7,9-dione (15)

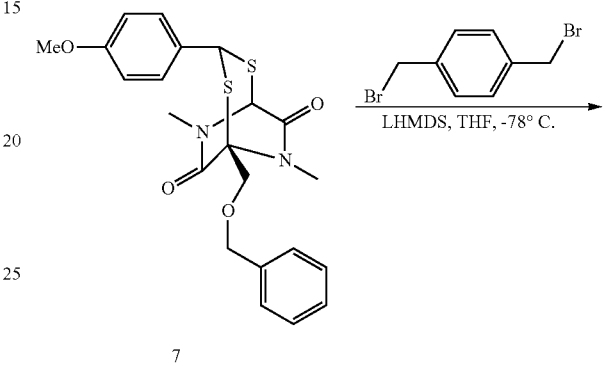

7

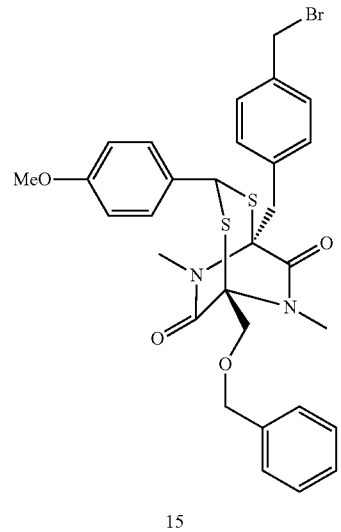

15

The protected thioacetal (444 mg, 1 mmol, 1 eq.) and dibromo-p-xylene (1.58 g, 6 mmol, 6 eq.) was dissolved in anhydrous THF (80 mL) and cooled to −78° C. Next, 1 M solution of LHMDS in THF (1.3 mL, 1.3 mmol, 1.3 eq) was added dropwise over a period of 3 min with stirring. Stirring was continued at −78° C. for an additional 5 min following the addition. The cooling bath was then removed, and the mixture was allowed to warm and stand at room temperature for 3 h. Saturated NaCl solution was added into the reaction mixture and the red solution was extracted with CH$_2$Cl$_2$ (3×50 mL). The combined organic extracts were dried over anhydrous MgSO$_4$, filtered and concentrated under reduced pressure.

The solid residue was separated by column chromatography on silica gel using CH$_2$Cl$_2$ to give product 388 mg (77% yield). $^1$H NMR (CDCl$_3$, TMS, ppm) δ: 7.33 (m, 9H), 7.13 (d, J=8.4 Hz, 2H), 6.85 (d, J=8.8 Hz, 2H), 5.08 (s, 1H), 4.78 (d, J=12.0 Hz, 1H), 4.56 (d, J=12.0 Hz, 1H), 4.46 (s, 2H), 4.37 (d, J=16.8 Hz, 1H), 4.32 (d, J=10.5 Hz, 1H), 3.85 (d, J=10.5 Hz, 1H), 3.80 (s, 3H), 3.35 (s, 3H), 3.15 (d, J=16.8 Hz, 1H), 2.97 (s, 3H). $^{13}$C NMR (CDCl$_3$, ppm) δ:165.72, 165.46, 160.55, 137.39, 136.30, 135.50, 130.46, 129.38, 128.75, 128.45, 127.93, 127.78, 126.52, 114.39, 74.02, 73.39, 71.07, 68.68, 55.37, 51.24, 40.21, 33.07, 29.80, 28.08. FABMS: Calcd. for C$_{30}$H$_{31}$BrN$_2$O$_4$S$_2$: 626.1. Found [M+H]$^+$: 627.0.

Preparation of 3-(4-methoxy-phenyl)-6,8-dimethyl-1-[(phenylmetoxy)methyl]-5[(4-{3-(4-methoxyphenyl)-6,8-dimethyl-1-[(phenylmetoxy)methyl]-2,4-dithia-6,8-diazabicyclo[3.2.2]nonane-7,9-dione-5-yl}methylphenyl)methyl]-2,4-dithia-6,8-diazabicyclo[3.2.2]nonane-7,9-dione (16) and bis{3-(4-methoxy-phenyl)-6,8-dimethyl-1-[(phenylmetoxy)methyl]-2,4-dithia-6,8-diaza-bicyclo[3.2.2]nonane-7,9-dione-5[(4-methylphenyl)methyl]} (21)

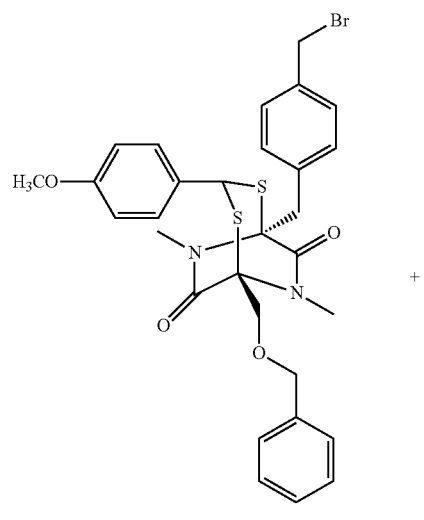

15

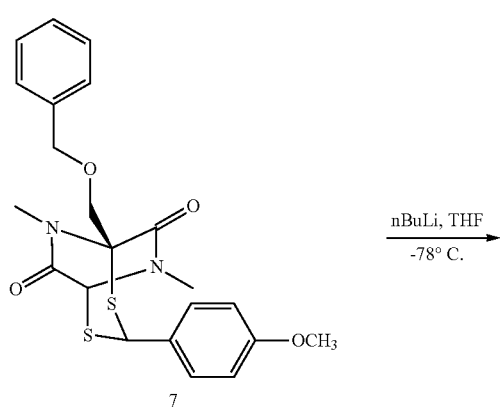

7

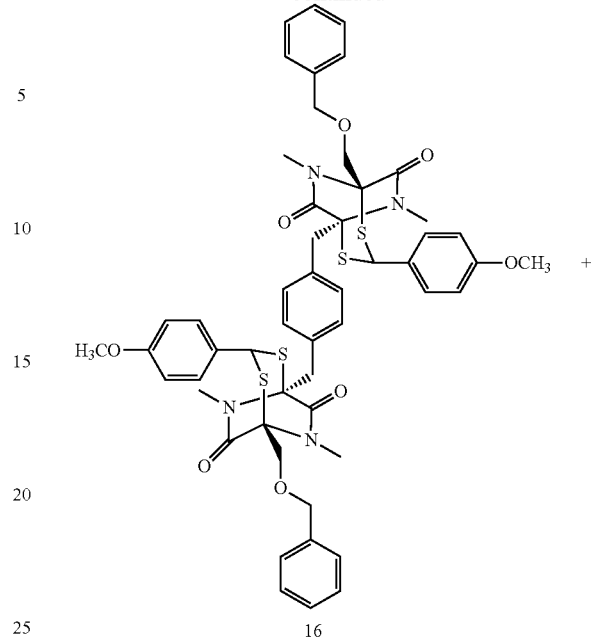

16

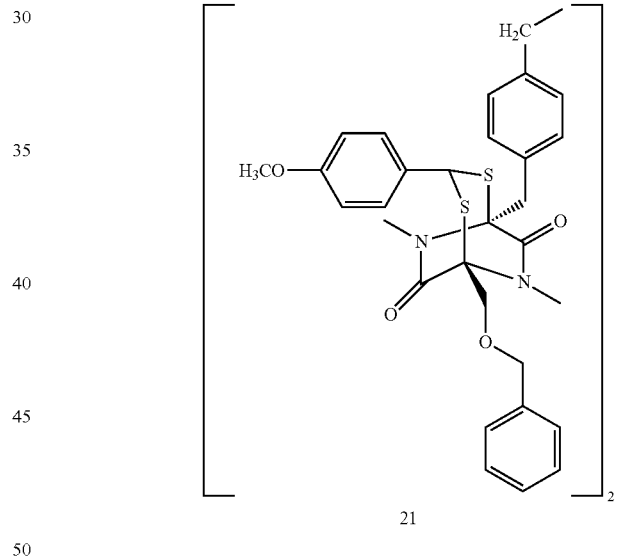

21

A solution of 196 rug of 7 (0.44 mmol, 1 eq.) as well as 413 mg of 15 (0.66 mmol, 1.5 eq.) in anhydrous THF (60 mL) was cooled to −78° C. To the stirred solution 2.5 M n-butyllithium in hexane (264 μL, 0.66 mmol, 1.5 eq.) was added dropwise over a period of 30 sec. After the mixture was stirred for 5 min at −78° C. the reaction was checked by TLC and it looked like there was a new spot but a lot of starting materials. Gradually, additional 150 μL of n-butyllithium was added, but after each portions (~30 μL) the reaction mixture was tested by TLC. Finally the TLC showed no starting material of 7. The mixture was allowed to warm to room temperature while it was stirred. It took about 30 min. The TLC shows one major product and a little (~less than 5%, dibromide) starting material. The organic solution was diluted with 150 mL dichloromethane and washed saturated NaCl solution several times.

The organic solution was dried under MgSO₄ and concentrated under vacuum. The solid residue was separated on column, in a mixture of hexane-EtOAc, 6:4. There were two new dimers 21 (54 mg, 16%, Rf 0.42, HRFAB-MS: Calcd. for $C_{60}H_{62}N_4O_8S_4$ 1094.345. Found [M+H]⁺ 1095.356) and 16 (107 mg, 36%, Rf 0.35, FAB-MS: Calcd. for $C_{52}H_{54}N_4O_8S_4$: 990.282. Found [M+H]⁺: 991.291). next step was carried out starting from this crude material.

5,5'-(1,4-Phenylenebis(methylene))bis(1-(benzyloxymethyl)-3-(4-methoxyphenyl)-6,8-dimethyl-2,4-dithia-6,8-diazabicyclo[3.2.2]nonane-7,9-dime) (16)

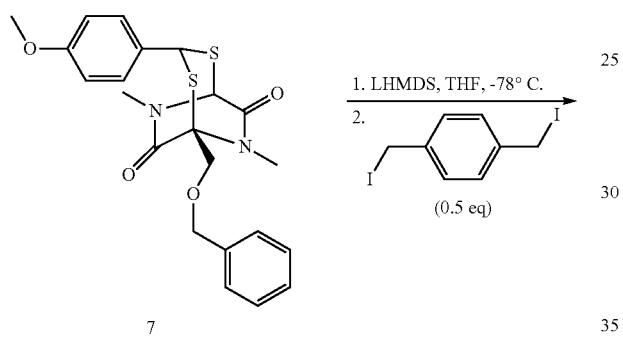

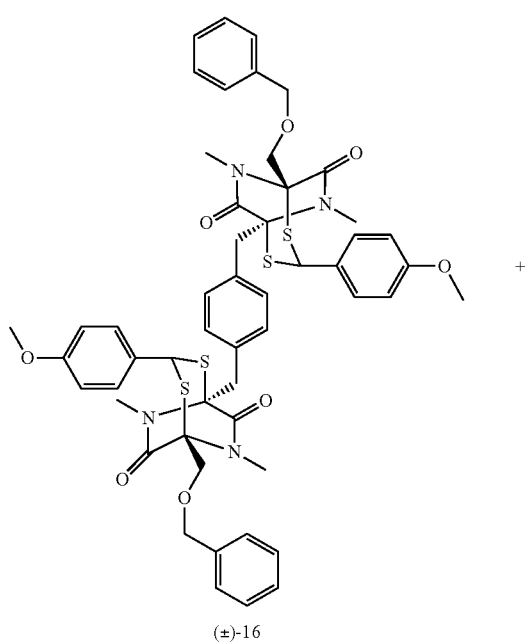

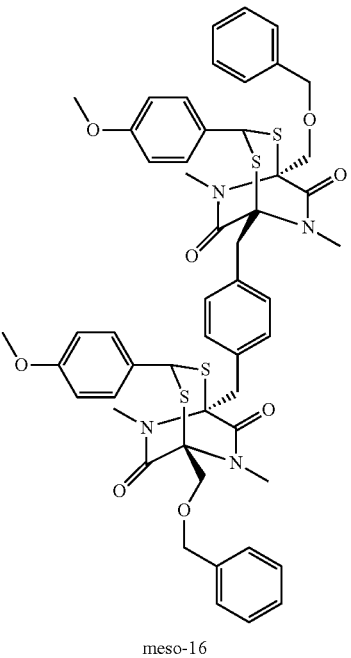

A solution of 7 (0.33 g, 0.75 mmol) in dry THF (15 mL) was cooled to −78° C. Next, 1 M solution of LHMDS in THF (1.0 mL, 1.0 mmol) was added dropwise over a period of 2 min with stirring. The α,α'-diiodo-p-xylene (88 mg, 0.25 mmol), dissolved in 2 mL of THF was then added dropwise into the reaction mixture and the solution was allowed to warm up to room temperature for 3 h. Water was added into the reaction and the mixture was extracted with dichloromethane (3×50 mL). The combined organic extracts were dried over anhydrous MgSO₄, filtered and concentrated under reduced pressure. A mixture of diastereoisomers meso-16 and (±)-16 (0.20 g, 80%) was separated by column chromatography on silica gel using CH₂Cl₂:Hexane:EtOAc=5:4:1 as an eluent. For (±)-16 ¹H NMR (CDCl₃, ppm) δ: 7.33 (m, 14H), 7.07 (s, 4H), 6.84 (d, J=8.8 Hz, 4H), 5.06 (s, 2H), 4.78 (d, J=12.20 Hz, 2H), 4.56 (d, J=12.20 Hz, 2H), 4.36 (d, J=16.39 Hz, 2H), 4.28 (d, J=10.67 Hz, 2H), 3.82 (d, J=10.67 Hz, 2H), 3.80 (s, 6H), 3.34 (s, 6H), 3.08 (d, J=16.39 Hz, 2H), 2.94 (s, 6H). ¹³C NMR (CDCl₃, ppm) δ: 165.76, 165.50, 160.45, 137.27, 133.72, 130.43, 128.78, 128.44, 127.92, 127.84, 126.52, 114.31, 73.97, 73.39, 71.00, 68.51, 55.35, 51.03, 40.23, 29.80, 28.08. HRMS (FAB) m/z-calcd. for $C_{52}H_{55}N_4O_8S_4^+$[M+H⁺]: 991.290. Found: 991.291.

(±)-5,5'-(1,4-Phenylenebis(methylene))bis(1-(hydroxymethyl)-3-(4-methoxyphenyl)-6,8-dimethyl-2,4-dithia-6,8-diazabicyclo[3.2.2]nonane-7,9-dione), (±)-17

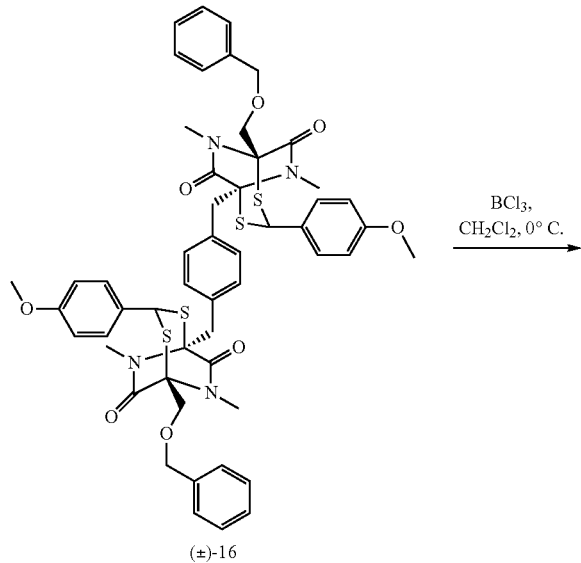

(±)-16

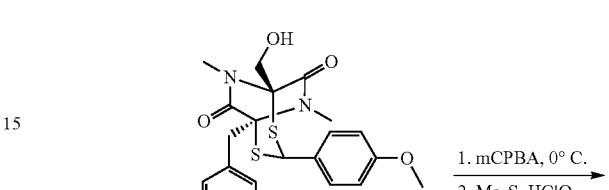

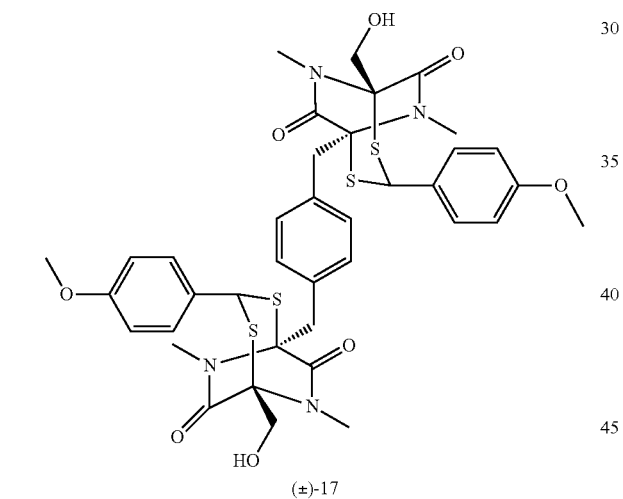

(±)-17

To a solution of (±)-16 (0.13 g, 0.13 mmol) in dichloromethane (10 mL) cooled to 0° C., boron trichloride (1M solution in $CH_2Cl_2$, 320 µL, 0.32 mmol) was added dropwise with stirring. The solution was stirred at 0° C. for additional 10 min and then poured into ice-cold water (10 mL) and extracted with dichloromethane (25 mL). The organic layer was washed twice with water, dried with anhydrous $MgSO_4$ and concentrated under reduced pressure to obtain crude product as a white solid. The crude product purified by column chromatography (silica gel, $CH_2Cl_2$/EtOAc=7:3) to afford (±)-17 (93 mg, 91%). $^1$H NMR (CDCl$_3$, ppm) δ: 7.32 (d, J=8.8 Hz, 4H), 7.03 (d, J=8.8 Hz, 4H), 5.08 (s, 2H), 4.37 (d, J=16.24 Hz, 1H), 4.33 (dd, J=12.60 Hz and 5.54 Hz, 2H), 4.05 (dd, J=12.6 Hz and 9.93 Hz, 2H), 3.81 (s, 6H), 3.42 (s, 6H), 3.06 (d, J=16.24 Hz, 2H), 2.95 (dd, J=9.93 Hz and 5.54 Hz, 2H), 2.91 (s, 6H). $^{13}$C NMR (CDCl$_3$, ppm) δ:166.67, 165.83, 160.45, 133.70, 130.42, 128.80, 126.45, 114.39, 73.20, 71.12, 62.98, 55.39, 50.98, 40.42, 29.79, 27.98. HRMS (ESI) m/z: calcd. for $C_{38}H_{43}N_4O_8S_4^+$[M+H$^+$]: 811.196. Found: 811.195.

(±)-4,4'-(1,4-Phenylenebis(methylene))bis(1-(hydroxymethyl)-5,7-dimethyl-2,3-dithia-5,7-diazabicyclo[2.2.2]octane-6,8-dione), (±)-18, LS69

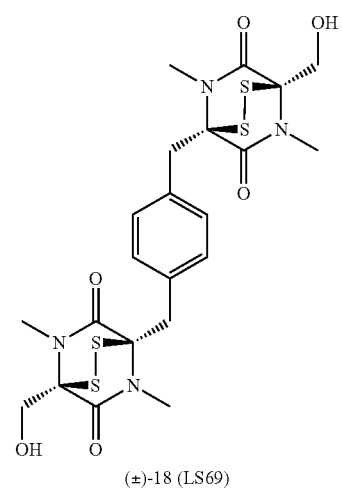

(±)-18 (LS69)

m-Chloroperbenzoic acid (22 mg, 77% max content, 0.10 mmol) was added to an ice-cold solution of (±)-17 (33 mg, 0.040 mmol) in anhydrous dichloromethane (10 mL) with stirring. After 10 min of stirring at 0° C., dimethyl sulfide (10 µl) was added, followed by treatment with 20 µL of a solution of 70% perchloric acid in methanol (1:5). The solution was allowed to stand at room temperature for 9 h. The reaction mixture was poured into a saturated sodium bicarbonate. The solution was extracted with dichloromethane (3×30 mL). The combined organic extracts were combined, dried over anhydrous $MgSO_4$, filtered and concentrated under reduced pressure. The glassy residue was purified by column chromatography (silica gel, $CH_2Cl_2$/EtOAc=6:4) to afford (±)-18 (LS69) (11 mg, 33%). $^1$H NMR (DMSO-D6, ppm) δ: 7.24 (s, 4H), 5.90 (t, J=5.50 Hz, 2H), 4.33 (dd, J=12.83 Hz and 5.50 Hz, 2H), 4.23 (dd, J=12.83 Hz and 5.50 Hz, 2H), 3.89 (d, J=16.04 Hz, 21), 3.73 (d, J=16.04 Hz, 2H), 3.13 (s, 6H), 2.82 (s, 6H). $^{13}$C NMR (CDCl$_3$, ppm) δ: 165.35, 164.92, 133.45, 128.89, 76.33, 75.91, 59.12, 35.50, 28.31, 27.89. HRMS (FAB) m/z: calcd. for $C_{22}H_{26}N_4O_6S_4Na^+$ [M+Na$^+$]: 593.063. Found: 593.063.

5,5'((Ethane-1,2-diylbis(4,1-phenylene))bis(methyl-ene))bis(1-((benzyloxy)methyl)-3-(4-methoxyphenyl)-6,8-dimethyl-2,4-dithia-6,8-diazabicyclo[3.2.2]nonane-7,9-dione) (21)

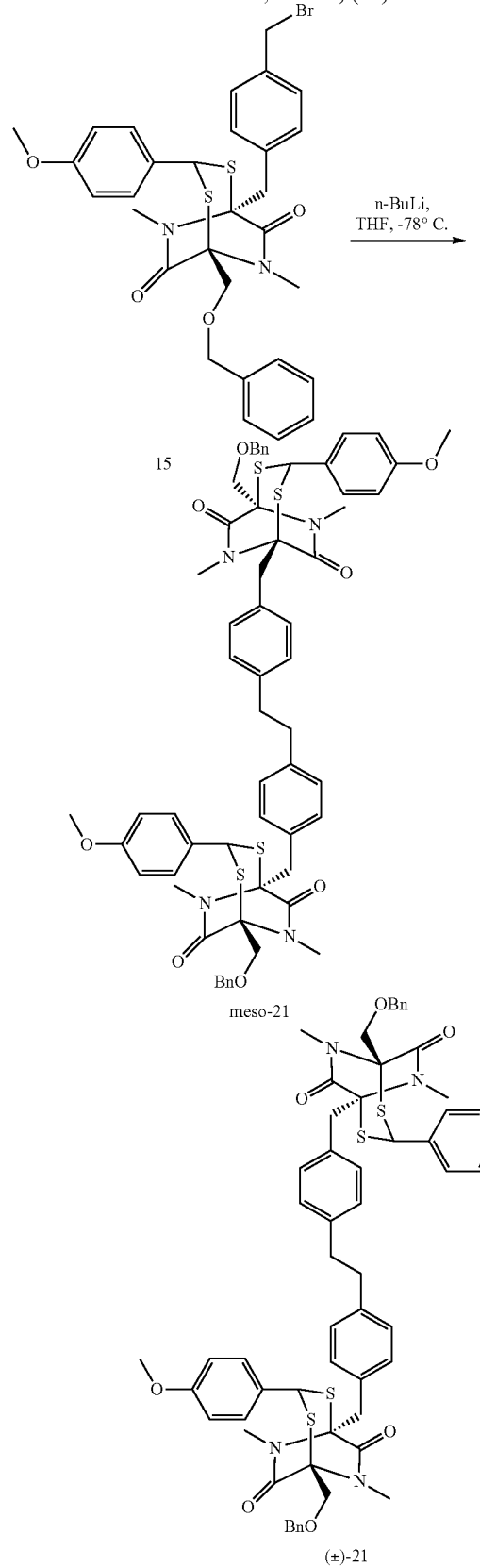

A solution of 15 (2.14 g, 3.40 mmol, 1.0 eq.) was cooled to −78° C. and 1.6 M n-butyllithium in hexane (2.77 mL, 4.43 mmol, 1.3 eq.) was added dropwise upon stirring over a period of 2 min. Following the addition, the stirring was continued at −78° C. for an additional 5 min. The cooling bath was then removed and the mixture was allowed to gradually warm up to room temperature over the period of 3 h. The reaction mixture was the poured into ice-cold water and extracted with dichloromethane (3×50 mL). The combined organic extracts were dried over anhydrous $MgSO_4$, filtered and concentrated under reduced pressure to yield product as a mixture of meso-21 and (±)-21. The products were purified from reactants by column chromatography on silica gel using $CH_2Cl_2$:Hexane:EtOAc=5:4:1 as an eluent and were used as a mixture in the next step. Total yield: 638 mg (34%). A sample of the obtained product was subjected to a second column chromatography on silica gel using the same eluent system, where a portion of racemic (±)-21 was separated from the mixture of (±)-21 and meso-21 and used for analysis. Analysis data for (±)-21: $^1$H NMR ($CDCl_3$, ppm) δ: 7.34 14H), 7.08 (q, 8H), 6.85 (d, J=8.8 Hz, 4H), 5.07 (s, 2H), 4.78 (d, J=12.2 Hz, 2H), 4.56 (d, J=12.2 Hz, 2H), 4.36 (d, J=16.8 Hz, 2H), 4.31 (d, J=10.7 Hz, 2H), 3.84 (d, J=10.7 Hz, 2H), 3.80 (s, 6H), 3.34 (s, 6H), 3.10 (d, J=16.8 Hz, 2H), 2.97 (d, 6H), 2.86 (s, 4H). $^{13}$C NMR ($CDCl_3$, ppm) δ: 165.76, 165.63, 160.51, 140.26, 137.44, 132.66, 130.46, 128.69, 128.42, 127.89, 127.76, 126.67, 114.36, 74.00, 73.56, 71.08, 68.71, 55.36, 51.23, 40.24, 37.27, 29.78, 28.07. HRFABMS: Calcd. for $C_{60}H_{62}N_4O_8S_4$ 1094.345. Found [M+H]$^+$ 1095.356.

5,5'-((Ethane-1,2-diylbis(4,1-phenylene))bis(methyl-ene))bis(1-(hydroxymethyl)-3-(4-methoxyphenyl)-6,8-dimethyl-2,4-dithia-6,8-diazabicyclo[3.2.2]nonane-7,9-dione) (22)

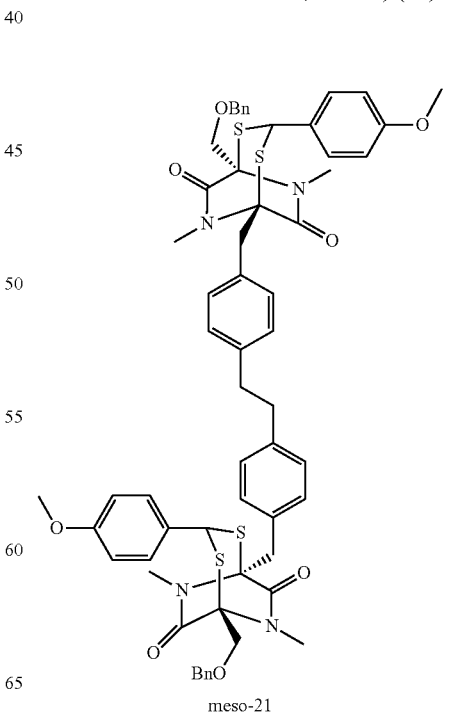

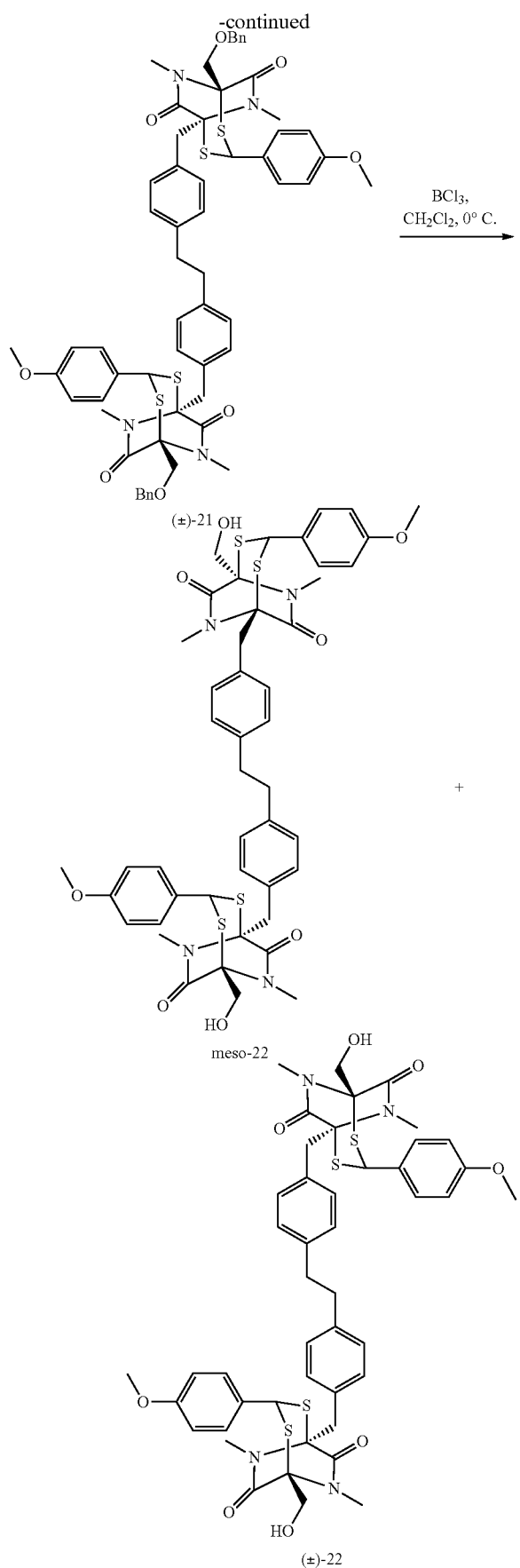

To an ice-cooled solution of 21 (125 mg, 0.126 mmol, 1 eq.) in dichloromethane, a 1 M solution of boron trichloride in dichloromethane (320 μL, 0.32 mmol, 2.5 eq) was added dropwise while stirring. The mixture was allowed to stand at 0° C. for 15 min and then was poured into the ice-cold water. The aqueous layer was extracted. with dichloromethane (3×50 mL). The combined organic extracts were dried over anhydrous magnesium sulfate, filtered and evaporated under reduced pressure. The crude reaction mixture was purified by flash column chromatography to give 78 mg of product mixture of meso-22 and (±)-22 as a white solid (75% combined yield). The mixture of meso-22 and (±)-22 was further purified on silica gel column using gradient of EtOAC in dichloromethane from 10% to 50% in order to separate meso-22 and (±)-22. Analytical data for (±)-22: $^1$H NMR (CDCl$_3$, ppm) δ: 7.32 (d, 4H), 6.93 (d, 4H) 6.89 (d, 4H), 6.86 (d, 4H), 5.08 (s, 2H), 4.47 (dd, J=6 Hz, 13 Hz, 2H), 4.37 (d, 2H), 4.26 (m, 2H), 3.98 (dd, J 10 Hz, 13 Hz, 2H), 3.80 (s, 6H), 3.41 (s, 6H), 2.98 (d, 2H), 2.84 (s, 6H), 2.69 (d, 2H). $^{13}$C NMR (DMSO-d$_6$, ppm) δ:165.42, 165.19, 160.06, 140.00, 132.93, 130.52, 128.53, 128.42, 126.82, 114.38, 73.47, 71.51, 60.79, 55.29, 49.91, 40.14, 36.36, 29.60, 27.96. FABMS: Calcd. for C$_{46}$H$_{50}$N$_4$O$_8$S$_4$: 914.3. Found [M+Na]$^+$: 936.9. Analytical data for meso-7: $^1$H NMR (CDCl$_3$, ppm) δ: 7.33 (d, 4H), 7.02 (d, 4H) 6.99 (d, 4H), 6.86 (d, 4H), 5.09 (s, 2H), 4.35 (dd, J=10 Hz, 13 Hz, 2H), 4.37 (d, 2H), 3.11 (m, 2H), 4.04 (dd, J=10 Hz, 13 Hz, 2H), 3.81 (s, 6H), 3.41 (s, 6H), 2.91 (s, 6H), 2.85 (s, 4H). $^{13}$C NMR (DMSO-d$_6$, ppm) δ:165.47, 165.24, 160.10, 140.04, 132.96, 130.56, 128.55, 128.48, 126.85, 114.42, 73.50, 71.55, 60.83, 55.34, 49.96, 40.14, 36.42, 29.63, 28.00. FABMS: Calcd. for C$_{46}$H$_{50}$N$_4$O$_8$S$_4$: 914.3. Found [M+Na]$^+$: 936.9.

(±)-4,4'-((ethane-1,2-diylbis(4,1-phenylene))bis(methylene))bis(1-(hydroxymethyl)-5,7-dimethyl-2,3-dithia-5,7-diazabicyclo[2.2.2]octane-6,8-dione) ((±)-LS72, (±)-23)

-continued

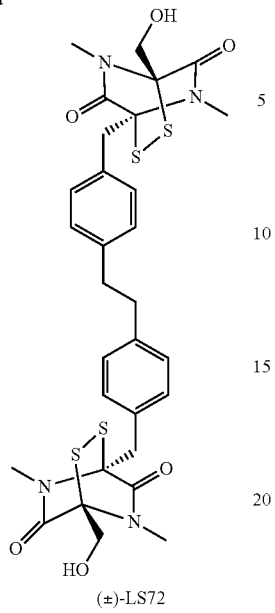

(±)-LS72

A 50 mL round-bottom flask was charged with the dithioacetal (±)-22 (20 mg, 0.022 mmol) which was dissolved in 35 mL of $CH_2Cl_2$. The flask was cooled to 0° C. and excess of m-chloroperbenzoic acid (15 mg, 77% content, 0.07 mmol) was added. After 30 min of stirring at 0° C. the ice bath was removed and dimethyl sulfide (6.4 µL, 0.09 mmol) was added, followed by the addition of trifluoroacetic acid (126 µL). The reaction mixture was stirred at room temperature for 3 h. An aqueous saturated sodium bicarbonate (15 mL) was added to the reaction mixture and the organic layer was separated. The aqueous layer was further extracted with dichloromethane (20 mL). The combined organic layers were dried over anhydrous $Mg_2SO_4$, filtered and concentrated under reduced pressure. The glassy residue was dissolved in 50% DMSO in acetonitrile and purified by reverse-phase HPLC to obtain (±)-LS72 ((±)-23) in 61% yield. Alternatively, to purify the larger amount of (±)-LS72, a post work-up crystallization of the reaction mixture was performed. Briefly, to the residue (25 mg) acetonitrile was added (2 mL) and the mixture was briefly sonicated at room temperature to dissolve the residue. The mixture was cooled to 4° C. and maintained at that temperature for 2 h, after which it was stored overnight at −20° C. The supernatant was removed by filtration and the white crystals were washed with acetonitrile cooled to −20° C. The supernatant was recrystallized again by employing the above procedure. The purity of the final product was verified by analytical HPLC using gradient of acetonitrile (40%-95% over 20 min) in an aqueous phase that contained 0.05% v/v of trifluoroacetic acid. $^1$H NMR ($CDCl_3$, ppm) δ: 7.19 (d, 4H), 7.07 (d, 4H), 4.39 (d, 2H), 4.30 (d, 2H), 4.04 (d, 2H), 3.59 (d, 2H), 3.21 (s, 6H), 2.96 (s, 6H), 2.86 (m, 4H). $^{13}$C NMR ($CDCl_3$, ppm) δ: 166.85, 165.57, 140.65, 131.58, 129.07, 128.81, 75.80, 75.18, 61.21, 37.22, 36.51, 28.59, 27.53. HR-ESIMS: Calcd. for $C_{30}H_{34}N_4O_6S_4$+H$^+$: 675.14. Found [M+H]$^+$: 675.1401.

Meso-4,4'-((ethane-1,2-diylbis(4,1-phenylene))bis (methylene))bis(1-(hydroxymethyl)-5,7-dimethyl-2, 3-dithia-5,7-diazabicyclo[2.2.2]octane-6,8-dione) (meso-LS72, meso-23)

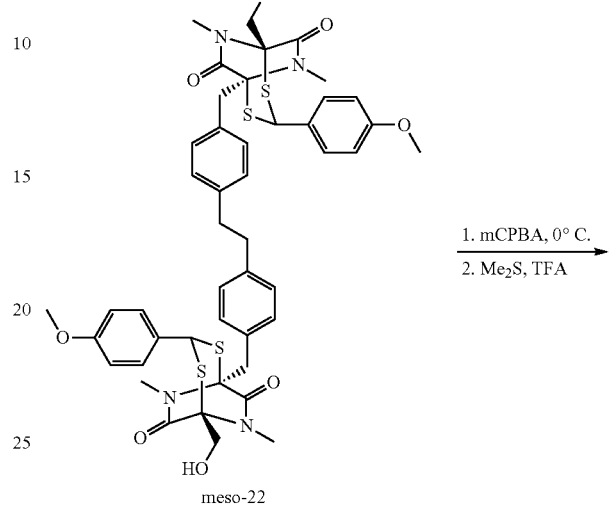

meso-22

1. mCPBA, 0° C.
2. $Me_2S$, TFA

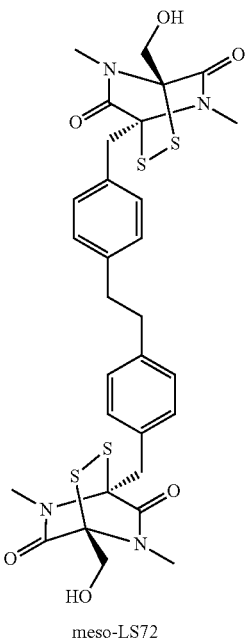

meso-LS72

Meso-LS72 (meso-23) was prepared from dithioacetal meso-22 by following the procedure analogous to that of (±)-7. Yield 60%, $^1$H NMR ($CDCl_3$, ppm) δ: 7.21 (d, 4H), 7.09 (d, 4H), 4.39 (d, 2H), 4.31 (d, 2H), 4.04 (d, 2H), 3.59 (d, 2H), 3.21 (s, 6H), 2.97 (s, 6H), 2.87 (m, 4H). $^{13}$C NMR ($CDCl_3$, ppm) δ: 166.92, 165.58, 140.73, 131.59, 129.16, 128.77, 75.81, 75.15, 61.26, 37.15, 36.53, 28.61, 27.52. HR-ESIMS: Calcd. for $C_{30}H_{34}N_4O_6S_4$+H$^+$: 675.14. Found [M+H]$^+$: 675.1411.

Chiral Separation of (±)-22:

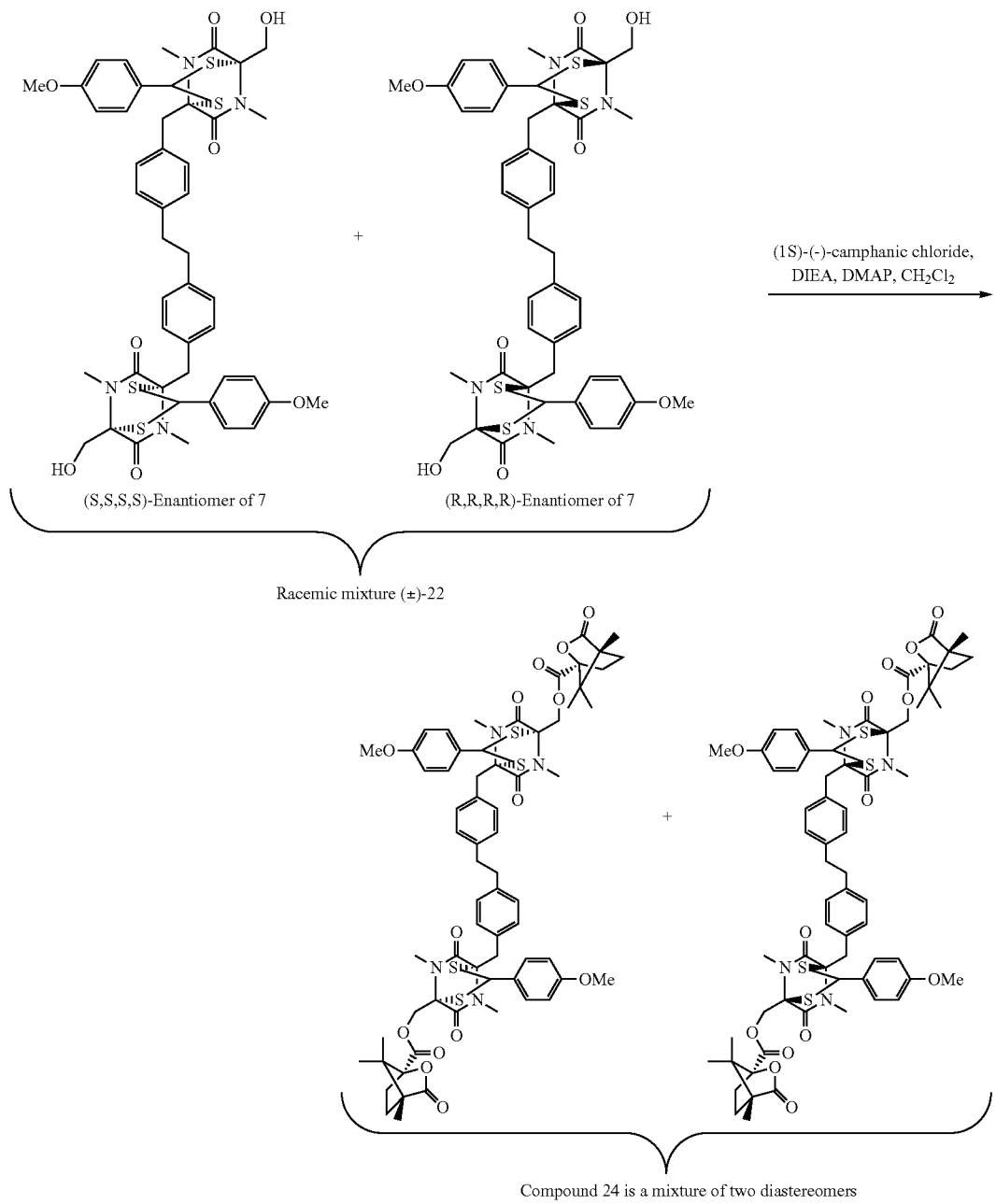

Compound 24 is a mixture of two diastereomers

A round-bottom flask was charged with (±)-22 (20 mg, 0.22 mmol) and 5 mL of dichloromethane. To this mixture, (1S)-(−)-camphanic chloride (71 mg, 0.3 mmol, 1.4 eq.), 4-dimethylaminopyridine (0.8 mg, 0.007 mmol, 0.03 eq.) and N,N-diisopropylethylamine (150 μL, 0.86 mmol, 3.9 eq.) were added sequentially with stirring. The stirring was maintained for 1 h at room temperature. The reaction mixture was washed with OA M HCl (5 mL) and dried over anhydrous $MgSO_4$. The solvent was removed under reduced pressure to obtain crude 24 (23 mg, 83% total yield). The two diastereomers of 24 were separated by column chromatography using initial solvent system of 10% $CH_2Cl_2$ in hexanes and gradually increasing the amounts of $CH_2Cl_2$ and EtOAc to final solvent system of hexanes EtOAc $CH_2Cl_2$=4:3:3. The two fractions obtained were named dst1-24 (13 mg recovered) and dst2-24 (10 mg recovered), respectively. Data from analysis of dst1-24: $^1$H NMR ($CDCl_3$, ppm) δ: 7.33 (d, 2H), 7.09 (d, 2H), 7.00 (d, 2H), 6.87 (d, 2H), 5.31 (d, 1H), 5.11 (s, 1H), 4.42 (d, 1H), 4.36 (d, 1H), 3.81 (s, 3H), 3.40 (s, 3H), 3.08 (d, 1H), 2.88 (s, 3H), 2.83 (br, 2), 2.40 (m, 1H), 2.02 (m, 1H), 1.89 (m, 1H), 1.68 (m, 1H), 1.09 (s, 3H), 0.97 (s, 3H), 0.81 (s, 3H). $^{13}$C NMR ($CDCl_3$, ppm) δ: 177.78, 166.42, 165.86, 164.81, 160.94, 140.68, 132.58, 130.79, 129.03, 128.42, 126.10, 114.69, 91.01, 73.54, 70.13, 63.05, 55.62, 55.10, 54.62, 51.83, 40.28, 37.53, 30.90, 29.87, 28.92, 28.47, 16.77, 16.67, 10.05. Data from analysis of dst2-24: $^1$H NMR (CDCl₃, ppm) δ: 7.33 (d, 2H), 7.09 (d, 2H), 7.02 (d, 2H), 6.87 (d, 2H), 5.28 (d, 1H), 5.10 (s, 1H), 4.43 (d, 1H), 4.35 (d, 1H), 3.81 (s, 3H), 3.36 (s, 3H), 3.12 (d, 1H), 2.93 (s, 3H), 2.84 (br, 2), 2.33 (m, 1H), 2.05 (m, 1H), 1.90 (m, 1H), 1.71 (m, 1H), 1.10 (s, 3H), 0.94 (s, 3H), 0.91 (s, 3H). ¹³C NMR (CDCl₃, ppm) δ: 178.12, 166.16, 165.89, 164.74, 160.96, 140.57, 132.73, 130.78, 128.90, 128.42, 126.21, 114.70, 90.87, 73.46, 70.03, 63.16, 55.61, 54.95, 54.47, 51.76, 40.19, 37.44, 30.97, 29.92, 29.19, 28.39, 16.74, 16.64, 9.96.

purification on reverse phase HPLC. Each of the reaction of the two diastereomers yielded two enantiomers en1-22 or ent2-22 (6 mg each enantiomer recovered, 74%). CD spectra confirmed the enantiomeric relationship of the two products.

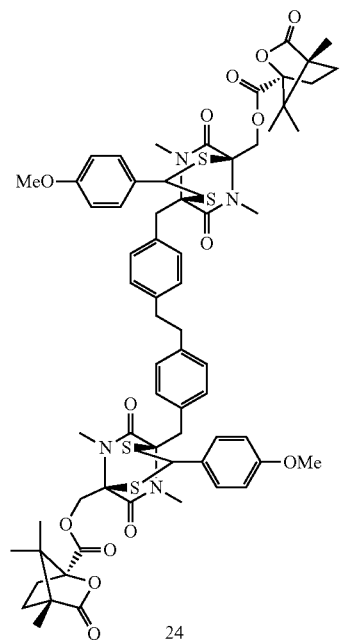

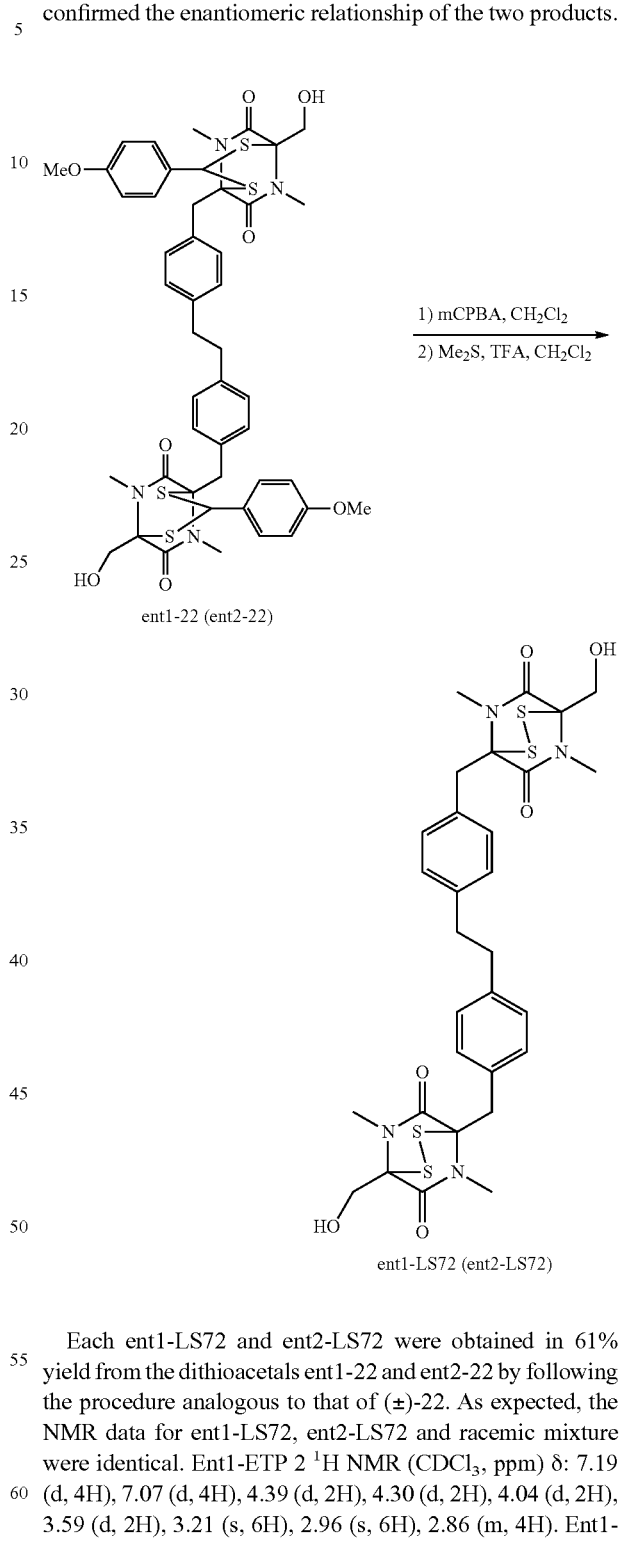

To 10 mg of each diastereomer of 24, 1 mL of saturated solution of sodium bicarbonate in methanol was added. The reaction was stirred for 24 h at room temperature. Reaction was initially purified by short silica gel column followed by Each ent1-LS72 and ent2-LS72 were obtained in 61% yield from the dithioacetals ent1-22 and ent2-22 by following the procedure analogous to that of (±)-22. As expected, the NMR data for ent1-LS72, ent2-LS72 and racemic mixture were identical. Ent1-ETP 2 ¹H NMR (CDCl₃, ppm) δ: 7.19 (d, 4H), 7.07 (d, 4H), 4.39 (d, 2H), 4.30 (d, 2H), 4.04 (d, 2H), 3.59 (d, 2H), 3.21 (s, 6H), 2.96 (s, 6H), 2.86 (m, 4H). Ent1-LS72: Calcd. for C₃₀H₃₄N₄O₆S₄+H⁺: 675.14. Found [M+H]⁺: 675.1416. ent2-LS72: Calcd. for C₃₀H₃₄N₄O₆S₄+ H⁺: 675.14. Found [M+H]⁺: 675.1316. CD spectra for ent1-LS72 and ent2-LS72 confirmed the enantiomeric relationship.

Preparation of 3-(4-methoxyphenyl)-6,8-dimethyl-1-(phenylmethyl)2,4-dithia-6, 8-diazabicyclo[3.2.2]nonane-7,9-dione (26)

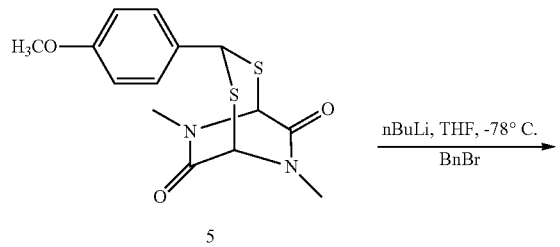

5

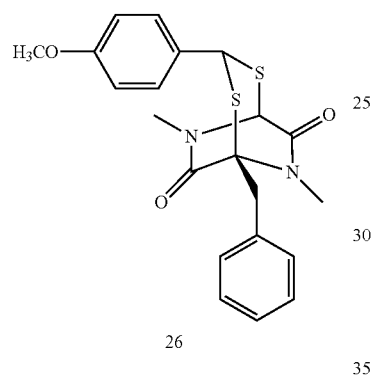

26

Thioacetal 5 (194 mg, 0.6 mmol, 1 eq.) was dissolved in anhydrous THF (25 mL) and the solution was cooled to −78° C. To the stirred solution 1.54 M n-butyllithium in hexane (545 μL, 0.84 mmol, 1.4 eq.) was added dropwise over a period of 1 min. After 30 second benzyl bromide (356 μL, 513 mg, 3 mmol, 5 eq) was added to the stirred mixture over a period of 30 sec. After the mixture was stirred for 8 min at −78° C. the resulting red, cloudy solution was allowed to warm to room temperature and was stirred. It took about 30 min. The TLC shows one major product and a little (~5%) of starting material. Saturated NaCl solution was added into the reaction mixture and the solution was extracted with dichloromethane. The organic solution was washed with water twice, dried under $MgSO_4$ and concentrated under vacuum. The oily residue was treated with hexane. One part of the material got solid and the hexane solution was removed. The yellow solid was washed again with hexane and dried under vacuum. The solid crude material was dissolved in dichloromethane (2 mL), methanol (4 mL) and hexane (about 20 mL) was added. The white precipitate was filtered off to give the pure product 100 mg of 26 (40.8%). $^1$H NMR ($CDCl_3$, TMS, ppm) δ: 7.36 (d, J=8.7 Hz, 2H), 724 (m, 5l), 6.88 (d, J=8.7 Hz, 2H), 5.19 (s, 1H), 5.10 (s, 1H), 4.15 (d, J=16.6 Hz, 1H), 3.82 (s, 3H), 3.25 (d, J=16.5 Hz, 1H), 3.15 (s, 3H), 3.11 (5, 1H).

Preparation of 3-(4-methoxyphenyl)-6,8-dimethyl-1-[(phenylmetoxy)methyl]-5-(phenylmethyl)-2,4-dithia-6,8-diazabicyclo[3.2.2]nonane-7,9-dione (27)

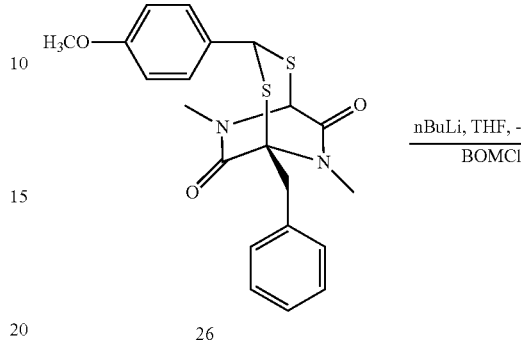

26

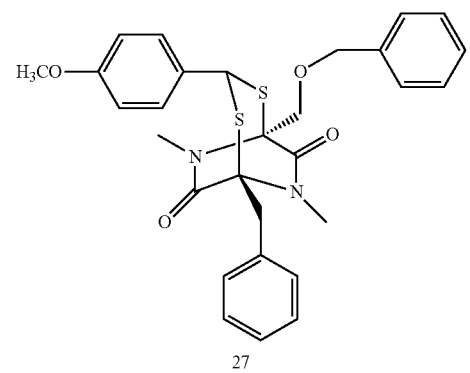

27

Crystalline 26 (144 mg, 0.35 mmol, 1 eq) and phenyl chloromethyl ether (500 μL, 455 mg, 1.75 mmol, 5 eq., 60% reagent only) was dissolved in anhydrous THF (40 mL). The solution was cooled to −78° C. and to the stirred mixture 1.54 M n-butyllithium in hexane (1.16 mL, 1.8 mmol, 1.5 eq) was added dropwise over a period of 5 min. After the mixture was stirred for 10 min at −78° C. the resulting red, cloudy solution was allowed to warm to room temperature and was stirred. Saturated NaCl solution was added into the reaction mixture and the red solution was extracted with dichloromethane. The organic phase was washed with water twice, dried under $MgSO_4$ and concentrated under vacuum. The syrup was separated on column (hexane-ethylacetate, 8-2, Rf 0.4) to give 114 mg of 27 as a glass-like solid (62%). $^1$H NMR ($CDCl_3$, TMS, ppm) δ: 7.35 (m, 5H), 7.28 (d, J=8.8 Hz, 2H), 6.86 (d, J=8.7 Hz, 2H), 5.02 (s, 1H), 4.72 (d, J=11.7 Hz, 1H), 4.58 (d, J=12.0 Hz, 1H), 4.51 (d, J=10.8 Hz, 1H), 4.20 (d, J=16.5 Hz, 1H), 3.78 (s, 3H), 3.74 (d, J=10.5 Hz, 1H), 3.25 (d, J=16.9 Hz, 1H), 3.19 (s, 3H), 3.15 (s, 3H). FAB-MS: Calcd. for $C_{29}H_{30}N_2O_4S_2$: 534.1. Found [M+H]+: 535.0.

Preparation of 3-(4-methoxyphenyl)-6,8-dimethyl-1-hydroxymethyl-5-(phenylmethyl)2,4-dithia-6,8-diaz-abicyclo[3.2.2]nonane-7,9-dione (28)

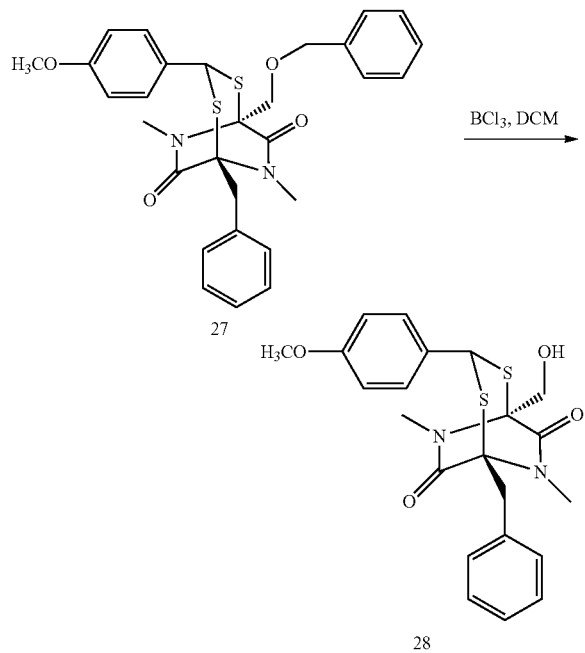

The solution of 28 (60 mg, 0.11 mmol, 1 eq.) in anhydrous dichloromethane (15 mL) was cooled to 0° C. To this stirred reaction mixture 1M boron trichloride in dichloromethane (200 µL, 0.2 mmol, 1.8 eq.) was added dropwise over a period of 30 seconds. The solution was allowed to be stirred at 0° C. for 10 min. and then poured into ice water. The water phase was extracted with dichloromethane. The organic phase was washed with water, dried under $MgSO_4$ and concentrated under vacuum to gain 38 mg crude product. The glassy solid was purified on column with a mixture of dichloromethane-EtOAc (65-35, Rf 0.35), to give 28 mg of pure 28, (57% yield). $^1$H NMR ($CDCl_3$, TMS, ppm) δ: 7.35-7.14 (m, 7H), 6.86 (d, J=8.5 Hz, 2H), 5.04 (s, 1H), 4.66 (dd, J=5.1 and 12.5 Hz, 1H), 4.24 (d, J=16.5 Hz, 1H), 3.87 (dd, J=9.5 and 12.8 Hz, 1H), 3.80 (s, 3H), 3.25 (d, J=16.3 Hz, 1H), 3.24 (s, 3H), 3.14 (s, 3H) 2.73 (dd, J=5.7 and 9.7 Hz, 1H). FAB-MS: Calcd. for $C_{22}H_{24}N_2O_4S_2$: 444.1. Found $[M+H]^+$: 444.9.

Preparation of 1,4-dimethyl-3-hydroxymethyl-6-phenylmethyl-2,5-piperazinedione-3,6-disulfide (29)

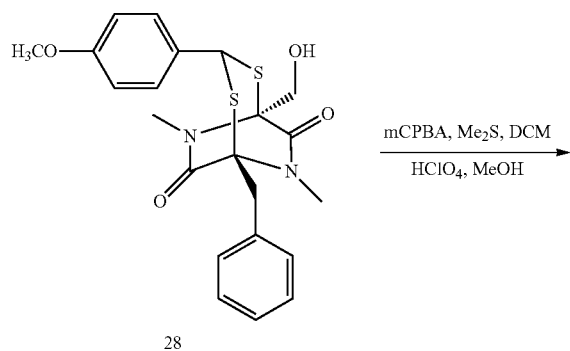

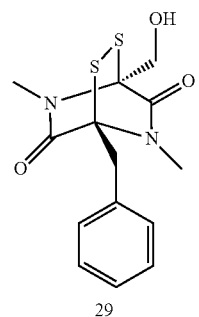

The solution of 28 (25 mg, 0.056 mmol, 1 eq.) in anhydrous dichloromethane (15 mL) was cooled to 0° C. To this, stirred solution m-chloroperbenzoic acid (15 mg, 0.0672 mmol, 1.2 eq, max 77% pure) was added. After 10 min of stirring at 0° C. dimethyl sulfide (20 µL) was added. The solution was then treated with 25 µL of perchloric acid in methanol (1:5). The solution was allowed to stand at room temperature for 9 hr and then purred into saturated sodium bicarbonate solution. The aqueous layer was extracted with dichloromethane. The organic phase was washed with water, dried under $MgSO_4$ and concentrated under vacuum to gain 10 mg crude product. The glassy solid was purified on column with a mixture of dichloromethane-EtOAc (97.5-2.5, Rf 0.3) to give 4 mg of 29 (22% yield). $^1$H NMR ($CDCl_3$, TMS, ppm) δ: 7.30 (m, 5H), 4.34 (d, J=8.0 Hz, 2H), 4.08 (d, J=12.8 Hz, 1H), 3.65 (d, J=13.0 Hz, 1H), 3.50 (d, J=7.9 Hz, 1H), 3.22 (s, 3H), 3.00 (s, 3H).

Assessment of in vitro Activity of Synthetic ETPs

Three types of biological assays were used to evaluate efficacy of our compounds in cell culture: 1) luciferase-based assays for measuring activity of HIF1 inducible promoter; 2) measurement of the messenger RNA levels of the endogenous genes by quantitative reverse transcriptase-polymerase chain reaction; and 3) analysis of the levels of VEGF and c-Met protein levels by western blot analysis.

We employed these assays to evaluate the relative levels of gene expression in three human cell lines: HeLa (human cervical epithelial adenocarcinoma), MCF7 (benign human breast carcinoma) and MDA-MB-231 (malignant breast carcinoma) were treated with the title ETP compounds, DKP control NP481 and chetomin CTM. In parallel, the untreated cells were used as controls. Luciferase and ELISA experiments were carried out in triplicate, with RT-PCR experiments were repeated six times.

Figure 6:
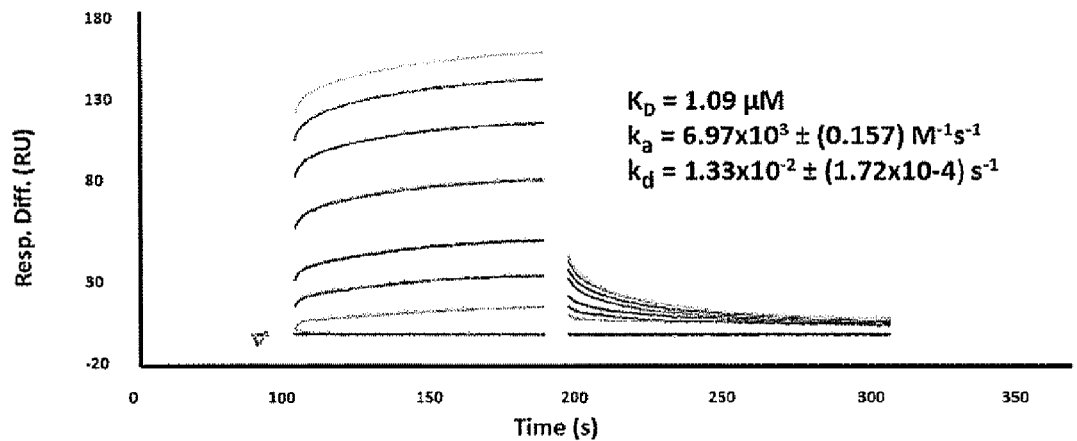
FIG. 6 SPR data for direct binding of LS69 to immobilized fusion protein GST-CH1-p300. Binding constant of 1.09 μM was obtained.
Figure 7:
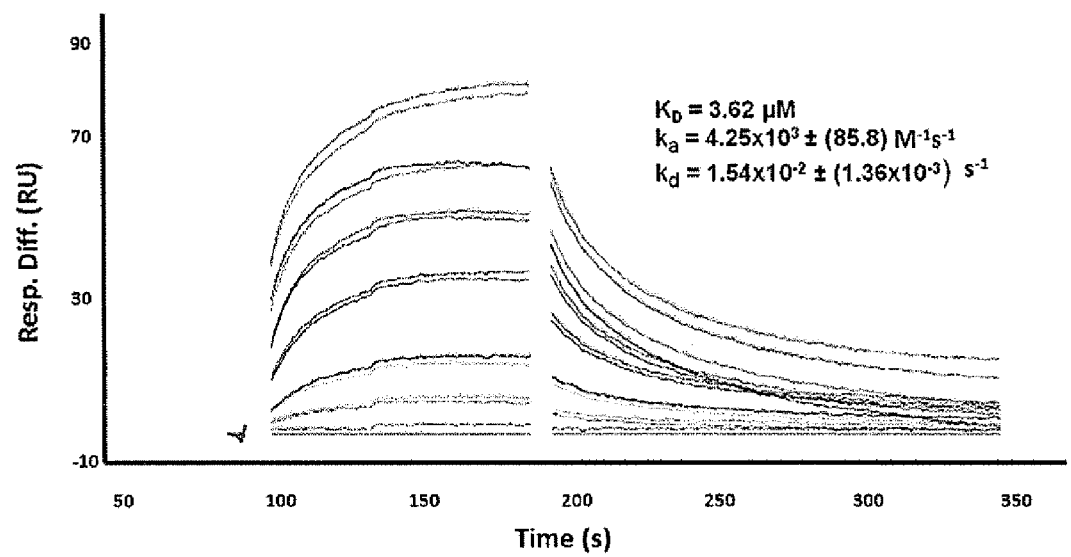
FIG. 7 SPR sensorgrams showing binding of LS72 to immobilized GST-CH1-p300. Binding constant of 3.62 μM was obtained.

Luciferase assays. MDA-MB-231-hRE-Luc cells were maintained in high glucose Dulbecco's Modified Eagles' Medium (DMEM) supplemented with 10%© fetal bovine serum and 0.4 g/L Geneticin (G418 sulfate, RPI Corporation). Cells were plated in 24-well dishes (BD Falcon) at a density of $6\times10^4$ cells/well using 1 mL of a $6.5\times10^4$ cell/mL suspension. After attachment had occurred, cells were treated with 1 mL of fresh media containing synthetic ETP compounds or chetomin in concentrations ranging from 10 nM to 1 µM. Cells were incubated for 6 h at 37° C. in a humidified atmosphere with 5% $CO_2$. Hypoxia was induced by adding desferrioxamine mesylate (DFO, Sigma) to a final concentration of 300 µM, and cells were incubated for an additional 18 hours. Whole cell lysate was isolated by washing the cells twice with ice cold PBS and then adding 150 µL of Cell Culture Lysis Reagent (CCLR, Promega). Lysate was collected, centrifuged at 13,000 rpm at 4° C., aliquoted, and stored at −80° C. Luciferase assays were conducted by allowing whole cell lysate and Luciferase Assay Reagent (Promega) come to ambient temperature for 1 hour prior to use. Luciferase assays were conducted according to the manufacturer's instructions (Promega) using a Turner TD-20e Luminometer. Relative light intensity measurements were normalized by performing a Bradford assay to determine the protein content of the lysate used in the luciferase assay. Briefly, 50 µL of cell lysate/luciferase assay reagent mix was added to 200 µL of Bradford reagent and 750 µl, of Millipore water in a 1.5 mL cuvette. Protein standards were created in the range of 1 mg/mL to 10 µg/mL using an appropriate amount of a 1 mg/mL BSA solution. Absorbance was measured at 595 nM using a DU-800 spectrophotometer. The experiments were carried out in triplicate. The results are presented in FIG. 6 with the bar graphs represent mean values, and error bars—standard error of the mean value.

Cell Culture and Isolation of mRNA

HeLa cells were maintained in high glucose Dulbecco's Modified Eagle's Medium (DMEM, Sigma) supplemented with 8% fetal bovine serum (Irvine Scientific) according to the published procedure.[69] The cells were plated in 6-well dishes (BD Falcon) at density of $1.5 \times 10^5$ cells/well using 2 mL of a $6 \times 10^4$ cell/mL suspension. After attachment had occurred, cells were treated with 1 mL of fresh media containing synthetic ETP compounds or chetomin in concentrations ranging from 10 nM to 1 µM. After a 6 h incubation period at 37° C. in a humidified atmosphere with 5% $CO_2$, hypoxia was induced by adding desferrioxamine mesylate (DFO, Sigma) to a final concentration of 300 µM and incubating cells for another 18 hours. Cells were washed twice with ice cold PBS and lysed immediately. Total RNA was isolated with RNeasy kit (Qiagen) according to the manufacturer's instructions and quantified by UV absorbance. The isolated RNA was further treated with DNase I (Ambion, DNAfree kit) to remove any remaining genomic DNA. Reverse transcription was performed with Powerscript II Reverse Transcriptase (Clontech) as recommended by the manufacturer.

MCF7 cells were maintained in RPMI-1640 media (Sigma) supplemented with 10% fetal bovine serum (Irvine Scientific). Cells were plated in 6-well dishes at a density of $2.4 \times 10^5$ cells/well using 2 mL of a $1.2 \times 10^5$ cell/mL suspension. After attachment had occurred, cells were treated with 1 mL of fresh media containing synthetic ETP compounds or chetomin in concentrations ranging from 10 nM to 1 µM. After a 6 h incubation period at 37° C. in a humidified atmosphere with 5% $CO_2$, hypoxia was induced by adding desferrioxamine mesylate (DFO, Sigma) to a final concentration of 300 µM and incubating cells for another 18 hours. Cells were washed twice with ice cold PBS and lysed immediately. Total RNA was isolated with RNeasy kit (Qiagen) according to the manufacturer's instructions and quantified by UV absorbance. The isolated RNA was further treated with DNase I (Ambion, DNAfree kit) to remove any remaining genomic DNA. Reverse transcription was performed with Powerscript II Reverse Transcriptase (Clontech) as recommended by the manufacturer.

Analysis of gene expression with affymetrix microarrays. Real-time

Quantitative Reverse Transcript PCR (qRT-PCR) was employed to determine the effect of ETP compounds on VEGF and GLUT1 genes in HeLa cells both under normoxic and hypoxic conditions. For VEGF analysis, the forward primer 5'-AGG CCA GCA CAT AGG AGA GA-3' and reverse primer 5'-TTT CCC TTT CCT CGA ACT GA-3' were used to amplify a 104-bp fragment from the 3'-translated region of the gene. For GLUT1 (SLC2A1) analysis we utilized the following sequences to yield a product of 179 bp: forward sequence 5'-TAG AAA CAT GGT TTT GAA ATG C-3', reverse sequence 5'-GGT AAC AGG GAT CAA ACA GAT T-3'. RNA levels were standardized by quantification of the β-glucuronidase as housekeeping gene. The forward primer 5'-CTC ATT TGG AAT TTT GCC GAT T-3' and reverse primer 5'-CCG AGT GAA GAT CCC CTT TTT A-3' were used for this gene. The experiment was performed with Applied Biosystems SYBR Green RT-PCR master mix. Temperature cycling and detection of the SYBR green emission were performed with an ABI 7300 real-time PCR instrument. Data were analyzed with Applied Biosystems Sequence Detection System, version 1.2. Statistical analysis was performed with the data from six independent experiments.

Western blot analysis of VEGF and c-Met protein levels. MCF7 and MDA-MB-231 cells were plated in 60 mm diameter cell culture dishes (BD Falcon) to a density of $1.0 \times 10^6$ cells/mL. After attachment, they were treated with media containing chetomin (200 nM), LS72 and LS75 (400 nM). All samples contained a final concentration 0.1-0.2% v/v of DMSO. After a 6 hour incubation period, hypoxia was induced with 300 µM DFO in MCF7 and with 150 $CoCl_2$ in MDA-MB-231 cells. Samples were incubated for an additional 18 hours. Total cellular proteins were extracted from the cells using cell lysis buffer according to manufacturer's protocol (Cell Signaling). Protein concentrations were measured with BCA Protein assay kit (Pierce/Thermo Scientific). Equal amounts of protein samples were subjected to SDS-PAGE and electroblotted to PVDF membrane (Bio-Rad). These were probed first with an anti-VEGF mouse monoclonal (sc-57496, Santa Cruz Biotechnology) or anti c-Met rabbit polyclonal antibody (sc-10, Santa Cruz Biotechnology), stripped with Restore Western Blot Stripping Buffer (Pierce/Thermo Scientific) and re-probed with a rabbit polyclonal anti-β-actin antibody (4867, Cell Signaling).

After washing with tris-buffered saline—Tween 20 (TBST) solution, the membranes were incubated with horseradish peroxidase (HRP)-conjugated secondary antibodies (Santa Cruz Biotechnology). Signals were detected by using SuperSignal chemiluminescent kit (Pierce/Thermo Scientific).

Animal use. Animal experiments were done in accordance with federal guidelines following review and approval by the PRISM Institutional Animal Care and Use Committee. (IACUC). Athymic nude mice were purchased from Harlan at the age of 8-9 weeks.

Fluorescent tumor cell lines. N202 (gift from Joseph Lustgarten, Mayo Clinic, Scottsdale, Ariz.) were maintained in DMEM High Glucose supplemented with L-glutamine (2 mM), penicillin (100 U/ml), streptomycin (100 U/ml), sodium pyruvate (1 mM) (Invitrogen, Carlsbad, Calif.) and 10% heat inactivated FBS (Omega Scientific, Tarzana, Calif.) at 37° C. in 5% $CO_2$ in air. The histone H2B-GFP was subcloned into the SalI/HpaI sites in the LXRN vector (Clontech, Palo Alto, Calif.) using SalI and blunted NotI sites from the BOSH2BGFPN1 vector[70], N202 were transduced with the viable virus to stably incorporate the H2B-GFP gene. The transduced cells were FACs sorted twice to ensure 100% of the cells stably expressed the H2B-GFP protein.

Mouse xenograft tumor models. Classic IVM tumor model[71] was used with minor modifications. The mice, usually athymic nude mice (25-30 g body weight), were anesthetized (7.3 mg ketamine hydrochloride and 2.3 mg xylazine per 100 g body weight, intraperitoneal injection) and placed on a heating pad. A titanium frame was placed onto the dorsal skinfold of mice to sandwich the extended double layer of skin. A 15 mm diameter full-thickness circular layer of skin was then excised. The superficial fascia on top of the remaining skin is carefully removed to expose the underlying muscle and subcutaneous tissue which is then covered with another titanium frame with a glass cover slip to form the window chamber. After a recovery period of 1-2 days, tumor spheroids were implanted. Tumor spheroids were formed by plating 50,000 N202 cells onto 1% agar-coated 96-well non-tissue culture treated flat bottom dishes (20 µl cells in 100 µl medium) and centrifuging 4 times at 2000 rpm for 15 min, rotating the dish after every centrifugation. The cells were incubated an additional 3-7 days (depending on cell type) at 37° C. in 5%© $CO_2$ in air to form tight spheroids. The tumor spheroids were implanted directly onto the dorsal skin in the window chamber alone. Tumors were allowed to vascularize over 10-14 days before the injection of 1 mg/kg of LS72 compound at Day 0, followed by the daily administration at 2 mg/kg at Days 8-13.

Tumor Growth. Analysis of tumor growth with IVM. Tumors were imaged by intravital fluorescence microscopy, as described.[72] Tumor growth was analyzed off-line from the recorded, digital, grayscale 0 to 256 images using Image-Pro Plus (Media Cybernetics, Bethesda, Md.). Tumor growth was determined by quantifying the cumulative fluorescence signal for the tumor over time. The cumulative tumor fluorescence signal was measured by signal summation of all pixels over 75. All growth curves are normalized to the tumor on day 0 after treatment.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

TABLE 1

| Symbol | Entrez Gene ID | LS72 |
|---|---|---|
| TGFB3 | 7043 | −1.5 |
| TFRC | 7037 | −1.5 |
| LOXL2 | 4017 | −1.4 |
| CAV1 | 857 | −1.3 |
| MET | 4233 | −2.2 |
| SLC35D1 | 23169 | −3.1 |

List of important HIF1α inducible genes that are downregulated under hypoxic induction with DFO (300 µM) by treatment with LS72 (400 nM).

TABLE 2

| Symbol | Entrez Gene ID | LS72 |
|---|---|---|
| SLC35D1 | 23169 | −3.1 |
| SLC5A8 | 160728 | −1.4 |
| SLC25A15 | 10166 | −1.5 |
| SLC9A3R1 | 9368 | −1.6 |
| SLC39A11 | 201266 | −1.9 |
| SLC9A2 | 6549 | −1.8 |
| SLC5A6 | 8884 | −2.4 |
| SLC25A12 | 8604 | −1.8 |
| SLC26A2 | 1836 | −1.4 |
| SLC38A9 | 153129 | −1.5 |
| SLC35A1 | 10559 | −2.2 |
| SLC7A2 | 6542 | −2.5 |
| SLC27A4 | 10999 | −1.4 |

List of Solute Carrier (SLC) family genes that are downregulated in MCF7 cells under hypoxic induction with DFO (300 µM) upon treatment with LS72 (400 nM).

REFERENCES

All references herein, including the foregoing, are incorporated herein by reference in their entirety.

1. Semenza, G. L. (2007) Hypoxia and cancer *Cancer Metastasis Rev.* 26, 223-+2. Gatenby, R. A., and Gillies, R. J. (2004) Why do cancers have high aerobic glycolysis? *Nat. Rev. Cancer* 4, 891-899
3. Gatenby, R. A., Gawlinski, E. T., Gmitro, A. F., Kaylor, B., and Gillies, R. J. (2006) Acid-mediated tumor invasion: a multidisciplinary study *Cancer Res.* 66, 5216-5223
4. Lum, J. J., Bui, T., Gruber, M., Gordan, J. D., DeBerardinis, R. J., Covello, K. L., Simon, M. C., and Thompson, C. B. (2007) The transcription factor HIF-1 alpha plays a critical role in the growth factor-dependent regulation of both aerobic and anaerobic glycolysis *Genes Dev.* 21, 1037-1049
5. Kim, J. W., and Dang, C. V. (2006) Cancer's molecular sweet tooth and the Warburg effect *Cancer Res.* 66, 8927-8930
6. Gillies, R. J., and Gatenby, R. A. (2007) Hypoxia and adaptive landscapes in the evolution of carcinogenesis *Cancer Metastasis Rev.* 26, 311-317
7. Brown, J. M., and Wilson, W. R. (2004) Exploiting tumour hypoxia in cancer treatment 4, 437-447
8. Vaupel, P., Schlenger, K., Knoop, C., and Höckel, M. (1991) Oxygenation of Human Tumors: Evaluation of Tissue Oxygen Distribution in Breast Cancers by Computerized O2 Tension Measurements 51, 3316-3322
9. Tannock, I. F. (1968) RELATION BETWEEN CELL PROLIFERATION AND VASCULAR SYSTEM IN A TRANSPLANTED MOUSE MAMMARY TUMOUR *Br. J. Cancer* 22, 258-&
10. Comerford, K. M., Wallace, T. J., Karhausen, J., Louis, N. A., Montalto, M. C., and Colgan, S. P. (2002) Hypoxia-inducible factor1-dependent regulation of the multidrug resistance ($MDR_1$) gene *Cancer Res.* 62, 3387-3394
11. Wartenberg, M., Ling, F. C., Muschen, M., Klein, F., Acker, H., Gassmann, M., Petrat, K., Putz, V., Hescheler, J., and Sauer, H. (2003) Regulation of the multidrug resistance transporter P-glycoprotein in multicellular tumor spheroids by hypoxiainducible factor-1 and reactive oxygen species *Faseb J.* 17, 503-+
12. Durand, R. E. (1994) The influence of microenvironmental factors during cancer therapy 8, 691-702
13. Tannock, I. F. (1998) Conventional cancer therapy: promise broken or promise delayed? 351, SII9-SII16
14. Harris, A. L. (2002) Hypoxia—A key regulatory factor in tumour growth *Nat. Rev. Cancer* 2, 38-47
15. Pennacchietti, S., Michieli, P., Galluzzo, M., Mazzone, M., Giordano, S., and Comoglio, P. M. (2003) Hypoxia promotes invasive growth by transcriptional activation of the met protooncogene *Cancer Cell* 3, 347-361
16. Graeber, T. G., Osmanian, C., Jacks, T., Housman, D. E., Koch, C. J., Lowe, S. W., and Giaccia, A. J. (1996) Hypoxia-mediated selection of cells with diminished apoptotic potential in solid tumours *Nature* 379, 88-91
17. Semenza, G. L. (2001) Hypoxia-inducible factor 1: oxygen homeostasis and disease pathophysiology *Trends Mol. Med* 7, 345-350
18. Ivan, M., Kondo, K., Yang, H. F., Kim, W., Valiando, J., Ohh, M., Salic, A.,
Asara, J. M., Lane, W. S., and Kaolin, W. G. (2001) HIF alpha targeted for VHL-mediated destruction by proline hydroxylation: Implications for O-2 sensing *Science* 292, 464-468

19. Kaelin, W. G. (2002) Molecular basis of the VHL hereditary cancer syndrome *Nat. Rev. Cancer* 2, 673-682
20. Maxwell, P. H., Wiesener, M. S., Chang, G. W., Clifford, S. C., Vaux, E. C., Cockman, M. E., Wykoff, C. C., Pugh, C. W., Maher, E. R., and Ratcliffe, P. J. (1999) The tumour suppressor protein VHL targets hypoxia-inducible factors for oxygen-dependent proteolysis *Nature* 399, 271-275
21. Wood, S. M., Gleadle, J. M., Pugh, C. W., Hankinson, O., and Ratcliffe, P. J. (1996) The role of the aryl hydrocarbon receptor nuclear translocator (ARNT) in hypoxic induction of gene expression—Studies in ARNT-deficient cells *J. Biol. Chem.* 271, 15117-15123
22. O'Rourke, J. F., Dachs, G. U., Gleadle, J. M., Maxwell, P. H., Pugh, C. W., Stratford, I. J., Wood, S. M., and Ratcliffe, P. J. (1997) Hypoxia response elements *Oncol. Res.* 9, 327-332
23. Forsythe, J. A., Jiang, B. H., Iyer, N. V., Agani, F., Leung, S. W., Koos, R. D., and Semenza, G. L. (1996) Activation of vascular endothelial growth factor gene transcription by hypoxia-inducible factor 1 *Mol. Cell. Biol.* 16, 4604-4613
24. Okino, S. T., Chichester, C. H., and Whitlock, J. P. (1998) Hypoxia-inducible mammalian gene expression analyzed in vivo at a TATA-driven promoter and at an initiator-driven promoter *J. Biol. Chem.* 273, 23837-23843
25. Lando, D., Pongratz, I., Poellingers, L., and Whitelaw, M. L. (2000) A redox mechanism controls differential DNA binding activities of hypoxia-inducible factor (HIF) 1 alpha and the HIF-like factor *J. Biol. Chem.* 275, 4618-4627
26. Lando, D., Gorman, J. J., Whitelaw, M. L., and Peet, D. J. (2003) Oxygen-dependent regulation of hypoxia-inducible factors by prolyl and asp araginyl hydroxylation *Eur. J. Biochem.* 270, 781-790
27. Lando, D., Peet, D. J., Gorman., J. J., Whelan, D. A., Whitelaw, M. L., and Bruick, R. K. (2002) FIH-1 is an asparaginyl hydroxylase enzyme that regulates the transcriptional activity of hypoxia-inducible factor *Genes Dev.* 16, 1466-1471
28. Lando, D., Peet, D. J., Whelan, D. A., Gorman, J. J., and Whitelaw, M. L.
(2002) Asp aragine hydroxylation of the HIF transactivation domain: A hypoxic switch *Science* 295, 858-861
29. Hewitson, K. S., McNeil, L. A., Riordan, M. V., Tian, Y. M., Bullock, A. N., Welford, R. W., Elkins, J. M., Oldham, N. J., Bhattacharya, S., Gleadle, J. M., Ratcliffe, P. J., Pugh, C. W., and Schofield, C. J. (2002) Hypoxia-inducible factor (HIF) asparagine hydroxylase is identical to factor inhibiting HIF (FIH) and is related to the cupin structural family *J. Biol. Chem.* 277, 26351-26355
30. Metzen, E., and Ratcliffe, P. J. (2004) HIF hydroxylation and cellular oxygen sensing *Biol. Chem.* 385, 223-230
31. Arany, Z., Huang, L. E., Eckner, R., Bhattacharya, S., Jiang, C., Goldberg, M. A., Bunn, H. F., and Livingston, D. M. (1996) An essential role for p300/CBP in the cellular response to hypoxia *Proc. Natl. Acari Sci. U.S.A.* 93, 12969-12973
32. Vleugel, M. M., Shvarts, D., van der Wall, E., and van Diest, P. J. (2006) p300 and p53 levels determine activation of HIF-1 downstream targets in invasive breast cancer *Hum. Pathol.* 37, 1085-1092
33. Kasper, L. H., Boussouar, F., Boyd, K., Xu, W., Biesen, M., Rehg, J., Baudino, T. A., Cleveland, J. L., and Brindle, P. K. (2005) Two transactivation mechanisms cooperate for the bulk of HIF-1-responsive gene expression *Embo J.* 24, 3846-3858
34. Kallio, P. J., Okamoto, K., O'Brien, S., Carrero, P., Makino, Y., Tanaka, H., and Poellinger, L. (1998) Signal transduction in hypoxic cells: inducible nuclear translocation and recruitment of the CBPIp300 coactivator by the hypoxia-inducible factor-1 alpha *Embo J.* 17, 6573-6586
35. Ebert, B. L., and Bunn, H. F. (1998) Regulation of transcription by hypoxia requires a multiprotein complex that includes hypoxia-inducible factor 1, an adjacent transcription factor, and p300/CREB binding protein *Mol. Cell. Biol.* 18, 4089-4096
36. Kobayashi, A., NumayamaTsuruta, K., Sogawa, K., and FujiiKuriyama, Y. (1997) CBP/p300 functions as a possible transcriptional coactivator of Ah receptor nuclear translocator (Arnt) *J. Biochem.* (Tokyo) 122, 703-710
37. Giaccia, A., Siim, B. G., and Johnson, R. S. (2003) HIF-1 as a target for drug development *Nat. Rev. Drug Discov.* 2, 803-811
38. Sun, X., Kanwar, J. R., Leung, E., Lehnert, K., Wang, D., and Krissansen, G. W. (2001) Gene transfer of antisense hypoxia inducible factor-1 alpha enhances the therapeutic efficacy of cancer immunotherapy *Gene Ther.* 8, 638-645
39. Mabjeesh, N. J., Escuin, D., LaVallee, T. M., Pribluda, V. S., Swartz, G. M., Johnson, M. S., Willard, M. T., Zhong, H., Simons, J. W., and Giannakakou, P. (2003) 2ME2 inhibits tumor growth and angiogenesis by disrupting microtubules and dysregulating HIF *Cancer Cell* 3, 363-375
40. Eid, J. E., Kung, A. L., Scully, R., and Livingston, D. M. (2000) P300 interacts with the nuclear proto-oncoprotein SYT as part of the active control of cell adhesion *Cell* 102, 839-848
41. Hirota, K., and Semenza, G. L. (2006) Regulation of angiogenesis by hypoxia-inducible factor 1 *Crit. Rev. Oncol./Hematol.* 59, 15-26
42. Ramanathan, A., Wang, C., and Schreiber, S. L. (2005) Perturbational profiling of a cell-line model of tumorigenesis by using metabolic measurements *Proc. Natl. Acad. Sci. U.S.A.* 102, 5992-5997
43. Underiner, T. L., Ruggeri, B., and Gingrich, D. E. (2004) Development of vascular endothelial growth factor receptor (VEGFR) kinase inhibitors as anti-angiogenic agents in cancer therapy *Curr. Med. Chem.* 11, 731-745
44. Kung, A. L., Zabludoff, S. D., France, D. S., Freedman, S. J., Tanner, E. A., Vieira, A., Cornell-Kennon, S., Lee, J., Wang, B. Q., Wang, J. M., Memmert, K., Naegeli, H. U., Petersen, F., Eck, M. J., Bair, K. W., Wood, A. W., and Livingston, D. M. (2004) Small molecule blockade of transcriptional coactivation of the hypoxia-inducible factor pathway *Cancer Cell* 6, 33-43
45. Foster, B. A., Coffey, H. A., Morin, M. J., and Rastinejad, F. (1999) Pharmacological rescue of mutant p53 conformation and function *Science* 286, 2507-2510
46. Arkin, M. R., and Wells, J. A. (2004) Small-molecule inhibitors of protein-protein interactions: Progressing towards the dream *Nat. Rev. Drug Discov.* 3, 301-317

47. Issaeva, N., Bozko, P., Enge, M., Protopopova, M., Verhoef, L., Masucci, M., Pramanik, A., and Selivanova, G. (2004) Small molecule RITA binds to p53, blocks p53-HDM-2 interaction and activates p53 function in tumors *Nat. Med.* 10, 1321-1328
48. Lepourcelet, M., Chen, Y. N. P., France, D. S., Wang, H. S., Crews, P., Petersen, F., Bruseo, C., Wood, A. W., and Shivdasani, R. A. (2004) Small-molecule antagonists of the oncogenic Tcf/beta-catenin protein complex *Cancer Cell* 5, 91-102
49. Vassilev, L. T., Vu, B. T., Graves, B., Carvajal, D., Podlaski, F., Filipovic, Z., Kong, N., Kammlott, U., Lukacs, C., Klein, C., Fotouhi, N., and Liu, E. A. (2004) In vivo activation of the p53 pathway by small-molecule antagonists of MDM2 *Science* 303, 844-848
50. Grasberger, B. L., Lu, T. B., Schubert, C., Parks, D. J., Carver, T. E., Koblish, H. K., Cummings, M. D., LaFrance, L. V., Milkiewicz, K. L., Calvo, R. R., Maguire, D., Lattanze, J., Franks, C. F., Zhao, S. Y., Ramachandren, K., Bylebyl, G. R., Zhang, M., Manthey, C. L., Petrella, E. C., Pantoliano, M. W., Deckman, I. C., Spurlino, J. C., Maroney, A. C., Tomczuk, B. E., Molloy, C. J., and Bone, R. F. (2005) Discovery and cocrystal structure of benzodiazepinedione HDM2 antagonists that activate p53 in cells *J. Med. Chem.* 48, 909-912
51. Ang, S. O., Chen, H., Hirota, K., Gordeuk, V. R., Jelinek, J., Guan, Y. L., Liu, E. L., Sergueeva, A. I., Miasnikova, G. Y., Mole, D., Maxwell, P. H., Stockton, D. W., Semenza, G. L., and Prchal, J. T. (2002) Disruption of oxygen homeostasis underlies congenital Chuvash polycythemia *Nature Genet.* 32, 614-621
52. Berg, T., Cohen, S. B., Desharnais, J., Sonderegger, C., Maslyar, D. J., Goldberg, J., Boger, D. L., and Vogt, P. K. (2002) Small-molecule antagonists of Myc/Max dimerization inhibit Myc-induced transformation of chicken embryo fibroblasts *Proc. Natl. Acad. Sci. U.S.A.* 99, 3830-3835
53. De Munari, S., Grugni, M., Menta, E., Cassin, M., and Colella, G. (2006) Use Of Diketodithiopiperazine Antibiotics For The Preparation Of Antiangiogenic Pharmaceutical Compositions.
54. Hauser, D., Weber, H. P., and Sigg, H. P. (1970) Isolation and Structure Elucidation of Chaetocin *Helv. Chim. Acta* 53, 1061-&
55. Waksman, S. A., and Bugie, E. (1944) Chaetomin, a new antibiotic substance produced by chaetomium cochliodes I. Formation and properties *J. Bacterial.* 48, 527-530
56. Gardiner, D. M., Waring, R, and Howlett, B. J. (2005) The epipolythiodioxopiperazine (ETP) class of fungal toxins: distribution, mode of action, functions and biosynthesis *Microbiology*-(U)151, 1021-1032
57. Brewer, D., Archibal. Rm, Safe, S., Taylor, A., Stevenso. Rg, Vining, L. C., Duncan, J. M., Christen.Cm, Mirocha, C. J., Leach, C. K., and Jerram, W. A. (1972) Ovine Ill-Thrift in Nova-Scotia 0.5. Production and Toxicology of Chetomin, a Metabolite of *Chaetomium* Spp *Can. J. Microbial.* 18, 1129-&
58. Sekita, S., Yoshihira, K., Natori, S., Udagawa, S., Mural, T., Sugiyama, Y., Kurata, H., and Umeda, M. (1981) Myco-Toxin Production by *Chaetomium* Spp and Related Fungi *Can. J. Microbial.* 27, 766-772
59. Bernardo, P. H., Brasch, N., Chai, C. L. L., and Waring, P. (2003) A novel redox mechanism for the glutathione-dependent reversible uptake of a fungal toxin in cells *J. Biol. Chem.* 278, 46549-46555
60. Fukuyama, T., Nakatsuka, S., and Kishi, Y. (1981) *Total Synthesis of Gliotoxin*, Dehydrogliotoxin and Hyalodendrin Tetrahedron 37, 2045-2078
61. Sasaki, K., Fukuyama, T., Nakatsuka, S., and Kishi, Y. (1975) X-Ray Structure Determination of "3,6-P-Anisylidenedithio-3-Ethyl-Nn' Dimethylpiperazine-2,5-Dione *J. Chem. Soc.-Chem. Commun.*, 542-543
62. Tischer, E., Mitchell, R., Hartman, T., Silva, M., Gospodarowicz, D., Fiddes, J. C., and Abraham, J. A. (1991) The Human Gene for Vascular Endothelial Growth-Factor—Multiple Protein Forms Are Encoded through Alternative Exon Splicing *J. Biol. Chem.* 266, 11947-11954
63. Shibata, T., Giaccia, A. J., and Brown, J. M. (2000) Development of a hypoxia-responsive vector for tumor-specific gene therapy *Gene Thor.* 7, 493-498
64. Block, K. M., Wang, H., Szabo, L. Z., Polaske, N. W., Henehey, L. K., Dubey, R., Kushal, S., Laszlo, C. F., Makhoul, J., Song, Z. H., Meuillet, E. J., and Olenyuk, B. Z. (2009) Direct Inhibition of Hypoxia-Inducible Transcription Factor Complex with Designed Dimeric Epidithiodiketopiperazine *J. Am. Chem. Soc.* 131, 18078-18088
65. Erler, J. T., Bennewith, K. L., Nicolau, M., Dornhofer, N., Kong, C., Le, Q. T., Chi, J. T. A., Jeffrey, S. S., and Giaccia, A. J. (2006) Lysyl oxidase is essential for hypoxia-induced metastasis *Nature* 440, 1222-1226
66. Darash-Yahana, M., Pikarsky, E., Abramovitch, R., Zeira, E., Pal, B., Karplus, R., Beider, K., Avniel, S., Kasem, S., Galun, E., and Peled, A. (2004) Role of high expression levels of CXCR4 in tumor growth, vascularization, and metastasis *Faseb J.* 18, 1240-+
67. Pradervand, S., Paillusson, A., Thomas, J., Weber, J., Wirapati, P., Hagenbuehle, O., and Harshman, K. (2008) Affymetrix Whole-Transcript Human Gene 1.0 ST array is highly concordant with standard 3' expression arrays *Biotechniques* 44, 759-762
68. Affymetrix. (2012). Affymetrix, http://www.affymetrix.com
69. Olenyuk, B. Z., Zhang, G. J., Kleo, J. M., Nickols, N. G., Kaelin, W. G., and Dervan, P. B. (2004) Inhibition of vascular endothelial growth factor with a sequence-specific hypoxia response element antagonist *Proc. Natl. Acad. Sci. U.S.A.* 101, 16768-16773
70. Kanda, T., Sullivan, K. F., and Wahl, G. M. (1998) Histone-GFP fusion protein enables sensitive analysis of chromosome dynamics in living mammalian cells 8, 377-385
71. Frost, G. I., Lustgarten, J., Dudouet, B., Nyberg, L., Hartley-Asp, B., and Borgstrom, P. (2005) Novel syngeneic pseudo-orthotopic prostate cancer model: vascular, mitotic and apoptotic responses to castration 69, 1-9
72. Oh, P., Borgstrom, P., Witkiewicz, H., Li, Y., Borgstrom, B. J., Chrastina, A., Iwata, K., Zinn, K. R., Baldwin, R., Testa, J. E., and Schnitzer, J. E. (2007) Live dynamic imaging of caveolae pumping targeted antibody rapidly and specifically across endothelium in the lung 25, 327-337

What is claimed is:
1. A compound having the structure:
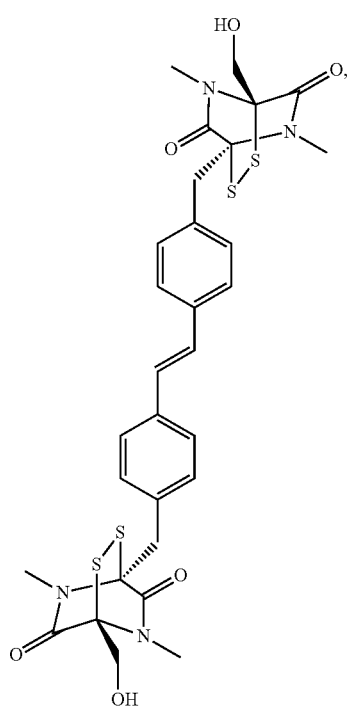
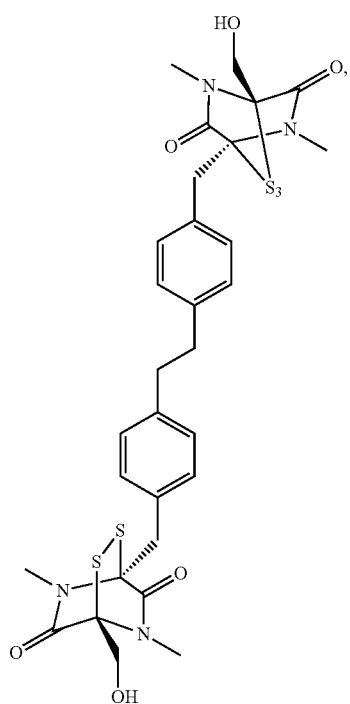
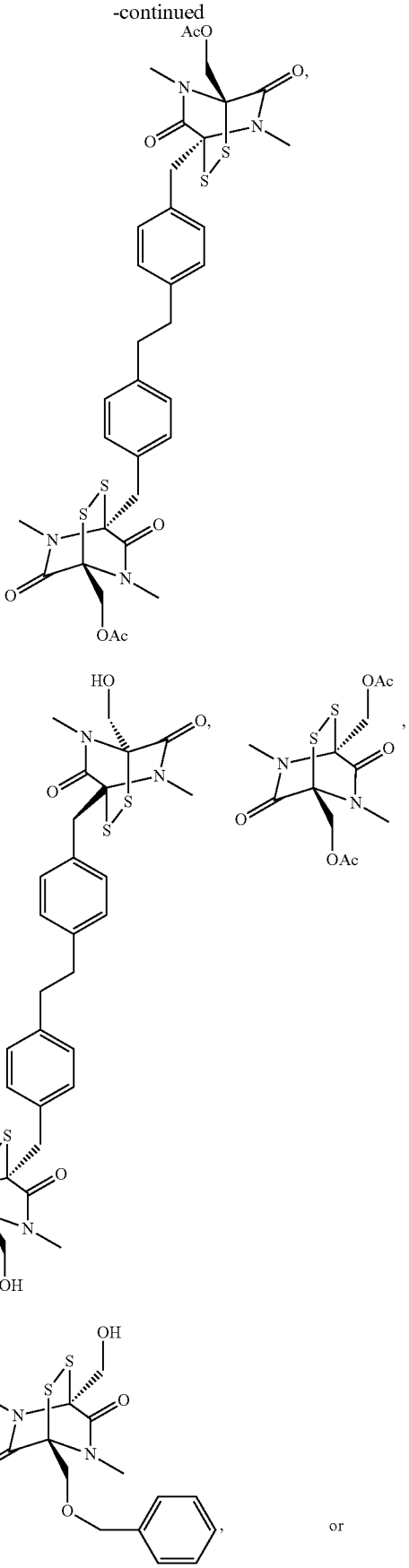

-continued
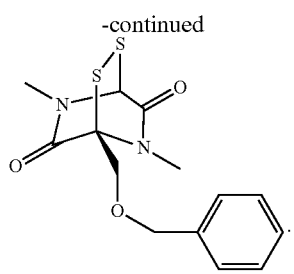
2. The compound of claim 1 having the structure:
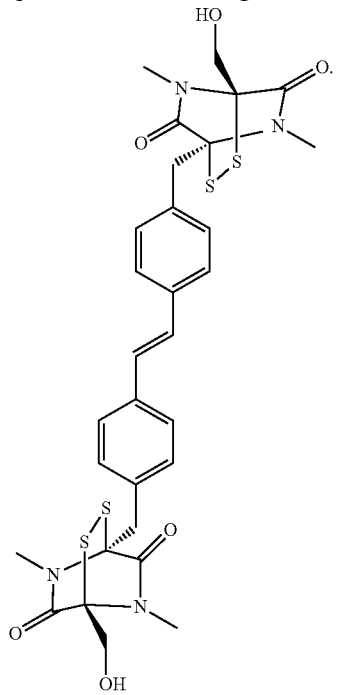
3. The compound of claim 1 having the structure:
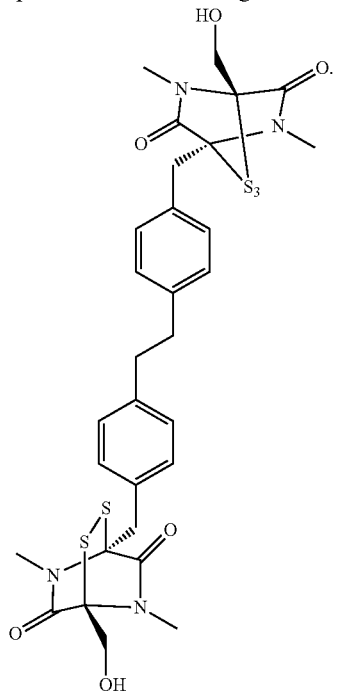
4. The compound of claim 1 having the structure:
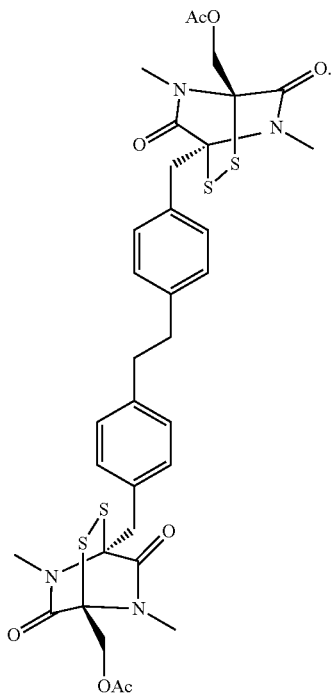
5. The compound of claim 1 having the structure:
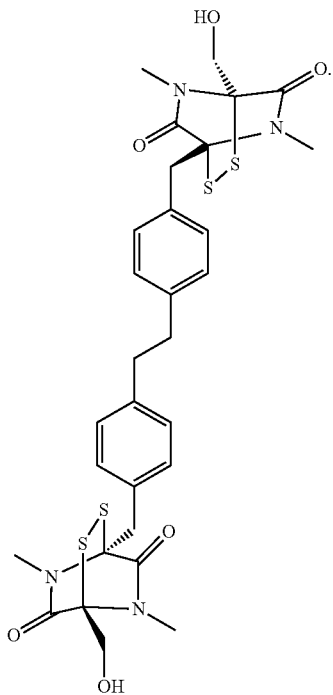

6. The compound of claim 1 having the structure:

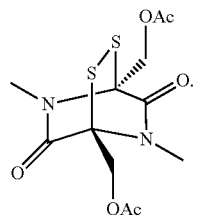

7. The compound of claim 1 having the structure:

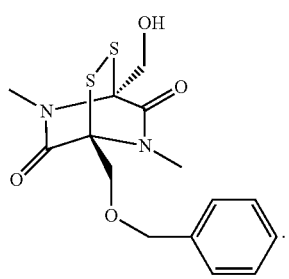 [SMILES: CN1C(=O)[C@]2(COCc3ccccc3)SS[C@@]1(CO)C(=O)N2C]

8. The compound of claim 1 having the structure:

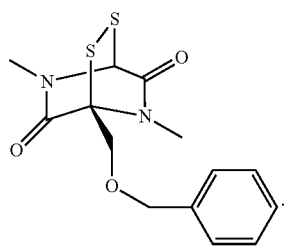 [SMILES: CN1C(=O)[C@]2(COCc3ccccc3)SSC1C(=O)N2C]

9. A pharmaceutical composition comprising a compound of claim 1 dissolved or dispersed in a carrier.

10. The pharmaceutical composition of claim 9, wherein the compound has the structure:

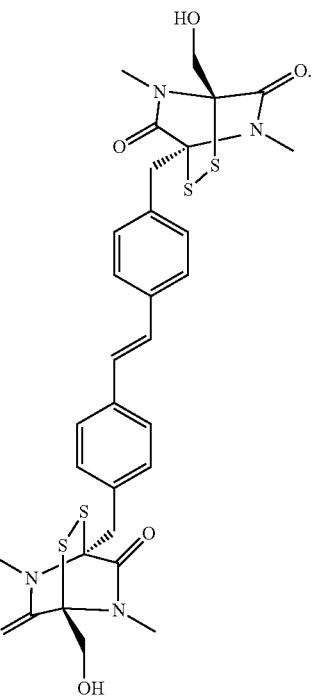

11. A method for treating breast cancer in a subject, comprising administering a therapeutically effective amount of a compound of claim 1 to the subject in need thereof.

12. The method of claim 11, wherein the compound has the structure:

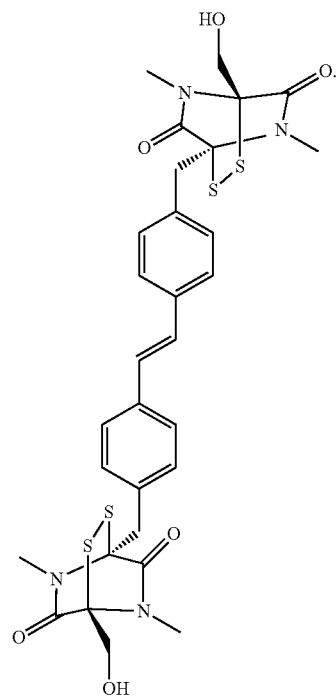

* * * * *